US011839674B2

(12) United States Patent
Traynor et al.

(10) Patent No.: US 11,839,674 B2
(45) Date of Patent: Dec. 12, 2023

(54) COMPOSITIONS COMPRISING SILICON DIOXIDE-BASED PARTICLES INCLUDING ONE OR MORE AGENTS

(71) Applicant: CoLabs International Corporation, Las Vegas, NV (US)

(72) Inventors: Daniel H. Traynor, Sarasota, FL (US); Laura E. Cohen, Huntington Beach, CA (US)

(73) Assignee: CoLabs International Corporation, Las Vegas, NV (US)

( * ) Notice: Subject to any disclaimer, the term of this patent is extended or adjusted under 35 U.S.C. 154(b) by 105 days.

(21) Appl. No.: 16/455,719

(22) Filed: Jun. 27, 2019

(65) Prior Publication Data

US 2020/0000693 A1 Jan. 2, 2020

Related U.S. Application Data

(60) Provisional application No. 62/690,904, filed on Jun. 27, 2018.

(51) Int. Cl.
| | | |
|---|---|---|
| *A61K 8/25* | (2006.01) | |
| *A01N 25/08* | (2006.01) | |
| *A61Q 17/04* | (2006.01) | |
| *A61Q 19/00* | (2006.01) | |
| *A61Q 19/10* | (2006.01) | |
| *A61K 47/02* | (2006.01) | |

(52) U.S. Cl.
CPC ............... *A61K 8/25* (2013.01); *A01N 25/08* (2013.01); *A61K 47/02* (2013.01); *A61Q 17/04* (2013.01); *A61Q 19/007* (2013.01); *A61Q 19/10* (2013.01)

(58) Field of Classification Search
None
See application file for complete search history.

(56) References Cited

U.S. PATENT DOCUMENTS

| | | |
|---|---|---|
| 1,478,208 A | 12/1923 | Duddleson et al. |
| 3,462,479 A | 8/1969 | Strobel et al. |
| 3,691,270 A | 9/1972 | Charle et al. |
| 4,402,977 A | 9/1983 | Grollier et al. |
| 4,540,507 A | 9/1985 | Grollier |
| 4,542,125 A | 9/1985 | Gorman et al. |
| 4,663,155 A | 5/1987 | Murray et al. |
| 4,663,156 A | 5/1987 | Clum et al. |
| 4,683,134 A | 7/1987 | Palinczar |
| 4,686,099 A | 8/1987 | Palinczar |
| 4,699,779 A | 10/1987 | Palinczar |
| 4,701,321 A | 10/1987 | Bernstein |
| 4,749,501 A | 6/1988 | Nakagawa et al. |
| 4,803,195 A | 2/1989 | Holzner |
| 4,874,538 A | 10/1989 | Dawson et al. |
| 4,904,524 A | 2/1990 | Yoh |
| 4,933,174 A | 6/1990 | Bernstein |
| 4,985,170 A | 1/1991 | Dawson et al. |
| 5,071,706 A | 12/1991 | Soper et al. |
| 5,089,269 A | 2/1992 | Noda et al. |
| 5,132,117 A | 7/1992 | Speaker et al. |
| 5,169,624 A | 12/1992 | Ziegler et al. |
| 5,292,801 A | 3/1994 | Avnir et al. |
| 5,300,564 A | 4/1994 | Avnir et al. |
| 5,306,485 A | 4/1994 | Robinson et al. |
| 5,455,048 A | 10/1995 | Lahmani et al. |
| 5,476,660 A | 12/1995 | Somasundaran et al. |
| 5,508,259 A | 4/1996 | Holzner et al. |
| 5,543,136 A | 8/1996 | Aldous |
| 5,589,177 A | 12/1996 | Herb et al. |
| 5,614,217 A | 3/1997 | Chiprich et al. |
| 5,599,555 A | 4/1997 | El-Nokaly |
| 5,620,692 A | 4/1997 | Potter et al. |
| 5,643,341 A | 7/1997 | Hirsch et al. |
| 5,661,189 A | 8/1997 | Grieveson et al. |
| 5,674,912 A | 10/1997 | Martin |
| 5,683,716 A | 11/1997 | Hata et al. |
| 5,716,920 A | 2/1998 | Glenn et al. |
| 5,733,531 A | 3/1998 | Mitchnick et al. |
| 5,759,524 A | 6/1998 | Tanner et al. |

(Continued)

FOREIGN PATENT DOCUMENTS

| | | |
|---|---|---|
| CN | 1341012 A | 3/2002 |
| EP | 0025379 B1 | 6/1984 |

(Continued)

OTHER PUBLICATIONS

Adelia. Fleas Flee from Dermagic Diatomaceous Earth Products (Year: 2016).*
Boissiere, et al. Turning Biopolymer Particles into Hybrid Capsules: the Example of Silica/Alginate Nanocomposites, J. Mater. Chem. 16: 1178-1182 (2006).
Business Wire, Leading Cosmetics Industry Chemist Joins Skin Innovator; Performance Brands Names Michael Dulak to Board of Directors (1999) Best Availabe Copy.
Copyrightkids.org, http://web.archive.org/web/20030919013921 /http://www.copyrightkids.org/definitions. html, Retrieved via WayBack Machine with archive date of Sep. 19, 2003.
Datachem Software Developers of CertiStep, License Agreements, http://web.archive.org/web/20031109074418/http://www.datachemsoftware.com/licenses.htm, retrieved via Wayback Machine with archive date of Nov. 9, 2003.

(Continued)

*Primary Examiner* — Robert T. Crow
*Assistant Examiner* — John P Nguyen
(74) *Attorney, Agent, or Firm* — UltimatEdge IP Law Group, P.C.; Dean G. Stathakis

(57) ABSTRACT

The present specification discloses compositions comprising one or more silicon dioxide-based particles comprising, consisting essentially of or consisting of one or more active agents and methods and uses for the disclosed compositions. A composition disclosed herein can be incorporated into a body wash, an after-shower body lotion, a shampoo, a conditioner, a soap, a gel, a hand sanitizer, a cream, a spray, a mousse, a lotion, an ointment, a powder, a stick, an injectable, an ingestable, a make-up product, a lip balm, a hair spray product, an arachnid/insect repellent, a cosmetic product, or a medicinal product.

10 Claims, No Drawings

(56) References Cited

U.S. PATENT DOCUMENTS

| | | |
|---|---|---|
| 5,770,556 A | 6/1998 | Farrell et al. |
| 5,785,979 A | 7/1998 | Wells |
| 5,849,273 A | 12/1998 | Bonda et al. |
| 5,876,755 A | 2/1999 | Perring et al. |
| 5,900,394 A | 5/1999 | Goel et al. |
| 5,904,917 A | 5/1999 | Mattai et al. |
| 5,914,101 A | 6/1999 | Tapley et al. |
| 5,948,416 A | 9/1999 | Wagner et al. |
| 5,955,409 A | 9/1999 | Farrell et al. |
| 5,989,529 A | 11/1999 | Kaplan |
| 5,989,536 A | 11/1999 | Deckner et al. |
| 6,024,942 A | 2/2000 | Tanner et al. |
| 6,043,204 A | 3/2000 | Kaufman et al. |
| 6,057,275 A | 5/2000 | Fair et al. |
| 6,074,630 A | 6/2000 | Devillez et al. |
| 6,096,697 A | 8/2000 | Wells |
| 6,110,888 A | 8/2000 | Lupo, Jr. et al. |
| 6,159,453 A | 12/2000 | Avnir et al. |
| 6,217,852 B1 | 4/2001 | Gildenberg et al. |
| 6,224,852 B1 | 5/2001 | Morgan et al. |
| 6,238,650 B1 | 5/2001 | Lapidot et al. |
| 6,248,364 B1 | 6/2001 | Sengupta et al. |
| 6,248,703 B1 | 6/2001 | Finucane et al. |
| 6,255,264 B1 | 7/2001 | Fleurot et al. |
| 6,303,149 B1 | 10/2001 | Magdassi et al. |
| 6,348,218 B1 | 2/2002 | Hed et al. |
| 6,362,146 B1 | 3/2002 | Macaulay |
| 6,391,287 B1 | 5/2002 | Baldo et al. |
| 6,395,269 B1 | 5/2002 | Fuller et al. |
| 6,399,045 B1 | 6/2002 | Morgan et al. |
| 6,412,658 B1 | 7/2002 | Bartholomew et al. |
| 6,436,375 B1 | 8/2002 | Lapidot et al. |
| 6,468,509 B2 | 10/2002 | Lapidot et al. |
| 6,471,975 B1 | 10/2002 | Banovetz et al. |
| 6,485,713 B1 | 11/2002 | Bonda et al. |
| 6,491,902 B2 | 12/2002 | Shefer et al. |
| 6,500,791 B2 | 12/2002 | Pereira et al. |
| 6,524,594 B1 | 2/2003 | Santora et al. |
| 6,555,095 B1 | 4/2003 | Garrison |
| 6,576,228 B1 | 6/2003 | Crookham et al. |
| 6,607,713 B1 | 8/2003 | Chodorowski et al. |
| 6,696,067 B2 | 2/2004 | Brandt et al. |
| 6,699,824 B1 | 3/2004 | Dawson et al. |
| 6,740,631 B2 | 5/2004 | Shefer et al. |
| 6,770,270 B2 | 8/2004 | Bonda |
| 6,825,161 B2 | 11/2004 | Shefer et al. |
| 6,855,335 B2 | 2/2005 | Seok et al. |
| 6,913,825 B2 | 7/2005 | Ostafin et al. |
| 6,998,113 B1 | 2/2006 | Traynor et al. |
| 7,001,592 B1 | 2/2006 | Traynor et al. |
| 7,025,952 B1 | 4/2006 | Traynor et al. |
| 7,037,513 B1 | 5/2006 | Traynor et al. |
| 7,053,034 B2 | 5/2006 | Shefer et al. |
| 7,074,747 B1 | 7/2006 | Lukenbach et al. |
| 7,098,032 B2 | 8/2006 | Trubetskoy et al. |
| 7,138,382 B2 | 11/2006 | Wolff et al. |
| 7,226,582 B2 | 6/2007 | Traynor et al. |
| 7,226,607 B2 | 6/2007 | Uchiyama et al. |
| 8,039,015 B2 | 10/2011 | Speaker |
| 2002/0028235 A1 | 3/2002 | Reed et al. |
| 2002/0034487 A1 | 3/2002 | Maubru et al. |
| 2002/0064541 A1 | 5/2002 | Lapidot et al. |
| 2002/0077256 A1 | 6/2002 | Niemiec et al. |
| 2002/0131939 A1 | 9/2002 | Djerassi et al. |
| 2002/0167404 A1 | 11/2002 | Jordan |
| 2003/0032593 A1 | 2/2003 | Wender et al. |
| 2003/0059382 A1 | 3/2003 | Brandt et al. |
| 2003/0059383 A1 | 3/2003 | SaNogueira et al. |
| 2003/0108580 A1 | 6/2003 | Hasenzahl et al. |
| 2003/0134761 A1 | 7/2003 | Sebillotte-Arnaud et al. |
| 2003/0147818 A1 | 8/2003 | Dubief et al. |
| 2003/0171230 A1 | 9/2003 | Shana'a et al. |
| 2003/0176303 A1 | 9/2003 | Niemiec et al. |
| 2003/0187665 A1 | 10/2003 | Boyd |
| 2004/0005278 A1 | 1/2004 | Reinhart et al. |
| 2004/0028709 A1 | 2/2004 | Dueva et al. |
| 2004/0047826 A1 | 3/2004 | Brown |
| 2004/0101498 A1 | 5/2004 | Koshti et al. |
| 2004/0120905 A1 | 6/2004 | Gall et al. |
| 2004/0167046 A1 | 8/2004 | Lukenbach et al. |
| 2004/0169298 A1 | 9/2004 | Fukasawa et al. |
| 2004/0234558 A1 | 11/2004 | O'Conner et al. |
| 2004/0247536 A1 | 12/2004 | Chaudhuri |
| 2004/0247543 A1 | 12/2004 | Huerta et al. |
| 2005/0065047 A1 | 3/2005 | Shefer et al. |
| 2005/0123611 A1 | 6/2005 | Barbe et al. |
| 2005/0255055 A1 | 11/2005 | Wagner et al. |
| 2006/0018966 A1 | 1/2006 | Lin et al. |
| 2006/0073106 A1 | 4/2006 | Berg-Schultz et al. |
| 2006/0135645 A1 | 6/2006 | Glassel et al. |
| 2007/0028400 A1 | 2/2007 | Wolber et al. |
| 2007/0292676 A1 | 12/2007 | Naigertsik et al. |
| 2008/0112904 A1 | 5/2008 | Traynor et al. |
| 2008/0317795 A1 | 12/2008 | Traynor et al. |
| 2009/0280149 A1 | 11/2009 | Tajima et al. |
| 2009/0324655 A1 | 12/2009 | Polonka et al. |
| 2010/0015188 A1 | 1/2010 | Izu et al. |
| 2010/0092410 A1 | 4/2010 | Cockerell et al. |
| 2010/0135936 A1 | 6/2010 | Dueva-Koganov et al. |
| 2010/0303940 A1* | 12/2010 | Enan ............... A01N 37/40 424/778 |
| 2011/0020253 A1 | 1/2011 | Doyle et al. |
| 2011/0150795 A1 | 6/2011 | Loing et al. |
| 2011/0206793 A1 | 8/2011 | Hines et al. |
| 2012/0141395 A1 | 6/2012 | Chaudhuri et al. |
| 2012/0148644 A1 | 6/2012 | Popplewell et al. |
| 2012/0207804 A1 | 8/2012 | Traynor et al. |
| 2014/0127275 A1 | 5/2014 | Cohen |
| 2014/0242131 A1 | 8/2014 | Cohen |
| 2014/0242132 A1 | 8/2014 | Cohen |
| 2014/0255456 A1 | 9/2014 | Cohen |
| 2015/0231046 A1 | 8/2015 | Cohen |
| 2016/0024441 A1* | 1/2016 | Cosgrove ............ C11D 3/3935 510/281 |
| 2016/0174552 A1* | 6/2016 | Goldblum ............ A01N 35/06 514/691 |
| 2017/0000697 A1 | 1/2017 | Cohen |
| 2017/0000698 A1 | 1/2017 | Cohen |
| 2017/0157021 A1* | 6/2017 | Traynor ............... A61K 8/895 |
| 2017/0216164 A1 | 8/2017 | Traynor et al. |
| 2017/0216165 A1 | 8/2017 | Traynor et al. |
| 2018/0042828 A1 | 2/2018 | Cohen |
| 2018/0042829 A1 | 2/2018 | Cohen |
| 2018/0055748 A1 | 3/2018 | Cohen |
| 2018/0125980 A1 | 5/2018 | Finley et al. |
| 2018/0263952 A1* | 9/2018 | Biro ................ A61K 9/0014 |
| 2020/0009040 A1* | 1/2020 | Peters ............... A61K 38/28 |

FOREIGN PATENT DOCUMENTS

| | | |
|---|---|---|
| EP | 0254447 B1 | 3/1993 |
| EP | 0399911 B1 | 7/1993 |
| EP | 1162942 | 6/2004 |
| WO | 1992016195 A1 | 10/1992 |
| WO | 199845036 A1 | 10/1998 |
| WO | 199943296 A2 | 11/1999 |
| WO | 200042985 A1 | 7/2000 |
| WO | 200057850 A1 | 10/2000 |
| WO | 2005009602 A2 | 2/2005 |
| WO | 2008144734 A1 | 11/2008 |
| WO | 2010000587 A2 | 1/2010 |
| WO | 2012074250 A2 | 6/2012 |
| WO | 2013087548 A2 | 6/2013 |
| WO | 2013107354 A1 | 7/2013 |
| WO | 2014074555 A1 | 5/2014 |
| WO | 2014132261 A2 | 9/2014 |
| WO | 2017139701 A1 | 8/2017 |

OTHER PUBLICATIONS

Donahue, Intellectual Property Licensing: A Crib Sheet for Deal Makers, http://teklaw.com/iplicens.htm (1998).

Donaldson, et al., Ultrafine Particles, Occup. Environ. Med., 58(3): 211-216 (2001).

(56) References Cited

OTHER PUBLICATIONS

Earth Supplied Products, Llc, ESP Kerabead™ Avo/Octo Encap Product Specification.
Earth Supplied Products, Llc, ESP Kerabead™ Shea Oil-20 Product Specification.
Earth Supplied Products, Llc, ESP Kerabead™ Silicone-20 Product Specification.
Earth Supplied Products, Llc, ESP Vegabead™ OMC 40 Product Specification.
EMD Chemicals Inc., Eusolex@ UV-Pearls™ Product Information.
EPO, Supplemental Search Report, dated Apr. 15, 2016.
Ford, Sunscreen How Products Are Made, Find Articles at BNET, vol. 2, (1994), Retrieved from http://www.findarticles.com.
Ghosh, Functional Coatings and Microencapsulation: A General Perspective, In Functional Coatings, pp. 1-28 (Wiley-VCH Verlag GmbH & Co KgaA, Weinheim) 2006.
Karr, et al., A Novel Encapsulation of N,N-diethyl-3-methylbenzamide (DEET) Facorably Modifies Skin Absorption while Maintaining Effective Evaporation Rates, J. Controlled Release 160:502-508 (2012).
Klykken, et al., Silicone Film-Forming Technologies for Health Care Applications, Dow Corning [online] (2009).
Merck KGaA, Eusolex® T-AVO, website description page (2005).
Merck KGaA, Eusolex® UV-Pearls™, website description page (2005).
PARSOL® 1789 Product Page.
PCT Form ISA 210, International Search Report, PCT/US2006/003365, dated May 24, 2006.
PCT Form ISA 237, Written Opinion, PCT/US2006/003365, dated May 24, 2006.
PCT Form ISA 210, International Search Report, PCT/US2013/068651, dated Mar. 5, 2014.
PCT Form ISA 237, Written Opinion, PCT/US2013/068651, dated Mar. 5, 2014.
PCT Form IB 373, International Preliminary Report on Patentability, PCT/US2013/068651, dated May 12, 2015.
PCT Form ISA 210, International Search Report, PCT/US2017/017556, dated Feb. 10, 2017.
PCT Form ISA 237, Written Opinion, PCT/US2017/017556, dated Feb. 10, 2017.
PCT Form ISA 210, International Search Report, PCT/US2018/017720, dated May 14, 2018.
PCT Form ISA 210, International Search Report, PCT/US2018/017722, dated Jun. 5, 2018.
PCT Form ISA 237, Written Opinion, PCT/US2018/017720, dated May 14, 2018.
PCT Form ISA 237, Written Opinion, PCT/US2018/017722, dated Jun. 5, 2018.
Sanar, website (2016).
Specos, et al., Microencapsulated Citronella Oil for Mosquito Repellent Finishing of Cotton Textiles, Trans. R. Soc. Trop. Med. Hyg. 104: 653-658 (2010).
UCLA Trademarks and Licensing, http://web.archive.org/web/20030811091818/http://www.asucla.ucla.edu/licensing/index.asp, Retrieved via Wayback Machine with archive date of Aug. 11, 2003.
Yeh, et al. Synthesis of Hollow Silica Spheres with Mesostructed Shell Using Cationic-Anionic-Neutral Block Copolymer Ternary Surfactants, Langmuier 22(1): 6-9 (2006).
Xiong, et al., Complex Coacervation of Ovalbumin-Carboxymethylcellulose Assessed by Isothermal Titration Calorimeter and Rheology: Effect of Ionic Strength and Charge Density of Polysaccharides, Food Hydrocolloids 73: 41-50 (2017).
Elsharif, Structure Odour Relationship Study of Acyclic Monoterpene Alcohols, Their Acetates and Synthesized Oxygenated Derivatives, Dissertation, pp. 99 (2017).
Mcpartland, Cannabis as Repellent and Pesticide, pp. 17 (1997).
PCT Form ISA 210, International Search Report, PCT/US2019/039632, dated Nov. 1, 2019.
PCT Form ISA 237, Written Opinion, PCT/US2019/039632, dated Nov. 1, 2019.

\* cited by examiner

COMPOSITIONS COMPRISING SILICON DIOXIDE-BASED PARTICLES INCLUDING ONE OR MORE AGENTS

This application claims the benefit of priority and the filing date pursuant to 35 U.S.C. § 119(e) to U.S. Provisional Patent Application Ser. No. 62/690,904, filed Jun. 27, 2018, the content of which is hereby incorporated by reference in its entirety.

Compositions comprising microcapsules enclosing one or more active agents for the purpose of controlling their release are known in the pharmaceutical, medical, cosmetics, and other industries. The microcapsules may additionally be surrounded by one or more active agents. Existing microcapsules tend to be rigid, such that application of mechanical force will cause the microcapsules to break, releasing the active agents contained there within. In the case of a cosmetic, therapeutic, or other products applied to the body, breakage of the microcapsules may reduce the effectiveness of the composition and release encapsulated active agents. The released active agents may thereafter be undesirably absorbed into the body (e.g., through the skin) or absorbed all at once where there is a need to absorb the active ingredients over a period of time. Further, once broken, existing microcapsules tend to more easily rinse off or have an oily or other unacceptable feel on the skin, hair, etc. In addition to the loss of coverage due to perspiration, absorption, and rinsing, existing encapsulation compositions also suffer from uneven application.

In spite prior attempts, there remains an unmet need for an effective encapsulated product that provides an effective means to apply an active agent to the body, particularly an encapsulated product that remains effective even after rinsing one or more times following application as well as having a gentle or acceptable feel on the human skin, as opposed to an oily feel. What is needed therefore is a microcapsule that is able to contain one or more active agents without substantial breakage or with controlled breakage over a period of time or through activity, and yet, has a gentle or acceptable feel on the human skin. The present invention addresses one or more of these needs by utilizing encapsulation technologies, milder surfactant systems, and good adhesive polymers that provide a strong binding capability, to provide more efficient deposition of the one or more active agents contained therein and/or therearound. The disclosed capsules also lay down on the skin surface in a manner that result in packing and spreading of the active agent over the skin surface or other portion of an individual. The disclosed capsules also provide a means for formulating various active agents that can result in a greater amount of active agent after application through such products as shampoo, body wash, conditioner, lotion, mousse, spray, hand sanitizer, cream and gel.

SUMMARY

Aspects of the present specification disclose compositions comprising one or more silicon dioxide-based particles. The disclosed silicon dioxide-based particles can be loaded with one or more active agents or unloaded. The disclosed active agents include, without limitation, a sunscreen agent, a photostabilizing agent, an analgesic agent, an aesthetic agent, an anti-acne agent, an anti-allergenic agent, an anti-angiogenic agent, a blood flow blocking agent, an anti-cellulite agent, an anti-inflammatory agent, an antioxidant, an anti-pruritic agent, an anti-skin aging agent, an anti-skin wrinkling agent, an anti-microbial agent, an anti-viral agent, a jellyfish repellent agent, a chelating agent, a deodorant, a dye, an essential oil, a hair growth promoter, a hair growth inhibitor, a hair bleaching agent, an anti-lice agent, an arachnid/insect repellent, a lipid, a medicinal agent, a moisturizing agent, a preservative, a silicone containing compound, a liquid hydrocarbon, a fragrance, a camouflage agent, a colorant, soothing agent, skin whitening agent, a skin nourishing agent, a structuring agent, a sunscreen agent, a sunless tanning agent, a thickening agent, or a vitamin, or any combination thereof. The disclosed compositions can further comprise one or more additional components. Additional components include, without limitation, a cationic polymer, a film former, a surfactant, a surfactant metal complex, a chelating agent, a preservative, and a thickening agent. A composition disclosed herein may be can be manufactured as or incorporated into a body wash, an after-shower body lotion, a shampoo, a conditioner, a soap, a gel, a hand sanitizer, a cream, a spray, a mousse, a lotion, an ointment, a powder, a stick, an injectable, an ingestable, a make-up product, a lip balm, a hair spray product, an arachnid/insect repellent, a cosmetic product, or a medicinal product. The present specification further discloses methods and uses for the disclosed compositions.

DETAILED DESCRIPTION

Silicon dioxide-based particles can be derived from siliceous rocks, that is, sedimentary rocks that have silica ($SiO_2$) as the principal constituent. The most common siliceous rock is chert. Other types which are useful in accordance with the teachings disclosed herein, includes, among others, diatomaceous earth (diatomite), are commonly formed from silica-secreting organisms such as radiolarians, diatoms, or some types of sponges. The typical chemical composition of oven-dried diatomaceous earth is about 80% to about 90% silica, with about 2% to about 4% alumina and about 0.5% to about 2% iron oxide. Diatomaceous earth can vary in constituents (silica, alumina and iron oxide, for example), percentages of constituents comprising the diatomaceous earth and/or both, from the example above.

The present specification encompasses compositions comprising one or more active agents contained in silicon dioxide-based particles. Silicon dioxide-based particles increases the stability of a composition by protecting the one or more agents contained therein. In addition, silicon dioxide-based particles increase the effectiveness of a composition by creating a layer that physically shields the skin surface and provides more complete and even coverage. Furthermore, silicon dioxide-based particles also minimize and/or controls the absorption of an agent disclosed herein into the dermis and subsequent systemic distribution in the body. Silicon dioxide-based particles can also serve the purpose of separating materials in particular formulations to avoid interaction of chemicals until needed. Silicon dioxide-based particles can also be provided so as to pick up oils, such as from a skin or hair surface, after being deposited thereto as part of the formulation of the composition provided in accordance with the teachings of the present disclosure. Furthermore, silicon dioxide-based particles do not convey an oiliness or greasiness, but instead providing a “smooth and silky” skin feel which adds to the aesthetics of a formulation disclosed herein.

Silicon dioxide-based particles disclosed herein facilitate tight packing on the surface of the skin to form a layer, prevents or minimizes breakage or rupture of the particles upon friction or other external force and/or enables the particles to have high load rates. For example, applications involving a non-encapsulated active agent is absorbed directly into the skin within about 1 hour. This is often undesirable or even detrimental because the benefits may be quickly lost, and repeated applications are required to maintain adequate coverage by the active agent. In addition, absorption of some active agents can be toxic to some degree and create health problems for the user if absorption rates are too high. Silicon dioxide-based particles, in one example comprising diatomaceous earth as herein disclosed and containing one or more active agents, form a layer on top of the skin surface that acts as a protective barrier. The particles enable dense packing to form a strong cohesive layer. Among other things, this layer acts like a shield to physically protect a skin surface from harmful environmental exposure, such as, e.g., sunlight, wind, dryness. In addition, since the active agents are contained in and by the particles, absorption into the skin is minimized. This layer can be maintained on the surface of skin for upwards of 8 or more hours.

In addition, silicon dioxide-based particles disclosed herein is designed so as to experience minimal or no leakage of the one or more active agents disclosed herein, or decomposition when applied to the skin. In particular embodiments, particles disclosed herein are eventually removed from the skin through repeated washing and/or normal sloughing of the external skin cell layers. Especially for agents used for one-time or very few exposures, such as can occur for personnel engaged in combating or containing terrorist attacks or in warfare, the particles provide a means to deliver a last line of defense on the skin of personnel where the one or more agents contained in and by the particles may be ones that are not appropriate for long-term use, but that are appropriate for a limited number of applications in order to protect the wearer from a greater risk (e.g., diatomaceous earth-based particles containing lead to protect against a radiation attack).

Further, the mechanical properties of silicon dioxide-based particles disclosed herein may be selected to provide an exfoliating effect by acting as an exfoliant in the composition. Exfoliant compounds act an abrasive for sloughing away the outermost layer of dead skin cells from the epidermis, which may smooth the skin, promote blood circulation, and/or increase the turnover of surface skin cells. At least some of the particles are composed of materials selected to be sufficiently hard to achieve removal of the dead skin through mechanical exfoliation (e.g., by scrubbing, etc.). In addition, the structural properties of silicon dioxide-based particles disclosed herein may be selected to provide physical support, such as, e.g., a dermal filler.

In an embodiment, silicon dioxide-based particles can be diatomaceous earth-based particles. Diatoms are unicellular microorganisms found world-wide in sea water, fresh water and soil. In the presence of adequate nutrients and sunlight, an assemblage of living diatoms doubles roughly every 8-24 hours by asexual reproduction (binary fission). A unique feature of diatom anatomy is that they are surrounded by a hard, porous cell wall made of silica (hydrated silicon dioxide), called a frustule or external skeleton. When a diatom dies, its organic parts disinigrate leaving the frustule, which is mined and refined into diatomaceous earth, called diatomite.

Diatomaceous earth-based particles include diatomaceous earth processed from diatoms harvest from nature, from a defined culture, or any combination therefrom. For example, diatomaceous earth-based particles can include materials based on intact and/or broken cell walls of diatoms, and includes, without limitation, food grade and non-food grade diatomaceous earth. Use of and preparation of diatomaceous earth in the pharmaceutical industry is known to persons skilled in the art; see for example U.S. Pat. No. 8,883,860 and U.S. Patent Application Publication US 2013/0149380, both herein incorporated by reference in their entirety. In addition, diatomaceous earth-based particles can include materials based on intact and/or broken cell walls of diatoms or a diatomaceous earth derivative (diatomite) cultured under controlled conditions. Such cultures are used to define the medium in which the diatoms grow and can influence which components are incorporated into the frustule (or external skeleton) of the diatoms that are the basis of the diatomaceous earth-based particles. Thus, growing diatoms is a culture medium high in metal oxides, like zinc oxide, results in frustules enriched for that metal. In these way, diatomaceous earth-based particles having more desirable properties, such as a higher cationic charge, can be produced and used as disclosed herein.

Silicon dioxide-based particles disclosed herein can range in any useful size. In a particular example, silicon dioxide-based particles range in size from about 100 nm to about 100 μm in mean diameter. In an embodiment, a particle disclosed herein has sufficient size to form a protective or desired layer on top of a skin surface after application of a composition disclosed herein. If capsules are too large, its size will reduce or disrupt the formation of a layer, thereby reducing the packing of silicon dioxide-based particles which in turn will reduce coverage on the skin or other part of the body. In aspects of this embodiment, a particle disclosed herein has a mean diameter of, e.g., at least 100 nm, at least 200 nm, at least 250 nm, at least 300 nm, at least 350 nm, at least 400 nm, at least 450 nm, at least 500 nm, at least 550 nm, at least 600 nm, at least 650 nm, at least 700 nm, at least 750 nm, at least 800 nm, at least 850 nm, at least 900 nm, at least 950 nm, at least 1 μm, at least 5 μm, at least 10 μm, at least 15 μm, at least 20 μm, at least 25 μm, at least 30 μm, at least 35 μm, at least 40 μm, at least 45 μm, at least 50 μm, at least 55 μm, at least 60 μm, at least 65 μm, at least 70 μm, at least 75 μm, at least 80 μm, at least 85 μm, at least 90 μm, at least 95 μm, or at least 100 μm. In other aspects of this embodiment, a diatomaceous earth-derived capsule has a diameter of, e.g., at most 200 nm, at most 250 nm, at most 300 nm, at most 350 nm, at most 400 nm, at most 450 nm, at most 500 nm, at most 550 nm, at most 600 nm, at most 650 nm, at most 700 nm, at most 750 nm, at most 800 nm, at most 850 nm, at most 900 nm, at most 950 nm, at most 1 μm, at most 5 μm, at most 10 μm, at most 15 μm, at most 20 μm, at most 25 μm, at most 30 μm, at most 35 μm, at most 40 μm, at most 45 μm, at most 50 μm, at most 55 μm, at most 60 μm, at most 65 μm, at most 70 μm, at most 75 μm, at most 80 μm, at most 85 μm, at most 90 μm, at most 95 μm, or at most 100 μm.

In aspects of this embodiment, a particle disclosed herein has a mean diameter of, e.g., about 100 nm to about 200 nm, about 100 nm to about 250 nm, about 100 nm to about 300 nm, about 100 nm to about 350 nm, about 100 nm to about 400 nm, about 100 nm to about 450 nm, about 100 nm to about 500 nm, about 100 nm to about 550 nm, about 100 nm to about 600 nm, about 100 nm to about 650 nm, about 100 nm to about 700 nm, about 100 nm to about 750 nm, about 100 nm to about 800 nm, about 100 nm to about 850 nm, about 100 nm to about 900 nm, about 100 nm to about 1 μm, about 100 nm to about 5 μm, about 100 nm to about 10 μm, about 100 nm to about 20 μm, about 100 nm to about 30 μm, about 100 nm to about 40 μm, about 100 nm to about 50 μm, about 200 nm to about 250 nm, about 200 nm to about 300 nm, about 200 nm to about 350 nm, about 200 nm to about 400 nm, about 200 nm to about 450 nm, about 200 nm to about 500 nm, about 200 nm to about 550 nm, about 200 nm to about 600 nm, about 200 nm to about 650 nm, about 200 nm to about 700 nm, about 200 nm to about 750 nm, about 200 nm to about 800 nm, about 200 nm to about 850 nm, about 200 nm to about 900 nm, about 200 nm to about 1 μm, about 200 nm to about 5 μm, about 200 nm to about 10 μm, about 200 nm to about 20 μm, about 200 nm to about 30 μm, about 200 nm to about 40 μm, about 200 nm to about 50 μm, about 250 nm to about 300 nm, about 250 nm to about 350 nm, about 250 nm to about 400 nm, about 250 nm to about 450 nm, about 250 nm to about 500 nm, about 250 nm to about 550 nm, about 250 nm to about 600 nm, about 250 nm to about 650 nm, about 250 nm to about 700 nm, about 250 nm to about 750 nm, about 250 nm to about 800 nm, about 250 nm to about 850 nm, about 250 nm to about 900 nm, about 250 nm to about 1 μm, about 250 nm to about 5 μm, about 250 nm to about 10 μm, about 250 nm to about 20 μm, about 250 nm to about 30 μm, about 250 nm to about 40 μm, about 250 nm to about 50 μm, about 300 nm to about 350 nm, about 300 nm to about 400 nm, about 300 nm to about 450 nm, about 300 nm to about 500 nm, about 300 nm to about 550 nm, about 300 nm to about 600 nm, about 300 nm to about 650 nm, about 300 nm to about 700 nm, about 300 nm to about 750 nm, about 300 nm to about 800 nm, about 300 nm to about 850 nm, about 300 nm to about 900 nm, about 300 nm to about 1 μm, about 300 nm to about 5 μm, about 300 nm to about 10 μm, about 300 nm to about 20 μm, about 300 nm to about 30 μm, about 300 nm to about 40 μm, about 300 nm to about 50 μm, about 350 nm to about 400 nm, about 350 nm to about 450 nm, about 350 nm to about 500 nm, about 350 nm to about 550 nm, about 350 nm to about 600 nm, about 350 nm to about 650 nm, about 350 nm to about 700 nm, about 350 nm to about 750 nm, about 350 nm to about 800 nm, about 350 nm to about 850 nm, about 350 nm to about 900 nm, about 350 nm to about 1 μm, about 350 nm to about 5 μm, about 350 nm to about 10 μm, about 350 nm to about 20 μm, about 350 nm to about 30 μm, about 350 nm to about 40 μm, about 350 nm to about 50 μm, about 400 nm to about 450 nm, about 400 nm to about 500 nm, about 400 nm to about 550 nm, about 400 nm to about 600 nm, about 400 nm to about 650 nm, about 400 nm to about 700 nm, about 400 nm to about 750 nm, about 400 nm to about 800 nm, about 400 nm to about 850 nm, about 400 nm to about 900 nm, about 400 nm to about 1 μm, about 400 nm to about 5 μm, about 400 nm to about 10 μm, about 400 nm to about 20 μm, about 400 nm to about 30 μm, about 400 nm to about 40 μm, about 400 nm to about 50 μm, about 450 nm to about 500 nm, about 450 nm to about 550 nm, about 450 nm to about 600 nm, about 450 nm to about 650 nm, about 450 nm to about 700 nm, about 450 nm to about 750 nm, about 450 nm to about 800 nm, about 450 nm to about 850 nm, about 450 nm to about 900 nm, about 450 nm to about 1 μm, about 450 nm to about 5 μm, about 450 nm to about 10 μm, about 450 nm to about 20 μm, about 450 nm to about 30 μm, about 450 nm to about 40 μm, about 450 nm to about 50 μm, about 500 nm to about 550 nm, about 500 nm to about 600 nm, about 500 nm to about 650 nm, about 500 nm to about 700 nm, about 500 nm to about 750 nm, about 500 nm to about 800 nm, about 500 nm to about 850 nm, about 500 nm to about 900 nm, about 500 nm to about 1 μm, about 500 nm to about 5 μm, about 500 nm to about 10 μm, about 500 nm to about 20 μm, about 500 nm to about 30 μm, about 500 nm to about 40 μm, about 500 nm to about 50 μm, about 550 nm to about 600 nm, about 550 nm to about 650 nm, about 550 nm to about 700 nm, about 550 nm to about 750 nm, about 550 nm to about 800 nm, about 550 nm to about 850 nm, about 550 nm to about 900 nm, about 550 nm to about 1 μm, about 550 nm to about 5 μm, about 550 nm to about 10 μm, about 550 nm to about 20 μm, about 550 nm to about 30 μm, about 550 nm to about 40 μm, about 550 nm to about 50 μm, about 600 nm to about 650 nm, about 600 nm to about 700 nm, about 600 nm to about 750 nm, about 600 nm to about 800 nm, about 600 nm to about 850 nm, about 600 nm to about 900 nm, about 600 nm to about 1 μm, about 600 nm to about 5 μm, about 600 nm to about 10 μm, about 600 nm to about 20 μm, about 600 nm to about 30 μm, about 600 nm to about 40 μm, about 600 nm to about 50 μm, about 650 nm to about 700 nm, about 650 nm to about 750 nm, about 650 nm to about 800 nm, about 650 nm to about 850 nm, about 650 nm to about 900 nm, about 650 nm to about 1 μm, about 650 nm to about 5 μm, about 650 nm to about 10 μm, about 650 nm to about 20 μm, about 650 nm to about 30 μm, about 650 nm to about 40 μm, about 650 nm to about 50 μm, about 700 nm to about 750 nm, about 700 nm to about 800 nm, about 700 nm to about 850 nm, about 700 nm to about 900 nm, about 700 nm to about 1 μm, about 700 nm to about 5 μm, about 700 nm to about 10 μm, about 700 nm to about 20 μm, about 700 nm to about 30 μm, about 700 nm to about 40 μm, about 700 nm to about 50 μm, about 750 nm to about 800 nm, about 750 nm to about 850 nm, about 750 nm to about 900 nm, about 750 nm to about 1 μm, about 750 nm to about 5 μm, about 750 nm to about 10 μm, about 750 nm to about 20 μm, about 750 nm to about 30 μm, about 750 nm to about 40 μm, or about 750 nm to about 50 μm.

In aspects of this embodiment, a particle disclosed herein has a mean diameter of, e.g., about 1 μm to about 5 μm, about 1 μm to about 10 μm, about 1 μm to about 15 μm, about 1 μm to about 20 μm, about 1 μm to about 25 μm, about 1 μm to about 30 μm, about 1 μm to about 35 μm, about 1 μm to about 40 μm, about 1 μm to about 45 μm, about 1 μm to about 50 μm, about 1 μm to about 60 μm, about 1 μm to about 70 μm, about 1 μm to about 80 μm, about 1 μm to about 90 μm, about 1 μm to about 100 μm, about 5 μm to about 10 μm, about 5 μm to about 15 μm, about 5 μm to about 20 μm, about 5 μm to about 25 μm, about 5 μm to about 30 μm, about 5 μm to about 35 μm, about 5 μm to about 40 μm, about 5 μm to about 45 μm, about 5 μm to about 50 μm, about 5 μm to about 60 μm, about 5 μm to about 70 μm, about 5 μm to about 80 μm, about 5 μm to about 90 μm, about 5 μm to about 100 μm, about 10 μm to about 15 μm, about 10 μm to about 20 μm, about 10 μm to about 25 μm, about 10 μm to about 30 μm, about 10 μm to about 35 μm, about 10 μm to about 40 μm, about 10 μm to about 45 μm, about 10 μm to about 50 μm, about 10 μm to about 60 μm, about 10 μm to about 70 μm, about 10 μm to about 80 μm, about 10 μm to about 90 μm, about 10 μm to about 100 μm, about 15 μm to about 20 μm, about 15 μm to about 25 μm, about 15 μm to about 30 μm, about 15 μm to about 35 μm, about 15 μm to about 40 μm, about 15 μm to about 45 μm, about 15 μm to about 50 μm, about 15 μm to about 60 μm, about 15 μm to about 70 μm, about 15 μm to about 80 μm, about 15 μm to about 90 μm, about 15 μm to about 100 μm, about 20 μm to about 25 μm, about 20 μm to about 30 μm, about 20 μm to about 35 μm, about 20 μm to about 40 μm, about 20 μm to about 45 μm, about 20 μm to about 50 μm, about 20 μm to about 60 μm, about 20 μm to about 70 μm, about 20 μm to about 80 μm, about 20 μm to about 90 μm, about 20 μm to about 100 μm, about 25 μm to about 30 μm, about 25 μm to about 35 μm, about 25 μm to about 40 μm, about 25 μm to about 45 μm, about 25 μm to about 50 μm, about 25 μm to about 60 μm, about 25 μm to about 70 μm, about 25 μm to about 80 μm, about 25 μm to about 90 μm, about 25 μm to about 100 μm, about 30 µm to about 35 µm, about 30 µm to about 40 µm, about 30 µm to about 45 µm, about 30 µm to about 50 µm, about 30 µm to about 60 µm, about 30 µm to about 70 µm, about 30 µm to about 80 µm, about 30 µm to about 90 µm, about 30 µm to about 100 µm, about 35 µm to about 40 µm, about 35 µm to about 45 µm, about 35 µm to about 50 µm, about 35 µm to about 60 µm, about 35 µm to about 70 µm, about 35 µm to about 80 µm, about 35 µm to about 90 µm, about 35 µm to about 100 µm, about 40 µm to about 45 µm, about 40 µm to about 50 µm, about 40 µm to about 60 µm, about 40 µm to about 70 µm, about 40 µm to about 80 µm, about 40 µm to about 90 µm, about 40 µm to about 100 µm, about 50 µm to about 60 µm, about 50 µm to about 70 µm, about 50 µm to about 80 µm, about 50 µm to about 90 µm, about 50 µm to about 100 µm, about 60 µm to about 70 µm, about 60 µm to about 80 µm, about 60 µm to about 90 µm, about 60 µm to about 100 µm, about 70 µm to about 80 µm, about 70 µm to about 90 µm, about 70 µm to about 100 µm, about 80 µm to about 90 µm, about 80 µm to about 100 µm, or about 90 µm to about 100 µm.

In an embodiment, silicon dioxide-based particles disclosed herein form one layer on a skin surface after application. In another embodiment, silicon dioxide-based particles disclosed herein form multiple layers on a skin surface after application. In aspects of this embodiment, silicon dioxide-based particles disclosed herein form two or more layers, three or more layers, four or more layers, or five or more layers on a skin surface after application.

In an embodiment, silicon dioxide-based particles disclosed herein such as, e.g., diatomaceous earth-derived particles, facilitate increased packing density which enables increased film density of a composition disclosed herein when applied to a surface. Density is determined by the weight of the one or more active agent comprising a film layer. Silicon dioxide-based particles disclosed herein can achieve greater packing density because the porous nature of these particles significantly reduce its weight. As such, silicon dioxide-based particles disclosed herein weight less than polymer-based capsules and are less dense that an active agent disclosed herein. Thus, the use of silicon dioxide-based particles disclosed herein enables the increase in the thickness of a film layer while decreasing its weight. This allows for a thicker film density to be applied to a skin surface without sacrificing the feel and appearance of a composition disclosed herein which in turn increases UV absorption and scattering.

In an embodiment, silicon dioxide-based particles disclosed herein prevent or retard the one or more active agents contained therein from being absorbed or otherwise penetrate, or minimize such absorption/penetration, into the epidermal layer of the skin. In an embodiment, silicon dioxide-based particles disclosed herein prevent or retard the one or more active agents contained therein from being absorbed or otherwise penetrate through the epidermal layer of the skin. In aspects of this embodiment, silicon dioxide-based particles disclosed herein prevent or retard the one or more active agents contained therein from being substantially absorbed or otherwise penetrate through the stratum corneum into the living epidermal layer of the skin. In aspects of this embodiment, silicon dioxide-based particles disclosed herein is designed to have only, e.g., at most 1%, at most 5%, at most 10%, at most 15%, at most 20% or at most 25% of the one or more active agents absorbed or otherwise penetrate through the stratum corneum into the live epidermal layer of the skin.

In aspects of this embodiment, one or more active agents disclosed herein may be absorbed or otherwise penetrate the epidermal layer of the skin by only, e.g., about 0.1 µm, about 0.5 µm, about 1 µm, about 5 µm, about 10 µm, about 15 µm, about 20 µm, about 30 µm, about 40 µm, about 50 µm, about 60 µm, about 70 µm, about 80 µm, about 90 µm or about 100 µm. In other aspects of this embodiment, one or more active agents disclosed herein may be absorbed or otherwise penetrate the epidermal layer of the skin by only, e.g., at most about 0.1 µm, at most 0.5 µm, at most 1 µm, at most 5 µm, at most 10 µm, at most 15 µm, at most 20 µm, at most 30 µm, at most 40 µm, at most 50 µm, at most 60 µm, at most 70 µm, at most 80 µm, at most 90 µm or at most 100 µm. In yet other aspects of this embodiment, one or more active agents disclosed herein may be absorbed or otherwise penetrate the epidermal layer of the skin by only, e.g., about 0.1 mm to about 1 µm, about 0.1 mm to about 5 µm, about 0.1 mm to about 10 µm, about 0.1 mm to about 15 µm, about 0.1 mm to about 20 µm, about 0.1 mm to about 25 µm, about 0.1 mm to about 30 µm, about 0.1 mm to about 40 µm, about 0.1 mm to about 50 µm, about 0.1 mm to about 60 µm, about 0.1 mm to about 70 µm, about 0.1 mm to about 80 µm, about 0.1 mm to about 90 µm, about 0.1 mm to about 100 µm, about 0.5 mm to about 1 µm, about 0.5 mm to about 5 µm, about 0.5 mm to about 10 µm, about 0.5 mm to about 15 µm, about 0.5 mm to about 20 µm, about 0.5 mm to about 25 µm, about 0.5 mm to about 30 µm, about 0.5 mm to about 40 µm, about 0.5 mm to about 50 µm, about 0.5 mm to about 60 µm, about 0.5 mm to about 70 µm, about 0.5 mm to about 80 µm, about 0.5 mm to about 90 µm, about 0.5 mm to about 100 µm, about 1 mm to about 5 µm, about 1 mm to about 10 µm, about 1 mm to about 15 µm, about 1 mm to about 20 µm, about 1 mm to about 25 µm, about 1 mm to about 30 µm, about 1 mm to about 40 µm, about 1 mm to about 50 µm, about 1 mm to about 60 µm, about 1 mm to about 70 µm, about 1 mm to about 80 µm, about 1 mm to about 90 µm, about 1 mm to about 100 µm, about 5 mm to about 10 µm, about 5 mm to about 15 µm, about 5 mm to about 20 µm, about 5 mm to about 25 µm, about 5 mm to about 30 µm, about 5 mm to about 40 µm, about 5 mm to about 50 µm, about 5 mm to about 60 µm, about 5 mm to about 70 µm, about 5 mm to about 80 µm, about 5 mm to about 90 µm, about 5 mm to about 100 µm, about 10 mm to about 15 µm, about 10 mm to about 20 µm, about 10 mm to about 25 µm, about 10 mm to about 30 µm, about 10 mm to about 40 µm, about 10 mm to about 50 µm, about 10 mm to about 60 µm, about 10 mm to about 70 µm, about 10 mm to about 80 µm, about 10 mm to about 90 µm or about 10 mm to about 100 µm.

Silicon dioxide-based particles disclosed herein may be designed to be stable or unstable. Stability includes mechanical stability as well as photostability (providing stabilization of photosensitive drugs). Mechanical stability refers to the degree of particle breakage or disintegration following exposure to physical forces. Photostability refers to the degree of particle breakage or disintegration following exposure to the sun or UV radiation. Upon breakage of a silicon dioxide-based particle its internal contents, including, the one or more active agents disclosed herein are released onto a skin surface.

In an embodiment, silicon dioxide-based particles disclosed herein are prepared so to experience no or minimal breakage when applied to a skin surface. In another embodiment, silicon dioxide-based particles disclosed herein is prepared so to experience various degrees of breakage, on average, when applied to a skin. In an aspect of this embodiment, silicon dioxide-based particles disclosed herein is formulated so as to break open in response to conditions that occur on a skin surface, so that after application the particles act to release their contents in a time-release or controlled manner. For example, skin or hair conditions can vary with the user's environment, a variation which can trigger breakage of capsules, include, without limitation, dryness of the skin surface, dryness of hair, pH, temperature, friction, exposure to light and/or exposure to air.

In an embodiment, silicon dioxide-based particles disclosed herein may be prepared so as to experience about 0% breakage, or breakage in a range of from about 1% to about 100%. In aspects of this embodiment, silicon dioxide-based particles disclosed herein may be prepared so as to experience breakage of, e.g., at least 10%, at least 20%, at least 30%, at least 40%, at least 50%, at least 60%, at least 70, at least 80%, at least 90%, or at least 95% after application to a skin surface. In other aspects of this embodiment, silicon dioxide-based particles disclosed herein may be prepared so as to experience breakage of, e.g., at most 10%, at most 20%, at most 30%, at most 40%, at most 50%, at most 60%, at most 70, at most 80%, at most 90%, or at most 95% after application to a skin surface. In yet other aspects of this embodiment, silicon dioxide-based particles disclosed herein may be prepared so as to experience breakage in a range of, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% after application to a skin surface.

Silicon dioxide-based particles, such as, e.g., diatomaceous earth-derived particles, can absorb up to 200% of their weight, and as such, can be loaded, absorbed, trapped or otherwise caused to contained one or more agents, such as, e.g., one or more active agents disclosed herein. Silicon dioxide-based particles, such as, e.g., diatomaceous earth-derived particles, are slightly negatively charged which allows then to be dispersed in aqueous environments without or very little need for an emulsifier. Hydrophobic active agents like oils including sunscreens are generally absorbed at approximately 80 mL/g up to 250 mL/g over time. The larger a silicon dioxide-based particle, such as, e.g., diatomaceous earth-derived particle, the greater the loading weight.

In one embodiment, silicon dioxide-based particles, like diatomaceous earth-derived particles, can be mixed with a solution comprising one or more agents which are absorbed or loaded by simple diffusion or capillary action into the non-polar interior of the particles. Depending on the viscosity of the solution, the temperature of the loading reaction can be increased and/or an appropriate polar or non-polar solvent could be added to decrease the viscosity of the solution, thereby facilitating loading of one or more agents into the particles. In aspects of this embodiment, one or more hydrophobic active agents are mixed together with a core modifier and heated to about 50° C. to about 80° C. to form a solution. Silicon dioxide-based particles, like diatomaceous earth-derived particles, are then mixed with this active agent solution and incubated for about 1 hour to about 24 hours to allow the active agent solution to absorb into the particles.

In another embodiment, silicon dioxide-based particles, like diatomaceous earth-derived particles, can absorb an emulsion comprising one or more agents. In aspects of this embodiment, one or more hydrophilic active agents, one or more low HLB emulsifiers (HLB 4-9) and mixed in an aqeuous dispersion phase and added to a continuous phase comprising oil to form a water in oil emulsion. Silicon dioxide-based particles, like diatomaceous earth-derived particles, are then mixed with this active agent emulsion and incubated for about 1 hour to about 24 hours to allow the active agent emulsion to absorb into the particles. Depending on the one or more active agents, high HLB emulsifiers (HLB 11-16) can be uses instead of low HLB emulsifiers or a combination of low and high HLB emulsifiers can be used.

In all the embodiments above, silicon dioxide-based particles, such as, e.g., diatomaceous earth-derived particles, can be treated with neutralizing or charging agents, such as neutralizing or charging polymers, which facilitate uptake of the one or more agents, perhaps by altering the interior charge of the particles. For example, silicon dioxide-based particles, such as, e.g., diatomaceous earth-derived particles, can be treated with an agent that confers a negative charge to the interior of the particles, thereby facilitating uptake of positively charged agents. Examples of such anionic modifiers include amphoterics and acrylates including ethylene/sodium acrylate copolymers. As another example, silicon dioxide-based particles, such as, e.g., diatomaceous earth-derived particles, can be treated with an agent that confers a positive charge to the interior of the particles, thereby facilitating uptake of negatively charged agents. Examples of such cationic modifiers include polyquaterniums as disclosed herein. Likewise, silicon dioxide-based particles, such as, e.g., diatomaceous earth-derived particles, can be treated with an agent that confers a hydrophobicity to the interior of the particles, thereby facilitating uptake of hydrophobic agents. Silicon dioxide-based particles, such as, e.g., diatomaceous earth-derived particles, can also be treated with an agent that confers a higher melting point and/or non-polar material to slow down the rate of volatilization and diffusion of fragrances or other volatiles.

In all the embodiments above, the amount of silicon dioxide-based particles, like diatomaceous earth-derived particles added will depend in part on the desired viscosity of the resulting slurry. For example, about 25% to 50% by total weight of silicon dioxide-based particles, like diatomaceous earth-derived particles are added to produce a slurry useful in formulating a lotion, shampoo, body wash or other more liquid-type formulations, For sticks, lip balm or other more solid-type formulations up to 80% by total weight of silicon dioxide-based particles, like diatomaceous earth-derived particles can be added. The resulting slurry can then be formulated into a finished composition as disclosed herein.

In an embodiment, silicon dioxide-based particles, like diatomaceous earth-derived particles, loaded with one or more agents are not treated in a manner that retards the release or completely entraps the one or more agents loaded therein. The structural and physical properties of silicon dioxide-based particles, like diatomaceous earth-derived particles, reduce the evaporation rate of an active agent.

In an embodiment, silicon dioxide-based particles, like diatomaceous earth-derived particles, loaded with one or more agents are treated in a manner that retards the release or completely entraps the one or more agents loaded therein. For example, one or more core modifiers can be added to an active agent mixture during an absorption or loading process as disclosed herein. Alternatively, silicon dioxide-based particles, like diatomaceous earth-derived particles already loaded with one or more active agents can be subsequently treated with one or more core modifiers that loads the core modifiers into the particles, coats the surface of the particles, or both. Such treatment slows the rate of evaporation of the one or more active agents enabling for a controlled release of the active agents or the complete entrapment of the active agents within the particles. Examples of core modifiers include, without limitation, polyesters, hydrophobically modified acrylates/cellulosics, polyolefin, polyamides including polyamine 3, fatty alcohols including cetearyl alcohol and ceteareth phosphate, fatty acids including stearic acid, salts of fatty acids including sodium stearate, natural waxes including beeswax, mulberry wax, carnauba wax and soybean wax, synthetic waxes and naturally derived ethoxylates.

In aspects of this embodiment, silicon dioxide-based particles, like diatomaceous earth-derived particles decrease the evaporation rate of one or more active agents by, e.g., about 1-fold, about 2-fold, about 3-fold, about 4-fold, about 5-fold, about 6-fold, about 7-fold, about 8-fold, about 9-fold, or about 10-fold relative to the one or more active agents in an unencapsulated form. In other aspects of this embodiment, silicon dioxide-based particles, like diatomaceous earth-derived particles decrease the evaporation rate of one or more active agents by, e.g., at least 1-fold, at least 2-fold, at least 3-fold, at least 4-fold, at least 5-fold, at least 6-fold, at least 7-fold, at least 8-fold, at least 9-fold, or at least 10-fold relative to the one or more active agents in an unencapsulated form. In yet other aspects of this embodiment, silicon dioxide-based particles, like diatomaceous earth-derived particles decrease the evaporation rate of one or more active agents by, e.g., at most 1-fold, at most 2-fold, at most 3-fold, at most 4-fold, at most 5-fold, at most 6-fold, at most 7-fold, at most 8-fold, at most 9-fold, or at most 10-fold relative to the one or more active agents in an unencapsulated form. In still other aspects of this embodiment, silicon dioxide-based particles, like diatomaceous earth-derived particles decrease the evaporation rate of one or more active agents by, e.g., about 1-fold to about 2-fold, about 1-fold to about 3-fold, about 1-fold to about 4-fold, about 1-fold to about 5-fold, about 1-fold to about 6-fold, about 1-fold to about 7-fold, about 1-fold to about 8-fold, about 1-fold to about 9-fold, about 1-fold to about 10-fold, about 2-fold to about 3-fold, about 2-fold to about 4-fold, about 2-fold to about 5-fold, about 2-fold to about 6-fold, about 2-fold to about 7-fold, about 2-fold to about 8-fold, about 2-fold to about 9-fold, about 2-fold to about 10-fold, about 3-fold to about 4-fold, about 3-fold to about 5-fold, about 3-fold to about 6-fold, about 3-fold to about 7-fold, about 3-fold to about 8-fold, about 3-fold to about 9-fold, about 3-fold to about 10-fold, about 4-fold to about 5-fold, about 4-fold to about 6-fold, about 4-fold to about 7-fold, about 4-fold to about 8-fold, about 4-fold to about 9-fold, about 4-fold to about 10-fold, about 5-fold to about 6-fold, about 5-fold to about 7-fold, about 5-fold to about 8-fold, about 5-fold to about 9-fold, about 5-fold to about 10-fold, about 6-fold to about 7-fold, about 6-fold to about 8-fold, about 6-fold to about 9-fold, about 6-fold to about 10-fold, about 7-fold to about 8-fold, about 7-fold to about 9-fold, about 7-fold to about 10-fold, about 8-fold to about 9-fold, about 8-fold to about 10-fold, or about 9-fold to about 10-fold, relative to the one or more active agents in an unecapsulated form.

In an embodiment, silicon dioxide-based particles, like diatomaceous earth-derived particles, loaded with one or more agents can be treated in a manner that retards the release or completely entraps the one or more agents loaded therein. In one embodiment, the solution comprising the one or more agents can further include a wax or a polymer, including a plastic that acts as a core stabilizer which upon loading into the silicon dioxide-based particles, like diatomaceous earth-derived particles, retards or prevents the release of the one or more agents therein. In one embodiment, loaded silicon dioxide-based particles, like diatomaceous earth-derived particles, can be formulated in the presence of other viscous components, like a wax or a polymer, including a plastic, which acts as a mechanical barrier to retard or prevent the release of the one or more agents therein. In another embodiment, loaded silicon dioxide-based particles, like diatomaceous earth-derived particles, can be coated with a material, like a wax or a polymer, including a plastic, that seals the openings of the particles, thereby retarding or preventing the release of the one or more agents loaded therein. In one embodiment, the coating reaction of silicon dioxide-based particles, like diatomaceous earth-derived particles, can in addition to, or in lieu of, be neutralize or charge the surface of the particles to facilitate its subsequent formulation. For example, silicon dioxide-based particles, like diatomaceous earth-derived particles, can be coated with a neutralizing agent that facilitates formulation with hydrophobic components. Likewise, silicon dioxide-based particles, like diatomaceous earth-derived particles, can be coated with a polar agent that facilitates formulation with hydrophilic components. Silicon dioxide-based particles, like diatomaceous earth-derived particles, can be coated using standard procedures known in the art including vaporing, fuming, spraying, emulsion, soaking or any other process that coasts the particles as desired. Non-limiting examples of useful coating agents include polyquaterniums, acrylates and water-soluable silicones.

A composition disclosed herein comprising silicon dioxide-based particles, such as, e.g., diatomaceous earth-derived particles, comprise one or more active agents. An active agent disclosed herein includes, without limitation, a sunscreen agent, a photostabilizing agent, a moisturizing agent, an arachnid/insect repellent, an analgesic agent, an aesthetic agent, an anti-acne agent, an anti-allergenic agent, an anti-angiogenic agent, a blood flow blocking agent, an anti-cellulite agent, an anti-inflammatory agent, an antioxidant, an anti-pruritic agent, an anti-skin aging agent, an anti-skin wrinkling agent, an anti-microbial agent (e.g., anti-fungals, anti-bacterials, anti-parasitics, and anti-virals), a jellyfish repellent agent, a deodorant, a dye, an essential oil, a hair growth promoter, a hair growth inhibitor, a hair bleaching agent, an anti-lice agent, a lipid, a medicinal agent (e.g., a biologic, a pharmaceutically active ingredient), a pest repellent, a silicone containing compound, a liquid hydrocarbon, a fragrance, a camouflage agent, a colorant, soothing agent (e.g. a cooling agent or a heating agent), skin whitening agent (e.g., a skin bleaching agent and a skin lightening agent), a skin nourishing agent, a structuring agent, a sunless tanning agent, a vitamin, (e.g., skin rash, skin disease and dermatitis medications) or other molecule useful in protecting, moisturizing, shielding or otherwise enhancing the health and appearance of an individual.

Aspects of the present specification disclose a sunscreen agent. A sunscreen agent is an ultraviolet (UV) ray-blocking compound that absorbs, blocks and/or reflects UV radiation. A sunscreen agent disclosed herein absorbs, blocks and/or reflects UV radiation given off by a natural source, such as, e.g., sunlight, and/or man-made source, such as, e.g., a fluorescent light bulb. In an aspect of this embodiment, a sunscreen agent exhibits absorptive and/or reflective properties within the wavelength region of between about 290 to about 420 nm. Any sunscreen agent known in the art or apparent to a skilled artisan may be used. A sunscreen agent disclosed herein may be an organic molecule or inorganic molecule. In addition, a sunscreen agent may be a UVA absorber, a UVA blocker, a UVA reflector, a UVB absorber, a UVB blocker, a UVB reflector, a broad-spectrum UVA and UVB absorber, a broad-spectrum UVA and UVB blocker, a broad-spectrum UVA and UVB reflector, a physical blocker, a physical reflector, or any combination thereof. A UVA absorber can be a UVA I absorber and/or UVA II absorber.

Sunscreen agents commonly contain one or more of the following ingredients: 1) a chemical sunscreen agent, typically an organic compound that absorb UV light; 2) a physical sunscreen agent, typically an inorganic particulates that reflect, scatter, and absorb UV light; and 3) a hybrid sunscreen agent, typically an organic particulate that absorbs UV light like an organic chemical compound, but also contain multiple chromophores that may reflect and scatter UV light like an inorganic particulate.

Organic sunscreen agents can be grouped based upon their chemical structure. Such groups include, without limitation: 1) a para-amino benzoate or derivative or salt thereof; 2) a salicylate or derivative or salt thereof; 3) a cinnamate or derivative or salt thereof; 4) a benzophenone or derivative or salt thereof; 5) an anthranilate or derivative or salt thereof; 6) dibenzoylmethane or derivative or salt thereof; 7) a camphor or derivative or salt thereof; 8) a naphtholsulfonate or derivative or salt thereof; 9) a coumarin or derivative or salt thereof; 10) a diazole or derivative or salt thereof; 11) a biphenyldisulfonate or derivative or salt thereof; 12) a hydrocarbon or derivative or salt thereof; 13) a quinolone or derivative or salt thereof; 14) a quinine salt; 15) a miscellaneous organic sunscreen agent.

A para-amino benzoate derivative includes, without limitation, ethylbenzoic acid, isobutylbenzoic acid, benzoic acid glyceryl ester, p-dimethylaminobenzoic acid or a salt thereof.

A salicylate derivative includes, without limitation, amyl salicylate, phenyl salicylate, benzyl salicylate, menthy salicylate, octyl salicylate (2-ethylhexyl salicylate, glyceryl salicylate, a salicylate dipropylene glycol ester or a salt thereof.

A cinnamate derivative includes, without limitation, cinnamic acid derivative, such as, e.g., methyl cinnamic ester and benzyl cinnamic ester, alpha-phenyl or cinnamonitrile; a butyl cinnamoyl pyruvate; a dihydroxycinnamic acid derivatives, such as, e.g., umbelliferone, methylumbelliferone, or methylaceto-umbelliferone; a trihydroxycinnamic acid derivative, such as, e.g., esculetin, methylesculetin, daphnetin, a glucoside, such as, e.g., esculin and daphnin; octyl methoxycinnamate (Octinoxate); and a p-methoxycinnamic acid ester, such as, e.g., amyl p-methoxycinnamate, 2-ethylhexyl p-methoxycinnamate, 2-ethoxyethyl p-methoxycinnamate, diethanolamine p-methoxycinnamate, n-octyl p-methoxycinnamate (ethyl hexyl methoxycinnamate PARASOL MCX), isoamyl p-methoxycinnamate and propyl p-methoxycinnamate or a salt thereof.

A benzophenone derivative includes, without limitation, a hydroxyl-substituted benzophenone, a methoxy-substituted benzophenone, Oxybenzene (also called benzophenone-3 or 2-Hydroxy4-Methoxybenzophenone), Sulisobenzone (also called benzophenone-4), Dioxybenzone, Benzoresorcinol, 2,2',4,4'-Tetrahydroxybenzophenone, 2,2'-Dihydroxy4,4'-dimethoxpenzophenone, Octabenzone, 4-Isopropyhldibenzoylmethane or a salt thereof.

An anthranilate derivative includes, without limitation, o-aminobenzoate; methyl anthranilate, menthyl anthranilate, phenyl anthranilate, benzyl anthranilate, phenylethyl anthranilate, linalyl anthranilate, terpinyl anthranilate, ethyl-[bis(hydroxypropyl)]aminobenzoate, glyceryl aminobenzoate, a cyclohexenyl anthranilate ester or a salt thereof.

A dibenzoylmethane derivative includes, without limitation, Avobenzone (also called butylmethoxydibenzoylmethane, 4-tert-Butyl-4'-methoxydibenzoylmethane or PARASOL 1789), 4-isopropyl-di-benzoylmethane or a salt thereof.

A camphor derivative includes, without limitation, camphor benzalkonium methosulfate, terephthalidene dicamphor sulfonic acid, benzylidene camphor sulfonic acid, polyacrylamidomethyl benzylidene camphor, 4-methylbenzylidene camphor, 3-benzylidene camphor, terephthalylidene dicamphor sulfonic acid or a salt thereof.

A naphtholsulfonate derivative includes, without limitation, 2-naphthol-3,3-disulfonic, 2-naphthol-6,8-disulfonic acid or a salt thereof. A coumarin derivative includes, without limitation, 7-hydroxy coumarin, 7-methyl coumarin, 3-phenlyll coumarin or a salt thereof. A diazole derivative includes, without limitation, 2-acetyl-3-bromoindazole, phenyl benzoxazole, methyl naphthoxalole, an aryl benzothiazole or a salt thereof.

A biphenyldisulfonate derivative includes, without limitation, o-hydroxybiphenyldisulfonate, p-hydroxybiphenyldisulfonate or a salt thereof. A hydrocarbon derivative includes, without limitation, diphenylbutadiene, stilbene or a salt thereof. A quinoline derivative includes, without limitation, 8-hydroxyquinoline salts, 2-phenylquinoline or a salt thereof. A quinine salt includes, without limitation, bisulfate, sulfate, chloride, oleate, and tannate.

A miscellaneous organic sunscreen agent includes, without limitation, octocrylene (2-ethylhexyl 2-cyano-3,3-diphenylacrylate), digalloyl trioleate, etocrylene, dibenzylideneacetone (or dibenzalacetone), dihydroxyacetone, benzalacetophenone, dihydroxynaphthoic acid, disodium phenyl dibenzimidazole tetrasulfon, butyl carbityl (6-propyl piperonyl) ether, hydroquinone, a hexaethylether, tannic acid, uric acid and vilouric acid.

Many organic and inorganic compounds can contain organic and inorganic molecules which exhibit absorption, refractive or both properties as a property of the said above and as an example can be synthesized on a surfactant, to exhibit UV absorption characteristics and furthermore be classified without being a UV absorber recognized in the current monograph.

An inorganic sunscreen agent includes, without limitation, a metal oxide, a metal alkoxide and a polymer. Non-limiting examples of a metal oxide include an iron oxide, a titanium dioxide and a zinc oxide (e.g., Z-COTE™ HP 1, SkinCeuticals). A polymer includes, without limitation, a polyethylene polymer, a polyamide polymer and a silicone polymer. A silicone polymer includes long-chain silicone polymer linked with chromophore. For example, benzyl malonate chromophores attached to specific points on a polysiloxane chain (PARASOL SLX).

A metal oxide, either alone or in combination with other sunscreen agents disclosed herein, can have an anatase, rutile, or amorphous structure. Metal oxide particles can be uncoated or coated with a variety of materials including, without limitation, aluminium compounds such as aluminium oxide, aluminium stearate, aluminium laurate and the like; phospholipids such as lecithin; silicone compounds; and mixtures thereof. Various grades and forms of metal oxides are described in CTFA Cosmetic Ingredient Dictionary, Third Edition (1982), U.S. Pat. No. 4,820,508; and PCT Patent Application WO 1990/011067; each of which is hereby incorporated by reference in its entirety. Suitable grades of metal oxides for use in a composition disclosed herein can be purchased from commercial suppliers, including, without limitation, the MT micronized series from Tri-K Industries (Emerson, N.J.). In one non-limiting example, an inorganic molecule, like a metal oxide, can be placed into an oil, such as an olive or other plant derived oil, for example in addition to a dispersing agent such as a non-surface-active polymer or a surface-active substance added to the suspension and vortexed to provide a suspension having about 50 to 200 nm sized droplets for loading into the silicon dioxide-based particles, such as, e.g., diatomaceous earth-derived particles, of the instant disclosure. Exemplary dispersing agents include, but are not limited to, polyhydroxystearic acid and benzoid alkyl sulfonic acid.

Micronized metal oxide compounds generally have a mean particle size ranging from about 10 nm to about 50 nm. For example, the titanium dioxide has a mean particle size of about 15 nm and this sunscreen agent is available under the trade designation T-AVO (silica-coated titanium dioxide), MT-100F (modified with stearic acid and iron hydroxide), MT-100S (treated with lauric acid and aluminium hydroxide) and MT-100T (coated with stearic acid and aluminium compounds). Uncoated titanium dioxide compounds have a mean particle size of about 35 nm to about 50 nm are available under the trade designations MT-500B, MT-600B, MT-15OW, respectively. Mixtures of two or more types and particle size variations of metal oxide compounds can be used in a composition disclosed herein. In a further embodiment, metal oxide compounds include, without limitation, Tioveil (Tioxide Group), 40% dispersions of surface-treated titanium dioxide in a range of cosmetic vehicles and Spectraveil (Tioxide Group), 60% dispersions of zinc oxide in a range of cosmetic vehicles.

A sunscreen agent can be a UVA sunscreen agent, a UVB sunscreen agent, or a UVA/UVB or "broad-spectrum" sunscreen agent. A UVA sunscreen agent exhibits absorptive, blocking and/or reflective properties within the wavelength region of between about 290 nm to about 320 nm. A UVA sunscreen agent exhibits absorptive, blocking and/or reflective properties within the wavelength region of between about 320 nm to about 420 nm. A broad-spectrum UVA/UVB sunscreen agent exhibits absorptive, blocking and/or reflective properties within the wavelength region of between about 290 to about 420 nm. Non-limiting examples of a UVA sunscreen agent include Avobenzone (butyl methoxydibenzoylmethane or Parsol 1789), bisdisulizole disodium (Neo Heliopan AP), diethylamino hydroxybenzoyl hexyl benzoate (Uvinul A Plus), ecamsule (Mexoryl SX) and menthyl anthranilate. Non-limiting examples of a UVB sunscreen agent include amiloxate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), Padimate 0 (Escalol 507), phenylbenzimidazole sulfonic acid (Ensulizole), polysilicone-15 (Parsol SLX) and trolamine salicylate. Non-limiting examples of a broad-spectrum UVA/UVB sunscreen agent include bemotrizinol (Tinosorb S), benzophenones 1-12, dioxybenzone, drometrizole trisiloxane (Mexoryl XL), Iscotrizinol (Uvasorb HEB), octocrylene, oxybenzone (Eusolex 4360), sulisobenzone, bisoctrizole (Tinosorb M), titanium dioxide, and zinc oxide.

A sunscreen agent disclosed herein can have a log P value indicating that the compound is soluble in an organic solvent. As used herein, the term "log P value" refers to the logarithm (base 10) of the partition coefficient (P) for a compound and is a measure of lipophilicity. It is a partition coefficient expressed as the log ratio of the concentrations of the solute in the solvent and is a measure of differential solubility of a compound in two solvents. Typically, P is defined as the ratio of concentrations of a unionized compound in the two phases of a mixture of two immiscible solvents at equilibrium. Thus, log P=Log 10 (P), where P=[solute in immiscible solvent 1]/[solute in immiscible solvent 2]. With regard to organic and aqueous phases, the log P value of a compound is constant for any given pair of aqueous and organic solvents, and its value can be determined empirically by one of several phase-partitioning methods known to one skilled in the art including, e.g., a shake flask assay, a HPLC assay, and an interface between two immiscible electrolyte solutions (ITIES) assay.

In an embodiment, a sunscreen agent disclosed herein has a log P value of at least 4.0. In aspects of this embodiment, a sunscreen agent disclosed herein has a log P value of, e.g. 1.1 or more, 1.2 or more, 1.3 or more, 1.4 or more, 1.5 or more, 1.6 or more, 1.7 or more, 1.8 or more, 1.9 or more, 2.0 or more, 2.1 or more, 2.2 or more, 2.3 or more, 2.4 or more, 2.5 or more, 2.6 or more, 2.7 or more, 2.8 or more, 2.9 or more, 3.0 or more, 3.1 or more, 3.2 or more, 3.3 or more, 3.4 or more, 3.5 or more, 3.6 or more, 3.7 or more, 3.8 or more, 3.9 or more 4.0 or more. In other aspects of this embodiment, a sunscreen agent disclosed herein has a log P value of between, e.g., 1.8 to 4.0, 2.0 to 4.0, 2.1 to 4.0, 2.2 to 4.0, 2.3 to 4.0, 2.4 to 4.0, 2.5 to 4.0, 2.6 to 4.0, 2.8 to 4.0, 3.0 to 4.0, 3.1 to 4.0, 3.2 to 4.0, 3.3 to 4.0, 3.4 to 4.0, 3.5 to 4.0, 3.6 to 4.0.

A sunscreen agent disclosed herein can be an FDA-approved sunscreen agent or a European Union sunscreen agent. In an embodiment, a sunscreen agent marketed in the United States, preferred cosmetically-acceptable sunscreen agents and concentrations (reported as a percentage by weight of the total cosmetic sunscreen composition, and referring to the final percentage of the sunscreen agent after addition to the bodywash) include: aminobenzoic acid (also called para-aminobenzoic acid and PABA; 15% or less; a UVB absorbing organic sunscreen), avobenzone (also called butyl methoxy dibenzoylmethane; 3% or less, a UVA I absorbing organic sunscreen), cinoxate (also called 2-ethoxyethyl p-methoxycinnamate; 3% or less, a UVB absorbing organic sunscreen), decamsule, dioxybenzone (also called benzophenone-8; 3% or less, a UVB and UVA II absorbing organic sunscreen), homosalate (15% or less, a UVB absorbing organic sunscreen), menthyl anthranilate (also called menthyl 2-aminobenzoate; 5% or less, a UVA II absorbing organic sunscreen), octocrylene (also called 2-ethylhexyl-2-cyano-3,3 diphenylacrylate; 10% or less, a UVB absorbing organic sunscreen), octyl methoxycinnamate (7.5% or less, a UVB absorbing organic sunscreen), octyl salicylate (also called 2-ethylhexyl salicylate; 5% or less, a UVB absorbing organic sunscreen), oxybenzone (also called benzophenone-3; 6% or less, a UVB and UVA II absorbing organic sunscreen), padimate 0 (also called octyl dimethyl PABA; 8% or less, a UVB absorbing organic sunscreen), phenylbenzimidazole sulfonic acid (water soluble; 4% or less, a UVB absorbing organic sunscreen), sulisobenzone (also called benzophenone-4; 10% or less, a UVB and UVA II absorbing organic sunscreen), titanium dioxide (25% or less, an inorganic physical blocker of UVA and UVB), trolamine salicylate (also called triethanolamine salicylate; 12% or less, a UVB absorbing organic sunscreen), zinc oxide (25% or less, an inorganic physical blocker of UVA and UVB) and Tineubin (a UVA absorber manufactured by BASF).

In another embodiment, a second sunscreen agent recognized as safe and effective by the US Food and Drug Administration includes, without limitation, p-aminobenzoic acid, Cinoxate, Avobenzone, digalloyl trioleate, dioxybenzone, ethyl 4-[bis(hydroxypropyl)]aminobenzoate, glyceryl aminobenzoate, homosalate, lawsone with dihydroxyacetone, menthyl anthranilate, octocrylene (ethyl 2-cyano-3,3-diphenyl acrylate), octyl salicylate, oxybenzone, Padimate 0, phenylbenzimidazole sulfonic acid, red petrolatum, sulisobenzone, titanium dioxide, zinc oxide, including regular grades and grades of such fine particle size as enable the composition to be translucent or transparent, and triethanolamine salicylate. Additional sunscreen compounds recognized by European authorities include N,N,N-trimethyl-4-(2-oxoborn-3-ylidene methyl)anilinium methyl sulfate, 3-imidazol-4-ylacrylic acid and its ethyl ester, 2-phenylbenzimidazole-5-sulfonic acid and its salts, ethoxylated 4-aminobenzoic acid, amyl 4-dimethylaminobenzoate, 3,3,5-trimethylcyclohexyl-2-acetamidobenzoate, potassium cinnamate, 4-methoxycinnamic acid salts, propyl 4-methoxycinnamate, salicylic acid salts, amyl 4-methoxycinnamate, mexenone, sulisobenzone, 2-ethylhexyl 2-(4-phenylbenzoyl)-benzoate, 5-methyl-2-phenylbenzoxazole, sodium 3,4-dimethoxyphenylglyoxylate, 1,3-bis(4-methoxyphenyl)propane-1,3-dione, 5-(3,3-dimethyl-2-norbornylidene)-3-penten-2-one, alpha-(2-oxoborn-3-ylidene)-p-xylene-2-sulfonic acid, alpha-(2-oxoborn-3-ylidene) toluene-4-sulfonic acid and its salts, 3-(4-methylbenzylidene)bornan-2-one, 3-benzylidenebornan-2-one, alpha-cyano-4-methoxycinnamic acid and its hexyl ester, 1-p-cumenyl-3-phenylpropane-1,-3-dione, 4-isopropylbenzyl salicylate, cyclohexyl 4-methoxycinnamate, and 1-(4-t-butylphenyl)-3-(4-methoxyphenyl)propane-1,3-dione.

In another embodiment, a sunscreen agent marketed in the European Union, preferred cosmetically-acceptable sunscreen agents and concentrations (reported as a percentage by weight of the total cosmetic sunscreen composition, and referring to the final percentage of the sunscreen agent after addition to the bodywash) include: PABA (5% or less), camphor benzalkonium methosulfate (6% or less), homosalate (10% or less), benzophenone-3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), Mexoryl XL, Neo heliopan AP, Benzophenone-9, Uvinul T 150, Uvinul A Plus, Uvasorb HEB, Parsol SLX, benzylidene camphor sulfonic acid (6% or less, expressed as acid), octocrylene (10% or less, expressed as acid), polyacrylamidomethyl benzylidene camphor (6% or less), octyl methoxycinnamate (10% or less), PEG-25 PABA (10% or less), isoamyl p-methoxycinnamate (10% or less), ethylhexyl triazone (5% or less), drometrizole trielloxane (15% or less), diethylhexyl butamido triazone (10% or less), 4-methylbenzylidene camphor (4% or less), 3-benzylidene camphor (2% or less), ethylhexyl salicylate (5% or less), ethylhexyl dimethyl PABA (8% or less), benzophenone-4 (5%, expressed as acid), methylene bis-benztriazolyl tetramethylbutylphenol (10% or less), disodium phenyl dibenzimidazole tetrasulfonate (10% or less, expressed as acid), bisethylhexyloxyphenol methoxyphenol triazine (10% or less), methylene bisbenzotriazolyl tetramethylbutylphenol (10% or less, also called TINOSORB® M), and bisethylhexyloxyphenol methoxyphenyl triazine. (10% or less, also called TINOSORB® S).

A sunscreen agent useful as part of a composition disclosed herein are also described in, e.g., U.S. Pat. Nos. 5,169,624; 5,543,136; 5,849,273; 5,904,917; 6,224,852; 6,217,852; and Segarin et al., chapter Vil, pages 189 of Cosmetics Science and Technology, and Final Over-the-Counter Drug Products Monograph on Sunscreens (Federal Register, 1999:64:27666 27963), each of which are incorporated herein by reference in its entirety.

The sun protection factor (SPF) of a sunscreen agent is a laboratory measure of the effectiveness of sunscreen. The SPF is the amount of UV radiation required to cause sunburn on the skin with the sunscreen on, as a multiple of the amount required without the sunscreen. SPF is determined by measuring the Minimal Erythemal Dose ("MED") and is defined as the threshold dose that produces skin erythema. The MED indicates the amount of energy irradiating the skin and the responsiveness of the skin to the radiation. In order to determine the MED, the reaction of the skin is recorded 24 hours after exposure to UV radiation. The minimal dose that induces any visible reddening at that point is defined as one MED. Redness that occurs immediately after exposure, however, and disappears during the following three to five hours is mainly caused by heat and is not comparable with real UV erythema. The SPF of a particular sunscreen agent is obtained by dividing the MED of skin that has been protected by a sunscreen agent by the MED of unprotected skin. The higher the SPF, the more effective the sunscreen agent is in preventing an individual from skin erythema, which is on an individual is recognized as constituting a sunburn. SPF is generally measured in numerical increments that identify how long an individual can be exposed to UV radiation from the sun before that same individual will experience 1 MED. For example, utilizing a sunscreen with an SPF of 6 will allow an individual to be exposed to the sun six times longer than an SPF of 1 before that individual receives 1 MED. As the SPF value of a sunscreen increases, the less chance exists for development UV erythema of the skin. Methods for measuring SPF are described in, e.g., FDA monograph C.F.R. 21. A method for applying the sunscreen prior to measurement is as follows: Wet 50 cm$^2$ square area of testing site with 10 ml of water delivered with a syringe. Apply test sample as per FDA monograph to area. Work lather on the subject for 3 minutes to allow the product to absorb into the skin. Rinse area after 2 additional minutes with 20 ml of water. Pat dry and allow 15 minutes before exposure to radiation as per FDA monograph.

In an embodiment, a composition comprising one or more sunscreen agents as disclosed herein may have an average SPF value ranging from about 2 to about 100. In aspects of this embodiment, a composition comprising one or more sunscreen agents as disclosed herein may have an average SPF value of, e.g., at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95 or at least 100. In other aspects of this embodiment, a composition comprising one or more sunscreen agents as disclosed herein may have an average SPF value of, e.g., at most 5, at most 10, at most 15, at most 20, at most 25, at most 30, at most 35, at most 40, at most 45, at most 50, at most 55, at most 60, at most 65, at most 70, at most 75, at most 80, at most 85, at most 90, at most 95 or at most 100.

In yet other aspects of this embodiment, a composition comprising one or more sunscreen agents as disclosed herein may have an average SPF value of, e.g., about 1 to about 10, about 1 to about 15, about 1 to about 20, about 1 to about 30, about 1 to about 40, about 1 to about 50, about 1 to about 60, about 1 to about 70, about 1 to about 80, about 1 to about 90, about 1 to about 100, about 5 to about 15, about 5 to about 20, about 5 to about 30, about 5 to about 40, about 5 to about 50, about 5 to about 60, about 5 to about 70, about 5 to about 80, about 5 to about 90, about 5 to about 100, about 10 to about 15, about 10 to about 20, about 10 to about 30, about 10 to about 40, about 10 to about 50, about 10 to about 60, about 10 to about 70, about 10 to about 80, about 10 to about 90, about 10 to about 100, about 20 to about 30, about 20 to about 40, about 20 to about 50, about 20 to about 60, about 20 to about 70, about 20 to about 80, about 20 to about 90, about 20 to about 100, about 30 to about 40, about 30 to about 50, about 30 to about 60, about 30 to about 70, about 30 to about 80, about 30 to about 90, about 30 to about 100, about 40 to about 50, about 40 to about 60, about 40 to about 70, about 40 to about 80, about 40 to about 90, about 40 to about 100, about 50 to about 60, about 50 to about 70, about 50 to about 80, about 50 to about 90, about 50 to about 100, about 60 to about 70, about 60 to about 80, about 60 to about 90, about 60 to about 100, about 70 to about 80, about 70 to about 90, about 70 to about 100, about 80 to about 90, about 80 to about 100 or about 90 to about 100.

In other aspects of this embodiment, a composition comprising one or more sunscreen agents as disclosed herein provides an average SPF value of, e.g., at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95 or at least 100 for an average time period of, e.g., at least 4 hours, at least 8 hours, at least 12 hours, at least 16 hours, at least 20 hours, at least 24 hours, at least 36 hours, at least 48 hours, at least 60 hours, at least 72 hours, at least 4 days, at least 5 days, at least 6 days, at least 7 days, at least 8 days, at least 9 days, at least 10 days, at least 11 days, at least 12 days, at least 13 days or at least 14 days.

In yet other aspects of this embodiment, a composition comprising one or more sunscreen agents as disclosed herein provides an average SPF value of, e.g., at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95 or at least 100 for an average time period of, e.g., at about 4 hours to about 8 hours, about 4 hours to about 12 hours, about 4 hours to about 16 hours, about 4 hours to about 20 hours, about 4 hours to about 24 hours, about 4 hours to about 36 hours, about 4 hours to about 48 hours, about 4 hours to about 60 hours, about 4 hours to about 72 hours, about 8 hours to about 12 hours, about 8 hours to about 16 hours, about 8 hours to about 20 hours, about 8 hours to about 24 hours, about 8 hours to about 36 hours, about 8 hours to about 48 hours, about 8 hours to about 60 hours, about 8 hours to about 72 hours, about 12 hours to about 16 hours, about 12 hours to about 20 hours, about 12 hours to about 24 hours, about 12 hours to about 36 hours, about 12 hours to about 48 hours, about 12 hours to about 60 hours, about 12 hours to about 72 hours, about 16 hours to about 20 hours, about 16 hours to about 24 hours, about 16 hours to about 36 hours, about 16 hours to about 48 hours, about 16 hours to about 60 hours, about 16 hours to about 72 hours, about 20 hours to about 24 hours, about 20 hours to about 36 hours, about 20 hours to about 48 hours, about 20 hours to about 60 hours, about 20 hours to about 72 hours, about 24 hours to about 36 hours, about 24 hours to about 48 hours, about 24 hours to about 60 hours, about 24 hours to about 72 hours, about 36 hours to about 48 hours, about 36 hours to about 60 hours, about 36 hours to about 72 hours, about 48 hours to about 60 hours, about 48 hours to about 72 hours, about 60 hours to about 72 hours, about 3 days to about 4 days, about 3 days to about 5 days, about 3 days to about 6 days, about 3 days to about 7 days, about 3 days to about 8 days, about 3 days to about 9 days, about 3 days to about 10 days, about 4 days to about 5 days, about 4 days to about 6 days, about 4 days to about 7 days, about 4 days to about 8 days, about 4 days to about 9 days, about 4 days to about 10 days, about 5 days to about 6 days, about 5 days to about 7 days, about 5 days to about 8 days, about 5 days to about 9 days, about 5 days to about 10 days, about 6 days to about 7 days, about 6 days to about 8 days, about 6 days to about 9 days, about 6 days to about 10 days, about 7 days to about 8 days, about 7 days to about 9 days or about 7 days to about 10 days.

In other aspects of this embodiment, a composition comprising one or more sunscreen agents as disclosed herein provides an average SPF value of, e.g., about 1 to about 10, about 1 to about 15, about 1 to about 20, about 1 to about 30, about 1 to about 40, about 1 to about 50, about 1 to about 60, about 1 to about 70, about 1 to about 80, about 1 to about 90, about 1 to about 100, about 5 to about 15, about 5 to about 20, about 5 to about 30, about 5 to about 40, about 5 to about 50, about 5 to about 60, about 5 to about 70, about 5 to about 80, about 5 to about 90, about 5 to about 100, about 10 to about 15, about 10 to about 20, about 10 to about 30, about 10 to about 40, about 10 to about 50, about 10 to about 60, about 10 to about 70, about 10 to about 80, about 10 to about 90, about 10 to about 100, about 20 to about 30, about 20 to about 40, about 20 to about 50, about 20 to about 60, about 20 to about 70, about 20 to about 80, about 20 to about 90, about 20 to about 100, about 30 to about 40, about 30 to about 50, about 30 to about 60, about 30 to about 70, about 30 to about 80, about 30 to about 90, about 30 to about 100, about 40 to about 50, about 40 to about 60, about 40 to about 70, about 40 to about 80, about 40 to about 90, about 40 to about 100, about 50 to about 60, about 50 to about 70, about 50 to about 80, about 50 to about 90, about 50 to about 100, about 60 to about 70, about 60 to about 80, about 60 to about 90, about 60 to about 100, about 70 to about 80, about 70 to about 90, about 70 to about 100, about 80 to about 90, about 80 to about 100 or about 90 to about 100 for an average time period of, e.g., at least 4 hours, at least 8 hours, at least 12 hours, at least 16 hours, at least 20 hours, at least 24 hours, at least 36 hours, at least 48 hours, at least 60 hours, at least 72 hours, at least 4 days, at least 5 days, at least 6 days, at least 7 days, at least 8 days, at least 9 days, at least 10 days, at least 11 days, at least 12 days, at least 13 days or at least 14 days.

In yet other aspects of this embodiment, a composition comprising one or more sunscreen agents as disclosed herein provides an average SPF value of, e.g., about 1 to about 10, about 1 to about 15, about 1 to about 20, about 1 to about 30, about 1 to about 40, about 1 to about 50, about 1 to about 60, about 1 to about 70, about 1 to about 80, about 1 to about 90, about 1 to about 100, about 5 to about 15, about 5 to about 20, about 5 to about 30, about 5 to about 40, about 5 to about 50, about 5 to about 60, about 5 to about 70, about 5 to about 80, about 5 to about 90, about 5 to about 100, about 10 to about 15, about 10 to about 20, about 10 to about 30, about 10 to about 40, about 10 to about 50, about 10 to about 60, about 10 to about 70, about 10 to about 80, about 10 to about 90, about 10 to about 100, about 20 to about 30, about 20 to about 40, about 20 to about 50, about 20 to about 60, about 20 to about 70, about 20 to about 80, about 20 to about 90, about 20 to about 100, about 30 to about 40, about 30 to about 50, about 30 to about 60, about 30 to about 70, about 30 to about 80, about 30 to about 90, about 30 to about 100, about 40 to about 50, about 40 to about 60, about 40 to about 70, about 40 to about 80, about 40 to about 90, about 40 to about 100, about 50 to about 60, about 50 to about 70, about 50 to about 80, about 50 to about 90, about 50 to about 100, about 60 to about 70, about 60 to about 80, about 60 to about 90, about 60 to about 100, about 70 to about 80, about 70 to about 90, about 70 to about 100, about 80 to about 90, about 80 to about 100 or about 90 to about 100 for an average time period of, e.g., at about 4 hours to about 8 hours, about 4 hours to about 12 hours, about 4 hours to about 16 hours, about 4 hours to about 20 hours, about 4 hours to about 24 hours, about 4 hours to about 36 hours, about 4 hours to about 48 hours, about 4 hours to about 60 hours, about 4 hours to about 72 hours, about 8 hours to about 12 hours, about 8 hours to about 16 hours, about 8 hours to about 20 hours, about 8 hours to about 24 hours, about 8 hours to about 36 hours, about 8 hours to about 48 hours, about 8 hours to about 60 hours, about 8 hours to about 72 hours, about 12 hours to about 16 hours, about 12 hours to about 20 hours, about 12 hours to about 24 hours, about 12 hours to about 36 hours, about 12 hours to about 48 hours, about 12 hours to about 60 hours, about 12 hours to about 72 hours, about 16 hours to about 20 hours, about 16 hours to about 24 hours, about 16 hours to about 36 hours, about 16 hours to about 48 hours, about 16 hours to about 60 hours, about 16 hours to about 72 hours, about 20 hours to about 24 hours, about 20 hours to about 36 hours, about 20 hours to about 48 hours, about 20 hours to about 60 hours, about 20 hours to about 72 hours, about 24 hours to about 36 hours, about 24 hours to about 48 hours, about 24 hours to about 60 hours, about 24 hours to about 72 hours, about 36 hours to about 48 hours, about 36 hours to about 60 hours, about 36 hours to about 72 hours, about 48 hours to about 60 hours, about 48 hours to about 72 hours, about 60 hours to about 72 hours, about 3 days to about 4 days, about 3 days to about 5 days, about 3 days to about 6 days, about 3 days to about 7 days, about 3 days to about 8 days, about 3 days to about 9 days, about 3 days to about 10 days, about 4 days to about 5 days, about 4 days to about 6 days, about 4 days to about 7 days, about 4 days to about 8 days, about 4 days to about 9 days, about 4 days to about 10 days, about 5 days to about 6 days, about 5 days to about 7 days, about 5 days to about 8 days, about 5 days to about 9 days, about 5 days to about 10 days, about 6 days to about 7 days, about 6 days to about 8 days, about 6 days to about 9 days, about 6 days to about 10 days, about 7 days to about 8 days, about 7 days to about 9 days or about 7 days to about 10 days.

A composition comprising one or more sunscreen agents as disclosed herein can maintain the SPF value relative to the initial application, even after exposure to water or other liquids, such as, e.g., by washing, rinsing, or swimming. In aspects of this embodiment, a composition comprising one or more sunscreen agents as disclosed herein can maintain the SPF value relative to the initial application, even after exposure to water or other liquids by, e.g., at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95 or at least 100. In other aspects of this embodiment, a composition comprising one or more sunscreen agents as disclosed herein can maintain the SPF value relative to the initial application, even after exposure to water or other liquids by, e.g., at most 5, at most 10, at most 15, at most 20, at most 25, at most 30, at most 35, at most 40, at most 45, at most 50, at most 55, at most 60, at most 65, at most 70, at most 75, at most 80, at most 85, at most 90, at most 95 or at most 100.

In yet other aspects of this embodiment, a composition comprising one or more sunscreen agents as disclosed herein can maintain the SPF value relative to the initial application, even after exposure to water or other liquids by, e.g., about 1 to about 10, about 1 to about 15, about 1 to about 20, about 1 to about 30, about 1 to about 40, about 1 to about 50, about 1 to about 60, about 1 to about 70, about 1 to about 80, about 1 to about 90, about 1 to about 100, about 5 to about 15, about 5 to about 20, about 5 to about 30, about 5 to about 40, about 5 to about 50, about 5 to about 60, about 5 to about 70, about 5 to about 80, about 5 to about 90, about 5 to about 100, about 10 to about 15, about 10 to about 20, about 10 to about 30, about 10 to about 40, about 10 to about 50, about 10 to about 60, about 10 to about 70, about 10 to about 80, about 10 to about 90, about 10 to about 100, about 20 to about 30, about 20 to about 40, about 20 to about 50, about 20 to about 60, about 20 to about 70, about 20 to about 80, about 20 to about 90, about 20 to about 100, about 30 to about 40, about 30 to about 50, about 30 to about 60, about 30 to about 70, about 30 to about 80, about 30 to about 90, about 30 to about 100, about 40 to about 50, about 40 to about 60, about 40 to about 70, about 40 to about 80, about 40 to about 90, about 40 to about 100, about 50 to about 60, about 50 to about 70, about 50 to about 80, about 50 to about 90, about 50 to about 100, about 60 to about 70, about 60 to about 80, about 60 to about 90, about 60 to about 100, about 70 to about 80, about 70 to about 90, about 70 to about 100, about 80 to about 90, about 80 to about 100 or about 90 to about 100.

Multiple applications of a composition comprising one or more sunscreen agents as disclosed herein can result in an increase in the SPF value relative to the initial application, even after exposure to water or other liquids, such as, e.g., by washing, rinsing, or swimming. For example, two or more, three or more, four or more, five or more, six or more, seven or more, eight or more, nine or more, or ten or more applications of a composition comprising one or more sunscreen agents as disclosed herein can result in an increased in the SPF value relative to the initial application, even after exposure to water or other liquids.

In aspects of this embodiment, multiple applications of a composition comprising one or more sunscreen agents as disclosed herein can increase the SPF value relative to the initial application, even after exposure to water or other liquids by, e.g., at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95 or at least 100. In other aspects of this embodiment, multiple applications of a composition comprising one or more sunscreen agents as disclosed herein can increase the SPF value relative to the initial application, even after exposure to water or other liquids by, e.g., at most 5, at most 10, at most 15, at most 20, at most 25, at most 30, at most 35, at most 40, at most 45, at most 50, at most 55, at most 60, at most 65, at most 70, at most 75, at most 80, at most 85, at most 90, at most 95 or at most 100.

In yet other aspects of this embodiment, multiple applications of a composition comprising one or more sunscreen agents as disclosed herein can increase the SPF value relative to the initial application, even after exposure to water or other liquids by, e.g., about 1 to about 10, about 1 to about 15, about 1 to about 20, about 1 to about 30, about 1 to about 40, about 1 to about 50, about 1 to about 60, about 1 to about 70, about 1 to about 80, about 1 to about 90, about 1 to about 100, about 5 to about 15, about 5 to about 20, about 5 to about 30, about 5 to about 40, about 5 to about 50, about 5 to about 60, about 5 to about 70, about 5 to about 80, about 5 to about 90, about 5 to about 100, about 10 to about 15, about 10 to about 20, about 10 to about 30, about 10 to about 40, about 10 to about 50, about 10 to about 60, about 10 to about 70, about 10 to about 80, about 10 to about 90, about 10 to about 100, about 20 to about 30, about 20 to about 40, about 20 to about 50, about 20 to about 60, about 20 to about 70, about 20 to about 80, about 20 to about 90, about 20 to about 100, about 30 to about 40, about 30 to about 50, about 30 to about 60, about 30 to about 70, about 30 to about 80, about 30 to about 90, about 30 to about 100, about 40 to about 50, about 40 to about 60, about 40 to about 70, about 40 to about 80, about 40 to about 90, about 40 to about 100, about 50 to about 60, about 50 to about 70, about 50 to about 80, about 50 to about 90, about 50 to about 100, about 60 to about 70, about 60 to about 80, about 60 to about 90, about 60 to about 100, about 70 to about 80, about 70 to about 90, about 70 to about 100, about 80 to about 90, about 80 to about 100 or about 90 to about 100.

In an embodiment, a composition comprising one sunscreen agents. In another embodiment, a composition comprising a plurality of sunscreen agents. In aspects of this embodiment, a composition comprises, e.g., one or more, two or more, three or more, four or more, five or more, six or more, seven or more, eight or more, nine or more or ten or more different sunscreen agents. In aspects of this embodiment, a composition comprises, e.g., about 1 to about 2, about 1 to about 3, about 1 to about 4, about 1 to about 5, about 1 to about 6, about 1 to about 7, about 1 to about 8, about 1 to about 9, about 1 to about 10, about 2 to about 3, about 2 to about 4, about 2 to about 5, about 2 to about 6, about 2 to about 7, about 2 to about 8, about 2 to about 9, about 2 to about 10, about 3 to about 4, about 3 to about 5, about 3 to about 6, about 3 to about 7, about 3 to about 8, about 3 to about 9, about 3 to about 10, about 4 to about 5, about 4 to about 6, about 4 to about 7, about 4 to about 8, about 4 to about 9, about 4 to about 10, about 5 to about 6, about 5 to about 7, about 5 to about 8, about 5 to about 9, about 5 to about 10, about 6 to about 7, about 6 to about 8, about 6 to about 9, about 6 to about 10, about 7 to about 8, about 7 to about 9, about 7 to about 10, about 8 to about 9, about 8 to about 10 or about 9 to about 10 different sunscreen agents.

A composition disclosed herein comprises a sunscreen agent in an amount sufficient to confer absorptive, blocking and/or reflective properties within the wavelength region of between about 290 to about 420 nm. In aspects of this embodiment, a composition disclosed herein comprises a sunscreen agent in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises a sunscreen agent in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises a sunscreen agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

In aspects of this embodiment, a composition disclosed herein comprises a sunscreen agent in an amount sufficient to absorb, block and/or reflect, e.g., at least 10%, at least 20%, at least 30%, at least 40%, at least 50%, at least 60%, at least 70, at least 80%, at least 90%, or at least 95% of UVA radiation. In other aspects of this embodiment, a composition disclosed herein comprises a sunscreen agent in an amount sufficient to absorb, block and/or reflect, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% of UVA radiation.

In other aspects of this embodiment, a composition disclosed herein comprises a sunscreen agent in an amount sufficient to absorb, block and/or reflect, e.g., at least 10%, at least 20%, at least 30%, at least 40%, at least 50%, at least 60%, at least 70, at least 80%, at least 90%, or at least 95% of incident radiation at wave lengths of about 290 nm to about 320 nm. In other aspects of this embodiment, a composition disclosed herein comprises a sunscreen agent in an amount sufficient to absorb, block and/or reflect, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% of incident radiation at wave lengths of about 290 nm to about 320 nm.

In aspects of this embodiment, a composition disclosed herein comprises a sunscreen agent in an amount sufficient to absorb, block and/or reflect, e.g., at least 10%, at least 20%, at least 30%, at least 40%, at least 50%, at least 60%, at least 70, at least 80%, at least 90%, or at least 95% of UVB radiation. In other aspects of this embodiment, a composition disclosed herein comprises a sunscreen agent in an amount sufficient to absorb, block and/or reflect, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% of UVB radiation.

In other aspects of this embodiment, a composition disclosed herein comprises a sunscreen agent in an amount sufficient to absorb, block and/or reflect, e.g., at least 10%, at least 20%, at least 30%, at least 40%, at least 50%, at least 60%, at least 70, at least 80%, at least 90%, or at least 95% of incident radiation at wave lengths of about 320 nm to about 420 nm. In other aspects of this embodiment, a composition disclosed herein comprises a sunscreen agent in an amount sufficient to absorb, block and/or reflect, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% of incident radiation at wave lengths of about 320 nm to about 420 nm.

In aspects of this embodiment, a composition disclosed herein comprises a sunscreen agent in an amount sufficient to absorb, block and/or reflect, e.g., at least 10%, at least 20%, at least 30%, at least 40%, at least 50%, at least 60%, at least 70, at least 80%, at least 90%, or at least 95% of UVA/UVB radiation. In other aspects of this embodiment, a composition disclosed herein comprises a sunscreen agent in an amount sufficient to absorb, block and/or reflect, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% of UVA/UVB radiation.

In other aspects of this embodiment, a composition disclosed herein comprises a sunscreen agent in an amount sufficient to absorb, block and/or reflect, e.g., at least 10%, at least 20%, at least 30%, at least 40%, at least 50%, at least 60%, at least 70, at least 80%, at least 90%, or at least 95% of incident radiation at wave lengths of about 290 nm to about 420 nm. In other aspects of this embodiment, a composition disclosed herein comprises a sunscreen agent in an amount sufficient to absorb, block and/or reflect, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% of incident radiation at wave lengths of about 290 nm to about 420 nm.

Aspects of the present specification disclose a photostabilizing agent. Some active agents are photosensitive and are susceptible to photochemically-initiated degradation reactions, e.g., such as a sunscreen agent or colorants used in paints. A photostabilizing agent stabilizes against light-induced degradation and helps prevent at least one active agent disclosed herein from losing its effectiveness or integrity.

One type of photostabilizing agent helps stabilize an active agent disclosed herein structurally and geometrically through electrostatic and van der Waals interactions, which insulate the active agent from being altered during a chemical reaction. Another type of photostabilizing agent protects an active agent disclosed herein by dissipating the energy from UV radiation more quickly, thus reducing or even eliminating the possibility of a chemical reaction. This process is called energy transfer, and it can take place when an active agent disclosed herein and photostabilizing agent exchange electrons.

A photostabilizing agent enables the use of less of certain active agents, for example, sunscreen agents, which increases the safety of a composition disclosed herein by reducing the amount of the active agent used, thereby reducing the amount of the active agent that can be absorbed into the body and systemically distributed. In addition, reducing the amount of the active agent also reduces the overall cost of making a composition disclosed herein. Non-limiting examples of a photostabilizing agent include 4-methylbenzylidene camphor (MBC), an α-olefin copolymer, Bemotrizinol (BTZ), Galangal extract, ethylhexyl methoxycrylene (SOLASTAY® 51), a hindered amine light stabilizer [HALS, 2,2,6,6-tetramethyl piperidine-based compounds including TINUVIN® compounds (BASF), CHIMASSORB® compounds (BASF) and LA compounds (Amfine)], hexylresorcinol, Polyester-25 (a bis-Methoxycrylene/octyldodecyl adipic acid/methylpropanediol copolymer)(SOLASTAY® P1), octasalicyalte (octasalate), trimethoxybenzylidene pentanedione (SYNOXYL® HSS, Sytheon, Ltd.), polyester-8. Photostabilizing agents useful in a composition disclosed herein are also described in, e.g., U.S. Pat. No. 5,801,244 and U.S. Patent Publications 2009/0074684 and 2013/0059924, each of which is incorporated herein by reference in its entirety.

A composition disclosed herein comprises a photostabilizing agent in an amount sufficient to help prevent a sunscreen agent disclosed herein from losing its effectiveness in absorbing, blocking and/or reflecting UV radiation. In aspects of this embodiment, a composition disclosed herein comprises a photostabilizing agent in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises a photostabilizing agent in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises a photostabilizing agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

Aspects of the present specification disclose a moisturizing agent. A moisturizing agent prevents loss of moisture and/or hydrates the skin and/or increases the water content of the skin and/or replaces the oils contained in the skin. A moisturizing agent includes, without limitation, an occlusive, which works by forming a thin film on the surface of the skin to prevent moisture loss, a humectant, which attracts water vapor from the air to moisturize the skin, and a restoration agent, which restore natural moisturizing factors to the skin. A moisturizing agent includes, without limitation, an emollient, which works by softening or soothing the skin. A moisturizing agent can be used as an after-care treatment of excessive sun exposure or sunburn. A moisturizing agent includes, without limitation, glycerin, chamomile, aloe, cetyl alcohol, grape seed oil, dimethicone, an α-hydroxy acid, a silicone-based agent, a petrolatum-based agent and an antioxidant. A silicone-based agent includes, without limitation, cyclopentasiloxane, cyclohexasiloxane, cyclomethicone, dimethicone and phenyl trimethicone.

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, saccharide isomerate, salts of pyrrolidone carboxylic acid, potassium PCA, propylene glycol, sodium glucuronate, sodium PCA, sorbitol, sucrose, trehalose, urea, and xylitol.

Other examples of moisturizing agents that can be used with the compositions of the present invention include acetylated lanolin, acetylated lanolin alcohol, alanine, algae extract, Aloe barbadensis, Aloe barbadensis extract, Aloe barbadensis gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, β-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, Geranium *maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica* limonum) oil, linoleic acid, linolenic acid, *Macadamia ternifolia* nut oil, maltitol, *matricaria* (*Chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

An α-hydroxy acid includes, without limitation, glycolic acid, lactic acid, malic acid, citric acid and tartaric acid. An antioxidant includes, without limitation, 6-Hydroxymelatonin, acetyl-L-carnitine, a carotene, curcumin, edaravone, glutathione, hydroxytyrosol, L-carnitine, ladostigil, a lipoic acid like α-lipoic acid, melatonin, mofegiline, N-acetylcysteine, N-acetylserotonin, oleocanthal, oleuropein, a polyphenol, rasagiline, resveratrol, selegiline, selenium, tirlazad, tyrosol, uric acid, ubiquinol, ubiquinone, a vitamin A like a carotenoid, a vitamin C like an ascorbic acid, and a vitamin E like a tocopherol and a tocotrienol.

The benefit of silicon dioxide-based particles comprising one or more moisturizing agents (such as glycerin) over a free moisturizing agent (non-encapsulated) is that it improves the moisturizing properties. The particles form a layered barrier on the skin that prevents drying and keeps moisture within the skin. In addition, as a portion of the particles break through, e.g., through surface friction, the breakage releases the moisturizing active agent contained within the ruptured particle.

Aspects of the present specification disclose an arachnid/insect repellent. An arachnid/insect repellent includes, without limitation, a synthetic chemical compound or a compound purified from a natural source. Non-limiting examples of an arachnid/insect repellent that is a synthetic chemical compound, include, without limitation, N,N-Diethyl-m-toluamide (DEET), dimethyl phthalate, ethyl hexanediol, indalone, di-n-propylisocinchoronate, bicycloheptene, dicarboximide, dimethyl carbate, dimethyl phthalate, metofluthrin, indalone, permethrin, icaridin, nepetalactone, tetrahydrofuraldehyde ethyl butylacetylaminopropionate (IR-3535), p-menthane-3,8-diol (PMD), tricyclodecenyl allyl ether, ethylhexanediol, SS220 ((1S,2'S)-Methylpiperidinyl-3-cyclohexen-1-carboxamide), an anthranilate-based arachnid/insect repellent, such as, e.g., methyl anthranilate, N,N-dimethylanthranilic acid (DMA), ethyl anthranilate (EA), and butyl anthranilate (BA) and hydroxyethyl isobutyl piperidine carboxylate.

Non-limiting examples of an arachnid/insect repellent that is a compound purified from a natural source includes plant-derived materials and sea-life, including fish. Plant-derived materials with arachnid/insect repellent activity include, without limitation, plant oils derived from, e.g., *achillea, Andrographis paniculata*, anise, basil, bay, bergamot (e.g., *Monardia fistulosa, Monarda didyma, Citrus bergamia, Monarda punctata*), bitter orange peel, black pepper, calamus, camphor, cananga (e.g., java), cardamom, carnation (e.g., *Dianthus caryophyllus*), cassia, castor, cedar (e.g., hinoki), cedarwood, celery, chamomile, cinnamon, *Citrus aurantium amara, Citrus aurantium dulcis, Citrus unshiu*, clary sage, clove (e.g., *Eugenia caryophyllus*), clove bud, coriander, corn, cotton seed, *Cymbopogon martini, eucalyptus*, lemon *eucalyptus*, evening primrose, fennel, garlic, geranium, ginger, grapefruit, guaiacwood, gurjun balsam, hiba, jasmine, jojoba, juniper berry, lavender, lemon grass, lemon, lime, linseed, *Litsea cubeba*, marigold, marjoram, mint, mustard, neem, nutmeg, orange, orris root (e.g., iris florentina), patchouli (e.g., *Pogostemon cablin*), pepper, peppermint (e.g., *Mentha piperita*), pimento berry, pimento leaf, pine needle, pine, rose, rosemary (e.g., *Rosmarinus officinalis*), ryu, sage, sandalwood (e.g., *Santalum album*), sassafras, sesame, soybean, spearmint, spice, spike lavender, starflower, tangerine, tea seed, tea tree, thyme, thulasi, tomato, turmeric, white cedar, white grapefruit, wintergreen and yellow nightshade.

A plant oil or derivative thereof may be extracted from a natural source or synthetically made and include racemic mixtures, enantiomers, diastereomers, hydrates, salts, solvates and metabolites, etc. Such oils generally contain as a major constituent an acyclic monoterpene alcohol or aldehyde, a benzenoid aromatic compound containing at least one oxygenated substituent or side chain, or a monocarbocyclic terpene generally having a six membered ring bearing one or more oxygenated substituents. Examples of suitable plant oils disclosed herein include, without limitation, α- or β-pinene; α-campholenic aldehyde; α-citronellol; α-isoamyl-cinnamic; α-pinene oxide; α-cinnamic terpinene; α-terpineol (e.g., 1-methyl-4-isopropyl-1-cyclohexen-8-ol); α-terpinene; λ-terpinene; aldehyde C16 (pure); α-phellandrene; amyl cinnamic aldehyde; amyl salicylate; anethole; anisic aldehyde; benzyl acetate; benzyl alcohol; borneol; callicarpenal; carvacrol; carveol; cineole; cinnamaldehyde; cinnamic alcohol; cis-pinane; citral (e.g., 3,7-dimethyl-2,6-octadienal); citronella; citronellal; citronellol, citronellol dextro (e.g., 3-7-dimethyl-6-octen-1-ol); citronellol; citronellyl acetate; citronellyl nitrile; d-dihydrocarvone; decyl aldehyde; diethyl phthalate; dihydroanethole; dihydrocarveol; dihydrolinalool; dihydromyrcene; dihydromyrcenol; dihydromyrcenyl acetate; dihydroterpineol; dimethyl salicylate; dimethyloctanal; dimethyloctanol; dimethyloctanyl acetate; diphenyl oxide; dipropylene glycol; d-limonene; d-pulegone; estragole; ethyl vanillin, 3-ethoxy-4-hydrobenzaldehyde; p-menthane-3,8-diol; eucalyptol (e.g., cineole); *Eucalyptus citriodora; Eucalyptus globulus*; eugenol (e.g., 2-methoxy-4-allyl phenol); fenchol; ferniol; florazon (e.g., 4-ethyl-α,α-dimethyl-benzenepropanal); galaxolide; geraniol (e.g., 2-trans-3,7-dimethyl-2,6-octadien-8-ol); geranyl acetate; geranyl nitrile; guaiacol; heliotropin; herbanate (e.g., 3-(1-methyl-ethyl) bicyclo(2,2,1) hept-5-ene-2-carboxylic acid ethyl ester); hydroxycitronellal; i-carvone; i-methyl acetate; ionone; isobutyl quinoleine (e.g., 6-secondary butyl quinoline); isobornyl acetate; isobornyl methylether; isoeugenol; isolongifolene; lavandin; limonene; linallol oxide; linallol; linalool; linalyl acetate; l-methyl acetate; longifolene; mandarin; mentha; menthane hydroperoxide; menthol crystals; menthol laevo (e.g., 5-methyl-2-isopropyl cyclohexanol); menthol; menthone laevo (e.g., 4-isopropyl-1-methyl cyclohexan-3-one); methyl anthranilate; methyl cedryl ketone; methyl chavicol; methyl hexyl ether; methyl ionone; methyl salicylate, mineral; musk ambrette; musk ketone; musk xylol; allylisothio-cyanate); myrcene; nerol; neryl acetate; nonyl aldehyde; *Myristica fragrans*; para-cymene; para-hydroxy phenyl butanone crystals (e.g., 4-(4-hydroxyphenyl)-2-butanone); passion palmarosa oil; p-cymene; pennyroyal oil; perillaldehyde; petitgrain; phenyl ethyl alcohol (e.g., 1-phenyl ethyl alcohol and 2-phenyl ethyl alcohol); phenyl ethyl propionate (e.g., 1-phenyl ethyl propionate and 2-phenyl ethyl propionate);

phenyl ethyl-2-methylbutyrate; pinane hydroperoxide; pinanol; pine ester; pinene; piperonal; piperonyl acetate; piperonyl alcohol; plinol; plinyl acetate; pseudo ionone; pyrethrum; rhodinol; rhodinyl acetate; rosalinsandenol; spirantol; terpinen-4-ol, terpenoid; terpineol; terpinolene; terpinyl acetate; tert-butylcyclohexyl acetate; tetrahydrolinalool; tetrahydrolinalyl acetate; tetrahydromyrcenol; thymol; trans-2-hexenol; trans-anethole and metabolites thereof; turpentine; vanillin (e.g., 4-hydroxy-3-methoxy benzaldehyde); vetiver; vitalizair; and the like.

Aspects of the present specification disclose an aesthetic agent. An aesthetic agent includes, without limitation, benzalkonium chloride, butamben picrate, benzocaine, bupivacaine, calamine, chlorprocaine, cocaine, dibucaine, dyclonine, etidocaine, hexylcaine, ketamine, lidocaine, mepivacaine, menthol, procaine, pramoxine, prilocaine, phenol, pramoxiine, tetracaine, xylocalne, and pharmaceutically acceptable salts thereof.

Aspects of the present specification disclose an analgesic agent. An analgesic agent includes, without limitation, dyclonine hydrochloride, aloe vera, fentanyl, capsaicin, and the like.

Aspects of the present specification disclose an anti-acne agent. An anti-acne active includes, without limitation, 5,7-dichloro-8-hydroxyquinoline, adapalene, azaleic acid, benzoyl peroxide, clindamycin, dapsone, erythromycin, long chain dicarboxylic acids, hydrocortisone, resorcinol, resorcinol acetate, retinoid, retinoid-like drug, salicylic acid, sulphur, tretinoin, urea, zinc, various natural agents such as those derived from green tree, and more. Other non-limiting examples of suitable anti-acne actives for use herein are described in U.S. Pat. No. 5,607,980, which is hereby incorporated by reference in its entirety.

Aspects of the present specification disclose an anti-allergenic agent. An anti-allergenic agent includes, without limitation, antihistamines. In a further embodiment, antihistamines are, without limitation, $H_1$ or $H_2$ antagonists or other types of histamine release inhibitors. In an additional embodiment, $H_1$ antagonists are sedating or non-sedating, including, without limitation, diphenhydramine (Benadryl), chlorpheniramine, tripelennamine, promethazine, clemastine, doxylamine, benadryl and more. In a further embodiment, $H_1$-non-sedating antihistamines include, without limitation, astemizole, terfenadine, loratadine etc. Examples of $H_2$ antagonists include cimetadine, famotidine, nizatidine, and ranitidine. In an additional embodiment, histamine-release-inhibitors include, without limitation, cromolyn commonly marketed as the sodium salt sodium cromoglicate or cromolyn sodium.

Aspects of the present specification disclose an antiangiogenic agent. An antiangiogenic agent includes angiogenesis inhibitors which are unique cancer-fighting agents that block the growth of blood vessels that support tumor growth rather than blocking the growth of tumor cells themselves. Angiogenesis inhibitors interfere in several ways with various steps in blood vessel growth. Some are monoclonal antibodies that specifically recognize and bind to vascular endothelial growth factor (VEGF). When VEGF attaches to an angiogenesis inhibitor, it is unable to activate the VEGF receptor. Other particular angiogenesis inhibitors bind to VEGF and/or its receptor as well as to other receptors on the surface of endothelial cells or to other proteins in the downstream signaling pathways, blocking their activities. Some angiogenesis inhibitors are immunomodulatory drugs—agents that stimulate or suppress the immune system—that also have antiangiogenic properties. Non-limiting examples of U.S. Food and Drug Administration (FDA) approved angiogenesis inhibitors to treat cancer, most of which are targeted therapies that were developed specifically to target VEGF, its receptor, or other specific molecules involved in angiogenesis, include Axitinib (Inlyta®), Bevacizumab (Avastin®), Cabozantinib (Cometriq®), Everolimus (Afinitor®), Lenalidomide (Revlimid®), Lenvatinib mesylate (Lenvima®), Pazopanib (Votrient®), Ramucirumab (Cyramza®), Regorafenib (Stivarga®), Sorafenib (Nexavar®), Sunitinib (Sutent®), Thalidomide (Synovir, Thalomid®), Vandetanib (Caprelsa®), Ziv-aflibercept (Zaltrap®). Other non-limiting examples of angiogenesis inhibitors, such as agents that interfere with and eliminate and/or reduce the production of pro-angiogenic factors, can also be utilized in compositions herein disclosed and in accordance with the teachings of the present disclosure, to prevent various pro-angiogeneic factors from binding to their receptors or block their actions. Non-limiting examples of anti-angiogenic agents to reduce, block, interfere with angiogenin, fibroblast growth factor (FGF), and transforming growth factor-β (TGF-β) can also be utilized in accordance with the disclosure provided herein. A composition herein disclosed comprising an antiangiogenic active agent(s) and silicon dioxide-based particles may be utilized to treat any disease, condition or malady that is associated with unwanted/undesirable proliferation of blood vessels and is not limited to the treatment of tumor-induced angiogenesis. Non-limiting examples of such conditions include angiomas, which are benign growths made up of small blood vessels that can appear anywhere on the body. These include spider angiomas, angiokeratomas, and cherry angiomas. Cherry angiomas are red or purplish in color and don't usually grow larger than ¼-inch in diameter and can appear alone or in clusters.

Aspects of the present specification disclose an anti-cellulite agent. An anti-cellulite agent includes, without limitation, isobutylmethylxanthine, caffeine, theophylline, theobromine, aminophylline, yohimbine, and mixtures thereof.

Aspects of the present specification disclose an anti-inflammatory agent. An anti-inflammatory agent includes, without limitation, steroidal, non-steroidal, and other compounds. In a further embodiment, steroidal anti-inflammatory agents include, without limitation, corticosteroids such as hydrocortisone, hydroxyltriamcinolone, α-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluorometmalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. In an additional embodiment, a steroidal anti-inflammatory for use is hydrocortisone.

A nonsteroidal anti-inflammatory agent includes, without limitation, oxicams (e.g., piroxicam, isoxicam, tenoxicam, sudoxicam, CP-14,304); salicylates (e.g., aspirin, disalcid, benorylate, trilisate, safapryn, solprin, diflunisal, fendosal); acetic acid derivatives (e.g., diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac); fenamates (e.g., mefenamic, meclofenamic, flufenamic, niflumic, tolfenamic acids); propionic acid derivatives (e,g., ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofenic); pyrazoles (e.g., phenylbutazone, oxyphenbutazone, feprazone, azapropazone, trimethazone); and combinations thereof as well as any dermatologically acceptable salts or esters of thereof. COX-2 inhibitors are also suitable for use herein, and include, but are not limited to, AZD 3582 (Astrazeneca and NicOx), Celecoxib (Pharmacia Corp.) (4-[5-(4-methylphenyl)-3-(trifluoromethyl)-1H-pyrazol-1-yl] benzenesulfonamide), Meloxicam (Boehringer Ingelheim Pharmaceuticals) (4-hydroxy-2-methyl-N-(5-methyl-2-thiazolyl)-2H-1,2GW-406381 (Glaxosmithkline), Etoricoxib (Merck & Co.), Rofecoxib (MERCK & Co.) (4-[4-(methylsulfonyl) phenyl]-3-phenyl-2(5H)-furanone), Lumiracoxib (Novartis Pharma AG), Valdecoxib (Pharmacia Corp.) (4-(5-methyl-3-phenyl-4-isox-azolyl) benzenesulfonamide), and Etodolac (Wyeth Ayerst Laboratories) ((±) 1,8-diethyl-1,3,4,9-tetrahydropyrano-[3,4-b]acid).

An anti-inflammatory agent also includes, without limitation, candelilla wax, bisabolol (e.g., α-bisabolol), aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, sea whip extract, anise oil, garlic oil, ginger extract, vasoconstrictors such as phenylephrine hydrochloride, compounds of the Licorice (the plant *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, preferably $C_{10}$-$C_{24}$, more preferably $C_{16}$-$C_{24}$. Specific non-limiting examples of the foregoing include oil soluble licorice extract, the glycyrrhizic and glycyrrhetic acids themselves, mono ammonium glycyrrhizinate, monopotassium glycyrrhizinate, dipotassium glycyrrhizinate, 1-β-glycyrrhetic acid, stearyl glycyrrhetinate, 3-stearyloxy-glycyrrhetinic acid, disodium 3-succinyloxy-β-glycyrrhetinate, and combinations thereof.

Aspects of the present specification disclose an anti-lice agent. An anti-lice agent includes, without limitation, include organochlorines, such as, e.g., lindane, organophosphates, such as, e.g., malathion, carbamates, such as, e.g., carbaryl, pyrethrins, such as, e.g., pyrethrum, pyrethroids, such as, e.g., permethrin, phenothrin, bioallethrin, and spinosad, such as, e.g., spinosyn A and spinosyn D, bactrim, benzyl alcohol, crotamiton, dimeticone and ivermectin.

Aspects of the present specification disclose an anti-microbial agent. An anti-microbial agent includes, without limitation, anti-bacterial, anti-septic, anti-fungal, anti-parasitic, and anti-viral compounds.

Anti-bacterials include, without limitation, an aminoglycoside, a tetracycline, a glycylcycline, a fluorocycline, an oxazolidinone, a peptidyl transferase (like an amphenicol and a pleuromutilin), a macrolide, a lincosamide, a streptogramin, a steroid antibacterial, a β-lactam (like a penicillin, a penem, a carbapenem, a cephem, a monobactam and a β-lactamase inhibitor), an antifolates (like a dihydrofolate reductase (DHFR) inhibitor, a sulphonamide, a topoisomerase inhibitor, diaminodiphenyl sulfone and a quinolone), an anaerobic DNA inhibitor (like a nitroimidazole derivative, a nitrofuran derivative and a rifamycin). Antiseptics include, without limitation, an acridine compound (like ethacridine lactate, 9-Aminoacridine and euflavine), a biguanide compound, an amidine compound (like 1,8-Diazabicyco[5.4.0]Undec-7-ene (DBU), diminazene, and benzamidine, chlorhexidine, dibrompropamidine, propamidine and hexamidine), a phenol compound (like hexachlorophene, policresulen, phenol, triclosan, triclocarban, chloroxylenol, biphenylol, fenticlor and bisbiguanides, e.g. chlorhexidene gluconate), a nitrofuran compound (like nitrofurazone), an iodine compound (iodine/octylphenoxypolyglycolether, povidone-iodine, diiodohydroxypropane and an iodophor), a quinoline compound (like dequalinium, chlorquinaldol, qxyquinoline and clioquinol), a quaternary ammonium compound (like benzalkonium, benzethonium chloride, betrimonium, cetylpyridinium, cetrimide, benzoxonium chloride and didecyldimethylammonium chloride), a mercurial compound (like mercuric amidochloride, phenylmercuric borate, mercuric chloride, merbromin, thiomersal, mercuric iodide), a silver compound (like silver nitrate), an alcohol (like propanol, isopropanol, ethanol and other antiseptics like potassium permanganate, sodium hypochlorite, mafenide acetate, nitromersol, hydrogen peroxide, eosin, tosylchloramide and octenidine dihydrochloride.

In a further embodiment, anti-microbial with anti-fungal actives include, without limitation, β-lactam compounds, imidazole compounds, quinolone compounds, 2,4,4'-trichloro-2'-hydroxy diphenyl ether, 3,4,4'-trichlorocarbanilide, amanfadine, amanfadine hydrochloride, amanfadine sulfate, amikacin, amikacin sulfate, benzoic acid, benzoperioxide, butenafine, butocouazole nitrate, capreomycin, capreomycin sulfate, chlorhexidine, chlorhexidine gluconate, chlorhexidine hydrochloride, chlortetracycline, chlortetracycline hydrochloride, ciclopirox, ciprofloxacin, clindamycin hydrochloride, clotrimazole, doxycycline, doxycycline hydrochloride, econazole, efinaconazole, erythromycin, erythromycin estolate, erythromycin stearate, ethambutol, ethambutol hydrochloride, gentamicin, gentamicin sulfate, haloprogin, hexamidine isethionate, kanamycin, kanamycin sulfate, ketoconazole, lineomycin, lineomycin hydrochloride, luliconazole, methacycline, methacycline hydrochloride, methenamine, methenamine hippurate, methenamine mandelate, metronidazole, metronidazole hydrochloride, miconazole, miconazole hydrochloride, minocycline, minocycline hydrochloride, naftifine, neomycin, neomycin sulfate, netilmicin, netilmicin sulfate, norfloxacin, nystatin, octopirox, oxiconazole, oxytetracycline, parachlorometa xylenol, paromomycin, paromomycin sulfate, phenoxyethanol, phenoxy propanol, phenoxyisopropanol, pentamidine, pentamidine hydrochloride, paromomycin, salicylic acid, sertaconazole, streptomycin, streptomycin sulfate, sulconazole, tavaborole, terbinafine, tetracycline, tetracycline hydrochloride, tobramycin, tobramycin sulfate, tolnaftate, undecylenic acid, butocouazole phenol-TEA complex, mupirocin, triclosan, chlorocresol, chlorbutol, iodine, clindamycin, CAE (Anjinomoto Co., Inc., containing DL-pyrrolidone carboxylic acid salt of L-Cocoyl Arginine Ethyl Ester), povidone-iodine, polyhexanide, polyhexamethylene biguanide, polymyxin b sulfate-bacitracin, zinc-neomycin sulfate-hydrocortisone, zinc oxytetracycline hydrochloride, zinc pyrithione, chloramphenicol, methylbenzethonium chloride, manuka honey and erythromycin.

An antiparasitic agent includes, without limitation, lindane and the like may be included in a composition disclosed herein.

An anti-viral agent includes, without limitation, acyclovir, peniciclovir, metal salts (e.g., silver nitrate, copper sulfate, iron chloride, etc.) and organic acids (e.g., malic acid, salicylic acid, succinic acid, benzoic acid, etc.). In particular compositions which contain additional suitable anti-viral agents include those described in copending U.S. patent application Ser. No. 09/421,084 (Beerse et al.); Ser. No. 09/421,131 (Biedermann et al.); Ser. No. 09/420,646 (Morgan et al.); and Ser. No. 09/421,179 (Page et al.), which were each filed on Oct. 19, 1999.

Additional antimicrobial agents are described in, e.g., U.S. Pat. Nos. 6,827,795; 6,517,854; 6,010,817; 5,173,216; 5,719,113; 5,259,984; 5,562,912; 5,629,006; 5,728,662; 5,767,163; 5,750,579; 5,591,442; 5,650,143; 5,772,640; and 4,478,821, each of which is hereby incorporated by reference in its entirety.

Aspects of the present specification disclose an anti-oxidant agent. An anti-oxidant includes, without limitation, propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Vitamin A, vitamin E, coenzyme Q-10, ascorbic acid and its salts, ascorbyl esters of fatty acids, ascorbic acid derivatives (e.g., magnesium ascorbyl phosphate, sodium ascorbyl phosphate, ascorbyl sorbate), tocopherol, tocopherol acetate, other esters of tocopherol, tocotrienols and their esters, and 6-hydroxy-2,5,7,8-tetramethylchroman-2-carboxylic acid (commercially available under the tradename TROLOX). Other suitable anti-oxidants include uric acid and its salts and alkyl esters, sorbic acid and its salts, lipoic acid, amines (e.g., N,N-diethylhydroxylamine, amino-guanidine), sulfhydryl compounds (e.g., glutathione, N-acetyl cysteine), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts, and a cascading anti-oxidant, such as, e.g., EMBLICA® (EMD Chemicals) and synovia.

Aspects of the present specification disclose an anti-pruritic agent. An anti-pruritic agent includes, without limitation, alclometasone dipropionate, betamethasone valerate, and isopropyl myristate MSD.

Aspects of the present specification disclose an anti-skin aging agent. An anti-skin aging agent or anti-wrinkling agent includes, without limitation, a variety of agents, often in combination, that prevent or treat wrinkling through a variety of actions, including, without limitation, cosmetic products that contain hydroxy acids, retinol, retinoic, retinol palmitate, a derivative of vitamin A, (or its stronger, prescribed version Retin-A and Renova), bicyclic aromatic compounds with retinoid-type activity, including, without limitation, those described in EP 679 630. An anti-skin aging agent or anti-wrinkling agent includes, without limitation, bicyclic aromatic compounds, compounds which have retinoid-type activity, free-radical scavengers, a hydroxy acid, a keto acid or derivatives thereof. A "free-radical scavenger" includes, without limitation, α-tocopherol, superoxide dismutase, ubiquinol or certain metal-chelating agents. A hydroxy acid includes, without limitation, α-hydroxy acids such as lactic acid and glycolic acid or β-hydroxy acids such as salicylic acid and salicylic acid derivatives such as the octanoyl derivative; other hydroxy acids and keto acids include, without limitation, malic, citric, mandelic, tartaric or glyceric acids or the salts, amides or esters thereof. An anti-wrinkling agent and anti-skin aging agent include, without limitation, sulfur-containing D and L amino acids and their derivatives and salts, particularly the N-acetyl derivatives, a preferred example of which is N-acetyl-L-cysteine; thiols, e.g. ethane thiol; fat-soluble vitamins, ascorbyl palmitate, ceramides, pseudoceramides (e.g., pseudoceramides described in U.S. Pat. Nos. 5,198,210; 4,778,823; 4,985,547; 5,175,321, each of which is hereby incorporated by reference in its entirety), phospholipids (e.g., distearoyl lecithin phospholipid), fatty acids, fatty alcohols, cholesterol, plant sterols, phytic acid, lipoic acid; lysophosphatidic acid, and skin peel agents (e.g., phenol and the like), and mixtures thereof. A fatty acid and/or fatty acid alcohol include, without limitation, straight or branched alkyl chains containing 12-20 carbon atoms and linoleic acid. In a further embodiment, anti-wrinkle actives include, without limitation, those described in U.S. Pat. No. 6,217,888, which is incorporated herein by reference in its entirety.

Aspects of the present specification disclose a deodorant. A deodorant includes, without limitation, aluminium bromohydrate, potassium alum, sodium aluminium chlorohydroxy lactate, aluminium sulfate, aluminium chlorohydrate, aluminium-zirconium tetrachlorohydrate, an aluminium-zirconium polychlorohydrate complexed with glycine, aluminium-zirconium trichlorohydrate, aluminium-zirconium octachlorohydrate, aluminium sesquichlorohydrate, aluminium sesquichlorohydrex PG, aluminium chlorohydrex PEG, aluminium zirconium octachlorohydrex glycine complex, aluminium zirconium pentachlorohydrex glycine complex, aluminium zirconium tetrachlorohydrex glycine complex, aluminium zirconium trichlorohydrex glycine complex, aluminium chlorohydrex PG, zirconium chlorohydrate, aluminium dichlorohydrate, aluminium dichlorohydrex PEG, aluminium dichlorohydrex PG, aluminium sesquichlorohydrex PG, aluminium chloride, aluminium chloride hexahydrate, aluminium zirconium pentachlorohydrate, methylbenzethonium chloride, chlorophyllin copper complex and numerous other useful antiperspirant compounds listed in the CTFA Handbook at p. 56, incorporated herein by reference, and mixtures thereof.

A deodorant also includes, without limitation, astringent salts and bioactive compounds. An astringent salt includes, without limitation, organic and inorganic salts of aluminium, zirconium, zinc, and mixtures thereof. Anions of the astringent salt include, without limitation, sulfate, chloride, chlorohydroxide, alum, formate, lactate, benzyl sulfonate or phenyl sulfonate. An antiperspirant astringent salt includes, without limitation, aluminium halides, aluminium hydroxyhalides, zirconyl oxyhalides, zirconyl hydroxyhalides, and mixtures thereof. An aluminium salt includes, without limitation, aluminium chloride and the aluminium hydroxyhalides having the general formula $Al_2(OH)_xQ_yXH_2O$, wherein Q is chlorine, bromine or iodine; x is about 2 to about 5; x+y is about 6, wherein x and y are not necessarily integers; and X is about 1 to about 6. A zirconium compound includes, without limitation, zirconium oxy salts and zirconium hydroxy salts, also referred to as zirconyl salts and zirconyl hydroxy salts, and represented by the general empirical formula $ZrO(OH)_2 2\text{-nz } L_z$, wherein z varies from about 0.9 to about 2 and is not necessarily an integer; n is the valence of L; 2-nz is greater than or equal to 0; and L is selected, without limitation, from the group consisting of halides, nitrate, sulfamate, sulfate, and mixtures thereof.

A deodorant also includes, without limitation, a bacteriostatic quaternary ammonium compound, such as, e.g., cetyl trimethyl ammonium bromide, cetyl pyridinium chloride, benzethonium chloride, diisobutylbenzoxyethoxyethyldimethylbenzyl ammonium chloride, sodium N-lauryl sarcosine, sodium N-polymethyl sarcosine, lauroyl sarcosine, N-myristolyl glycine, potassium N-lauroyl sarcosine, and stearyl trimethyl ammonium chloride; or a bioactive compound; or a carbonate or bicarbonate salt, such as, for example, the alkali metal carbonates and bicarbonates, and the ammonium and tetralkylammonium carbonates and bicarbonates.

Aspects of the present specification disclose a hair growth promoter. In an embodiment, examples of actives suitable for treating hair loss include, without limitation, potassium channel openers or peripheral vasodilators such as minoxidil, diazoxide, and compounds such as N*-cyano-N-(tert-pentyl)-N'-3-pyridinyl-guanidine ("P-1075") as disclosed in U.S. Pat. No. 5,244,664, which is incorporated herein by reference; vitamins, such as vitamin E and vitamin C, and derivatives thereof such as vitamin E acetate and vitamin C palmitate; hormones, such as erythropoietin, prostaglandins, such as prostaglandin El and prostaglandin F2-α; fatty acids, such as oleic acid; diuretics such as spironolactone; heat shock proteins ("HSP"), such as HSP 27 and HSP 72; calcium channel blockers, such as verapamil HCL, nifedipine, and diltiazemamiloride; immunosuppressant drugs, such as cyclosporin and Fk-506; 5 α-reductase inhibitors such as finasteride; growth factors such as, EGF, IGF and FGF; transforming growth factor β; tumor necrosis factor; non-steroidal anti-inflammatory agents such as benoxaprofen; retinoids such as tretinoin; cytokines, such as IL-6, IL-1α, and IL-1β; cell adhesion molecules such as ICAM; glucorcorticoids such as betametasone; botanical extracts such as aloe, clove, ginseng, rehmannia, swertia, sweet orange, zanthoxylum, Serenoa repens (saw palmetto), Hypoxis rooperi, stinging nettle, pumpkin seeds, and rye pollen; other botanical extracts including sandlewood, red beet root, chrysanthemum, rosemary, burdock root and other hair growth promoter activators which are disclosed in DE 4330597 which is incorporated by reference in its entirety herein; homeopathic agents such as Kalium Phosphoricum D2, Azadirachta indica D2, and Joborandi DI; genes for cytokines, growth factors, and male-pattered baldness; antifungals such as ketoconazole and elubiol; antibiotics such as streptomycin; proteins inhibitors such as cycloheximide; acetazolamide; benoxaprofen; cortisone; diltiazem; hexachlorobenzene; hydantoin; nifedipine; penicillamine; phenothaiazines; pinacidil; psoralens, verapamil; zidovudine; α-glucosylated rutin having at least one of the following rutins: quercetin, isoquercitrin, hespeddin, naringin, and methylhesperidin, and flavonoids and transglycosidated derivatives thereof which are all disclosed in JP 7002677, which is incorporated by reference in its entirety herein; and mixtures thereof. Preferred hair loss treatment agents include minoxidil, 6-(I-piperdinyl)-2,4-pyrimidinediamine-3-oxide, N'-cyano-N-(tert-pentyl)-N'-3-pyridinyl-guanidine, finasteride, retinoids and derivatives thereof, ketoconazole, elubiol or mixtures thereof.

Aspects of the present specification disclose a hair bleaching agent. A hair bleaching agent includes, without limitation, a perborate salt or a persulfate salt. A hair growth inhibiting agent includes, without limitation, serine proteases such as trypsin; vitamins such as α-tocophenol (vitamin E) and derivatives thereof such as tocophenol acetate and tocophenol palmitate; antineoplastic agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon α, interferon α-2a and interferon α-2b; retinoids, such as retinol (vitamin A), isotretinoin: glucocorticoids such as betamethasone, and dexamethosone; antihyperlipidaemic drugs, such as triparanol and clofibrate; thallium; mercury; albendazole; allopurinol; amiodarone; amphetamines; androgens; bromocriptine; butyrophenones; carbamazepine; cholestyramine; cimetidine; clofibrate; danazol; desipramine; dixyrazine; ethambutol; etionamide; fluoxetine; gentamicin, gold salts; hydantoins; ibuprofen; impramine; immunoglobulins; indandiones; indomethacin; intraconazole; levadopa; maprotiline; methysergide; metoprolol; metyrapone; nadolol; nicotinic acid; potassium thiocyanate; propranolol; pyridostimine; salicylates; sulfasalazine; terfenadine; thiamphenicol; thiouracils; trimethadione; troparanol; valproic acid; and mixtures thereof. Preferred hair growth inhibitory agents include serine proteases, retinol, isotretinoin, betamethoisone, α-tocophenol and derivatives thereof, or mixtures thereof.

Aspects of the present specification disclose a fragrance. A fragrance includes, without limitation, alcohols (e.g., furaneol, 1-hexanol, cis-3-hexen-1-ol, menthol, or the like); aldehydes (e.g., acetaldehyde, hexanal, cis-3-hexenal, furfural, or the like); esters (e.g., fructone, hexyl acetate, ethyl methylphenylglycidate, methyl formate, methyl acetate, methyl butyrate, methyl butanoate, ethyl acetate, ethyl butyrate, ethyl butanoate, isoamyl acetate, pentyl butyrate, pentyl butanoate, pentyl pentanoate, benzoin, black, cajuput oil, caraway, carrot seed, coriander, cypress, dill, fennel, helichyrsum, lavandin, lemon verena, bee balm, niaouli, palmarosa, petitgrain, tagetes, vetiver, or the like); ketones (e.g., dihydrojasmone, oct-1-en-3-one, 2-acetyl-1-pyrroline, 6-acetyl-2,3,4,5-tetrahydropyridine, or the like); lactones (e.g., γ-decalactone, γ-nonalactone, δ-octalactone, massoia lactone, sotolon, or the like); thiols (e.g., ethanethiol, grapefruit mercaptan, methanethiol, 2-methyl-2-propanethiol, or the like); linear terpenes (e.g., myrcene, geraniol, nerol, citral, lemonal, geranial, neral, citronellal, citronellol, linalool, nerolidol, or the like); cyclic terpenes (e.g., limonene, camphor, terpincol, ionone, thujuon, or the like); aromatic species (e.g., benzaldehyde, eugenol, cinnamaldehyde, ethyl maltol, vanillin, anisole, anethole, estragole, thymol, or the like); amines (e.g., thiethylamine, trimethylamine, cadaverine, pyridine, indole, skatole, or the like); or the like, or a combination comprising at least one of the foregoing fragrant molecules.

Further examples of fragrant molecules are geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzyl carbinol, trichloromethylphenylcarbinyl acetate, p-tert-butyl-cyclohexyl acetate, isononyl acetate, vetiveryl acetate, vetiverol, α-n-amylcinammic aldehyde, α-hexylcinammic aldehyde, 2-methyl-3-(p-tert-butylphenyl)-propanol, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyletetrahydropyran, methyl-dihydrojasmonate, 2-n- heptylcyclopentanone, 3-methyl-2-pentylcyclopentanone, n-decanal, 9-decenol-I, phenoxyethyl isobutyrate, phenylacetaldehyde dimethyl acetal, phenylacetaldehyde diethyl acetal, geranonitrile, citronellonitrile, cedryl acetate, 3-isocamphycyclohexanol, cedryl methyl ether, isolongifolanone, aubepine nitrile, aubepine, heliotropine, coumarin, eugenol, vanillin, diphenyl oxide, hydroxycitronellal, ionones, methylionones, isomethyliniones, irones, cis-3-hexenol and esters thereof, indane musk, tetralin musk, isochroman musk, macrocyclic ketones, macrolactone musk, ethylene brassylate, aromatic nitro-musk. Exemplary fragrant molecules include bergamot oil, coriander oil, dimethyl heptanol, dimethyl benzyl carbinyl acetate, geranyl acetate, citronellyl acetate, rose synthetic, geranium bourbon, hedione, iso eugenol, methyl eugenol styrallyl acetate, stemone, rose oxide laevo, aldehyde C-II undecyclic, derivatives of 2,6-dimethyl-2-alkoxy octan-7-ol, vertivert oil, vetiverol, vetiveryl, acetate, quaiac wood oil, esters ol-anthranilic acid, benzyl salicylate, benzyl benzoate, oak moss, eugenol, p-tert-butyl cyclohexyl acetate and coumarin.

Aspects of the present specification disclose a camouflage agent. A camouflage agent, includes, without limitation, a UV reflector, a UV absorber, an infrared (IR) reflector and an IR absorber. A UV reflector reflects wavelengths from about 10 nm to about 400 nm.

An UV absorber aborbs wavelengths from about 10 nm to about 400 nm. Non-limiting examples of a UV absorber include an acrylate dye, a benzotriazole dye, a benzophenone dye and a phosphite dye. Specific UV absorber compounds include, without limitation, 2,4-dihydroxy benzophenone, 2,4-dihydroxybenzophenone, 2-hydroxy-4-methoxybenzophenone, 2,2'-dihydroxy-4,4'-dimethoxybenzophenone, 2,2',4,4'-tetrahydroxybenzophenone, 2-hydroxy-4-dodecyloxybenzophenone, 2-hydroxy-4-octyloxybenzophenone, 2-hydroxy-4-methoxybenzophenone, ethyl-2-cyano-3,3-diphenylacrylate, 2-ethylhexyl-2-cyano-3,3-diphenylacrylate, 2-ethylhexyl-2-cyano-3,3-diphenylacrylate, 2-hydroxy-4-methyoxy-benzophenone-5-sulfonic acid, 2,2'-dihydroxy-4,4'dimethoxy-5-sulfobenzophenone, 2-(2-hydroxy-5-methyl-phenyl)-2H-benzotriazole, 2-(2-hydroxy-5-carboxy-phenyl)-2H-benzotriazole, N-(p-ethoxycarbonylphenyl)-N'-ethyl-N'-phenylformamidine, poly-phenolic phosphite and tris (2,4-di-t-butylphenyl) phosphite.

An IR reflector reflects wavelengths from about 700 nm to about 1500 nm. Non-limiting examples of an IR reflector include a metal oxide. Specific IR reflector compounds include, without limitation, an iron oxide, a titanium dioxide and a zinc oxide or any combination thereof, for example.

An IR absorber aborbs wavelengths from about 700 nm to about 1500 nm. Non-limiting examples of an IR absorber include an azo dye, a croconium dye, a diphenylmethane dye, a heptamethinecyanine dye, a metal complex dye, a naphthalocyanine dye, a photchromic dye, a phthalocynine dye, a polymethine dye, a pyrylium dye, a quinone dye, a squarylium dye and a triphenylmethane dye. A metal complex dye includes, without limitation, a dithiolene metal complex, an indoanilinetype metal complex and a phenylenediamine metal complex. Specific IR absorber compounds include, without limitation, 2-[2-[2-Chloro-3-[(1,3-dihydro-1,3,3-trimethyl-2H-indol-2-ylidene)ethylidene]-1-cycloxen-1-yl]-ethenyl]-1,3,3-trimethyl-3H indolium iodide, 2-[2-[2-Chloro-3-[(1,3-dihydro-1,3,3-trimethyl-2H-indol-2-ylidene)ethylidene]-1-cycloxen-1-yl]-ethenyl]-1,3,3-trimethyl-1H indolium perchlorate, 2-[2-[2-Chloro-3-[(1, 3-dihydro-3,3-dimethyl-1-propyl-2H-indol-2-ylidene) ethylidene]-1-cycloxen-1-yl]-ethenyl]-3,3-dimethy-1-propyl-1H-indolium iodide, 2-[2-[2-Chloro-3-[(1,3-dihydro-3,3-dimethyl-1-propyl-2H-indol-2-ylidene) ethylidene]-1-cycloxen-1-yl]-ethenyl]-3,3-dimethy-1-propyl-1H-indolium perchlorate, 2-[2-[2-Chloro-3-[(1,3-dihydro-3,3-dimethyl-1-(2-hydroxyethyl)-2H-indol-2-ylidene)ethylidene]-1-cycloxen-1-yl]-ethenyl]-3,3-dimethy-1-(2-hydroxyethyl)-1H-indolium perchlorate, 2-[2-[3-[2-(1, 3-Dihydro-1,3,3-trimethyl-2H-indol-2-ylidene)-ethylidene]-2-(1-phenyl-1H-tetrazol-5-ylsulfanyl)-1-cyclohexen-1-yl]-ethenyl]-1,3,3-trimethyl-3H-indolium chloride, 2-[2-[2-(4-Methylbenzeneoxy)-3-[2-(1,3-dihydro-1,1,3-trimethyl-2H-benz[e]indol-2-yilidene)ethylidene]-1-cylohexen-1-yl]-ethenyl]-1,1,3-trimethyl-1H-benz[e]indolium 4-methylbenzenesulfonate, 2-[2-[2-chloro-3-[2-(1,3-dihydro-3,3-dimethyl-1-ethyl-2H-benz[e]indol-2-ylidene) ethylidene]-1-cylohexen-1-yl]-ethenyl]-3,3-dimethyl-1-ethyl-1H-benz[e]indolium iodide, 2-[2-[2-chloro-3-[2-(1,3-dihydro-1,1,3-trimethyl-2H-benz[e]indol-2-ylidene) ethylidene]-1-cylohexen-1-yl]-ethenyl]-1,1,3-trimethyl-1H-benz[e]indolium 4-methylbenzenesulfonate, 1,4-Benzenediamine,N,N-bis[4-(dibutylamino)phenyl]-N',N'-diethykradical ion (2+), bis [hexafluoroantimonate (1-)], 4,4',4''-tris(N,N-phenyl-3-methylphenylamino)triphenylammonium hexafluoroantimonate, 2-[2-[2-Chloro-3-[2-(1,3-dihydro-3,3-dimethyl-1-(4-sulfobutyl)-2H-indol-2-ylidene)-ethylidene]-1-cyclohexen-1-yl]-ethenyl]-3,3-dimethyl-1-(4-sulfobutyl)-1H-indolium, 2-[7-(1,3-Dihydro-3,3-dimethy-1-(4-sulfobutyl)I-2H-benz[e]indol-2-ylidene)-1,3,5-heptatrienyl]-3,3-dimethyl-1-(4-sulfobutyl)-1H-benz[e]indolium, 2-[2-[2-(4-aminobenzenethio)-3-[(1,3-dihydro-3, 3-dimethyl-1-(4-sulfobutyl)-2H-indol-2-ylidene)-ethylidene]-1-cycloxen-1-yl]-ethynyl]-3,3-dimethyl-1-(4-sulfobutyl)-3H-indolium, 2-[2-[2-Chloro-3-[2-(3-(4-sulfobutyl)-3H-benzothiazol-2-ylidene)-ethylidene]-1-cyclohexen-1-yl]-ethenyl]3-(4-sulfobutyl)benzothiazolium, 2-[2-[2-Chloro-3-[2-(1,3-dihydro-3,3-dimethyl-1-(4-sulfobutyl)-2H-benz[e]-indol-2-ylidene)-ethylidene]-1-cyclohexen-1-yl]-ethenyl]-3,3-dimethyl-1-(4-sulfobutyl)-1H-benz[e]indolium, 2-2-[2-[2-(4-aminothiophenyl)-3-[[1,3-dihydro-1,1-dimethyl-3-(4-sulfobutyl)-2H-benz[e]-indol-2-ylidene]ethylidene]-1-cyclohexen-1-yl]ethenyl]-1,1-dimethyl-3-(4-sulfonyl)-, tetrabutylammonium bis(3,6-dichloro-1,2-benzene-dithiolato)nickelate, tetrabutylammonium bis(3,4,6-trichloro-1,2-benzene-dithiolato)nickelate, tetrabutylammonium bis(4-methyl-1,2-benzenedithiolato) nickelate and Bis(4,4'-dimethoxydithiobenzyl) nickel. Other IR absorbers are described in Matsuoka, INFRARED ABSORBING DYES, pp. 220 (Springer Science & Business Media, 1990), which is hereby incorporated by reference in its entirety.

Aspects of the present specification disclose a colorant. A colorant, includes, without limitation, an agent used to color skin, nail, hair or another surface. A colorant, includes, without limitation, aluminum powder, annatto, bismuth citrate, bismuth oxychloride, bronze powder, caramel, carmine, β-carotene, chromium hydroxide green, chromium oxide green, copper powder, dihydroxyacetone, disodium EDTA-copper, ferric ammonium, ferrocyanide, ferric ferrocyanide, guaiazulene, guanine, henna, iron oxide, lead acetate, luminescent zinc sulfide, manganese violet, mica, potassium sodium copper chlorophyllin (chlorophyllin-copper complex), pyrophyllite, silver, titanium dioxide, ultramarine, zinc oxide, D&C Black No. 2, D&C Black No. 3, FD&C Blue No. 1, D&C Blue No. 4, D&C Brown No. 1, FD&C Green No. 3, D&C Green No. 5, D&C Green No. 6, D&C Green No. 8, D&C Orange No. 4, D&C Orange No. 5, D&C Orange No. 10, D&C Orange No. 1 FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, D&C Violet No. 2, Ext. D&C Violet No. 2, FD&C Yellow No. 5, FD&C Yellow No. 6, D&C Yellow No. 7, Ext. D&C Yellow No. 7, D&C Yellow No. 8, D&C Yellow No. 10 and D&C Yellow No. 11.

Aspects of the present specification disclose a jellyfish repellent. A jellyfish repellent agent is used for repelling or preventing stings from members of the phylum Cnidaria (e.g., jellyfish, sea anemone, and coral), the phylum Myxozoa, or the like). A jellyfish repellent agent includes, without limitation, one or both of an antihistamine agent and one or more cations. An antihistamine agent includes, without limitation, diphenhydramine, cimetidine or tripelennamine or other histamine binding inhibitors. In aspects of this embodiment, a jellyfish repellent agent is present in a concentration from about 0.0005% to about 2.0% or from about 0.001% to about 0.2%, or similar effective amount). A cation includes, without limitation, metal cations and alkali cations such as, e.g., $Ca^{++}$, $K^+$, $Na^+$, $Mn^{++}$, $Co^{++}$, $Mg^{++}$, or $Fe^{++}$, or other substance which is capable of supplying positively charged ions. In aspects of this embodiment, a cation is present in a concentration of from about 5 mM to about 1M, or about 25 mM to about 500 mM, or from about 50 mM to about 200 mM.

Aspects of the present specification disclose a medical agent. A medicinal agent is a drug or other substance that has a physiologically or psychologically beneficial effect when administered on, to or into the body. A medicinal agent includes, without limitation, an analgesic, an antibiotic, an anticancer, an anticoagulant, an antidepressant, an antidiabetic, an anti-dieretic, an antiepileptic, an anti-fungal, an anti-inflammatory, an antimicrobial, an antipsychotic, an anti-rheumatic, an anti-thrombotic, an antiviral, a bronchodialator, a chronotrope, a dieretic, a decongestant, a fibrate, an immunosuppressive, an inotrpe, a NSAID, an opioid, a PPAR agonist or antagonist, a statin, a sedative or any other agent classified by the Anatomical Therapeutic Chemical Classification System (ATC) or the systematized nomenclature of medicine (SNOMED).

Non-limiting examples of a medicinal agent include camphor, menthol, benzocaine, butamben picrate, dibucaine, dibucaine hydrochloride, dimethisoquin hydrochloride, dyclonine hydrochloride, lidocaine, metacresol, lidocaine hydrochloride, pramoxine hydrochloride, tetracaine, tetracaine hydrochloride, benzyl alcohol, camphorated metacresol, juniper tar, phenol, phenolate sodium, resorcinol, diphenhydramine hydrochloride, tripelennamine hydrochloride, hydrocortisone, a corticosteroid, and hydrocortisone acetate, burn relief agents, such as o-amino-p-toluenesulfonamide monoacetate; dermatitis relief agents, such as the active steroid amcinonide, diflorasone diacetate, and hydrocortisone; diaper rash relief agents, such as methylbenzethonium chloride and the like; a photochemotherapeutic like aminolevulinic acid, methyl aminolevulinic acid or methoxsalen; a herpes treatment agent, such as O-[(2-hydroxyethoxy)methyl]guanine; psoriasis, seborrhea and scabicide agents, such as shale oil and derivatives thereof, elubiol, ketoconazole, coal tar and petroleum distillates, salicylic acid, zinc pyrithione, selenium sulfide, hydrocortisone, sulfur, menthol, psoralen, pramoxine hydrochloride anthralin, and methoxsalen; steroids, such as Alclometasone, amcinonide, betamethasone, clobetasol, clocortolone, diflorasone, desonide, desoximetasone, fluocinolone, fluocinonide, flurandrenolide, fluticasone, halcinonide, halobetasol, hydrocortisone, mometasone, prednicarbate, triamcinolone, 2-(acetyloxy)-9-fluoro-1',2',3',4'-tetrahydro-11-hydroxy-pregna-1,4-dieno [1 6,17-b]naphthalene-3,20-dione and 21-chloro-9-fluoro-1',2',3',4'-tetrahydro-11 b-hydroxy-pregna-1,4-dieno[16z, 17-b]naphthalene-3,20-dione. Other medicinal agents include, without limitation, ones for treating dermatological conditions such as psoriasis, acne, eczema, keloids, fungal infection, and other skin conditions due to disease, pathology, accident, as well as medicinal agents useful in the treatment of exposure to poison oak, poison ivy, poison sumac, and the like.

In one embodiment, a medicinal agent is a cannaboid. Examples of a cannaboid include, without limitation, a phytocannabinoid, an endocannabinoid, and a synthetic cannabinoid. A Phytocannabinoid includes a Tetrahydrocannabinol (such as, e.g., Delta-9-tetrahydrocannabinol (Δ9-THC, THC), and Delta-8-tetrahydrocannabinol (Δ8-THC)), a Cannabidiol, a Cannabinol, a Cannabigerol, a Tetrahydrocannabivarin, a Cannabidivarin, and a Cannabichromene. An Endocannabinoid includes Arachidonoylethanolamine (Anandamide or AEA), 2-arachidonoyl glycerol (2-AG), 2-arachidonyl glyceryl ether (noladin ether), N-arachidonoyl-dopamine (NADA), Virodhamine (OAE), and Lysophosphatidylinositol (LPI). A synthetic cannabinoid includes Dronabinol (Marinol), Nabilone (Cesamet), Sativex, Rimonabant (SR141716), JWH-018, JWH-073, CP-55940, Dimethylheptylpyran, HU-210, HU-331, SR144528, WIN 55,212-2, JWH-133, Levonantradol (Nantrodolum), and AM-2201.

Aspects of the present specification disclose a skin whitening agent. A skin whitening agent includes, without limitation, skin lightening agent and skin bleaching agent. A skin whitening agent include, without limitation, α-hydroxyl acids ("AHA's"), arbutin, *cinnamomum subavenium*, EMBLICA (also an antioxidant), hydroquinone, kojic acid, azelaic acid, ascorbic acid and derivatives thereof (e.g., magnesium ascorbyl phosphate or sodium ascorbyl phosphate), niacinamide, a licorice extract (e.g., glabridin), a mulberry extract and a placental extract. A skin whitening agent can include a depigmentation agent including, without limitation, monobenzone or mequinol. Additional skin whitening agents are also described in WO 1995/34280, WO 1995/07432, and WO 1995/23780.

Aspects of the present specification disclose a sunless tanning agent. A sunless tanning agent includes, without limitation, dihydroxyacetone (DHA); glyceryl aldehyde; tyrosine and tyrosine derivatives such as, e.g., malyltyrosine, tyrosine glucosinate, and ethyl tyrosine; phospho-DOPA, indoles and derivatives thereof.

Aspects of the present specification disclose a soothing agent. A soothing agent can be a cooling agent or a heating agent. Soothing agents include, without limitation, herb extracts, such as, e.g., aloe vera, α-bisabolol, D-panthenol, allantoin, hamamelis, chamomile, yarrow; calendula, comfrey, witch hazel and other astringents, sea weed, and oat extracts; oils, selected from the group consisting of: almond oil, avocado oil, and comfrey; and essential oils, selected from the group consisting of: cardamone, eucalyptus, *Mentha piperita* (peppermint), hyssop, and rosemary; waxy or unctuous substances selected from the group consisting of: lanolin or petroleum jelly, minerals, selected from the group consisting of: zinc oxide, calamine and selenium; vitamins, selected from the group consisting of: tocopheryl acetate (vitamin E), and pharmaceutical agents selected from the group consisting of: analgesics, anesthetics, anti-inflammatory agents, and anti-histamines, and muscle relaxants; menthol, camphor, eugenol, eucalyptol, safrol, methyl salicylate, menthyl lactate, menthyl ethoxyacetate, menthone glycerinacetal, 3-I-menthoxpropane-1,2-diol, ethyl I-menthyl carbonate, (1S,3S,4R)-p-menth-8-en-3-ol, menthyl pyrrolidone carboxylate, N-substituted-p-menthane-3-carboxamides hamamelis extract and ginger oil.

A cooling agent includes, without limitation, menthol; an isomer of menthol, a menthol derivative (e.g., menthol ethylene glycol carbonate, which is now known as Frescolat® type MGC, menthol Propylene Glycol Carbonate (Frescolat® type MPC), menthyl lactate (Frescolat ML®) and Menthone Glycerin Acetal (Frescolat MGA®) and 3-(1-Menthoxy)-1,2-propanediol); 4-Methyl-3-(1-pyrrolidinyl)-2[5H]-furanone; WS-23, Icilin, Icilin Unilever Analog, 5-methyl-4-(1-pyrrolidinyl)-3-[2H]-furanone; 4,5-dimethyl-3-(1-pyrrolidinyl)-2[5H]-furanone; isopulegol, 3-(I-menthoxy)propane-1,2-diol, 3-(I-menthoxy)-2-methylpropane-1,2-diol, p-menthane-2,3-diol, p-menthane-3,8-diol (Coolact® 38D), 6-isopropyl-9-methyl-1,4-dioxas-piro[4,5]decane-2-methanol, menthyl succinate and its alkaline earth metal salts, trimethylcyclohexanol, N-ethyl-2-isopropyl-5-methylcyclohexanecarb-oxamide, Japanese mint (*Mentha arvensis*) oil, peppermint oil, menthone, menthone glycerol ketal, menthyl lactate, 3-(I-menthoxy)ethan-1-ol, 3-(I-menthoxy)propan-1-ol, 3-(I-menthoxy)butan-1-ol, I-menthylacetic acid N-ethylamide, I-menthyl-4-hydroxypentanoate, I-menthyl-3-hydroxybutyrate, N,2,3-trimethyl-2-(1-methylethyl)-butanamide, spearmint oil and Coolact® 38D.

A heating agent includes, without limitation, polyhydric alcohols, *capsicum* (red pepper) powder, a *capsicum* tincture, *capsicum* extract, capsaicin, homocapsaicin, homodihydrocapsaicin, nonanoyl vanillyl amide, nonanoic acid vanillyl ether, vanillyl alcohol alkyl ether derivatives, such as vanillyl ethyl ether, vanillyl butyl ether, vanillyl pentyl ether, and vanillyl hexyl ether, isovanillyl alcohol alkyl ethers, ethylvanillyl alcohol alkyl ethers, veratryl alcohol derivatives, substituted benzyl alcohol derivatives, substituted benzyl alcohol alkyl ethers, vanillin propylene glycol acetal, ethylvanillin propylene glycol acetal, ginger extract, ginger oil, gingeol, and gingeron.

Aspects of the present specification disclose a vitamin. A vitamin includes, without limitation, Vitamin A and derivatives thereof (including, for example, retinol), ascorbic acid (Vitamin C and derivatives), Vitamin B (e.g., riboflavin, vitamin $B_2$), biotin, Vitamin D (all forms), Vitamin E and derivatives thereof such as tocopheryl acetate, β-carotene, panthothenic acid and more.

Aspects of the present specification disclose a skin care agent. A skin care agent includes, without limitation, those found in the CTFA Cosmetic Ingredient Handbook, Seventh Edition, 1997 and the Eighth Edition, 2000 and Remington's Pharmaceutical Sciences, 20th Ed., Lippincott Williams & Watkins, Baltimore, Md. (2000) (hereinafter Remington's), U.S. Pharmacopeia and National Formulary, The United States Pharmacopeia Convention, Inc., Rockville, Md. and Physician's Desk Reference, Medical Economics Co., Inc., Oradell, N.J. all of which are incorporated herein by reference.

A composition disclosed herein can include any number of active agents. In aspects of this embodiment, a composition disclosed herein may comprise, e.g., at least one, at least two, at least three, at least four, at least five, at least six, at least seven, at least eight, at least nine or at least ten active agents. In other aspects of this embodiment, a composition disclosed herein may comprise, e.g., at most one, at most two, at most three, at most four, at most five, at most six, at most seven, at most eight, at most nine or at most ten active agents. In yet other aspects of this embodiment, a composition disclosed herein may comprise, e.g., about 1 to about 2, about 1 to about 3, about 1 to about 4, about 1 to about 5, about 1 to about 6, about 1 to about 7, about 1 to about 8, about 1 to about 9, about 1 to about 10, about 2 to about 3, about 2 to about 4, about 2 to about 5, about 2 to about 6, about 2 to about 7, about 2 to about 8, about 2 to about 9, about 2 to about 10, about 3 to about 4, about 3 to about 5, about 3 to about 6, about 3 to about 7, about 3 to about 8, about 3 to about 9, about 3 to about 10, about 4 to about 5, about 4 to about 6, about 4 to about 7, about 4 to about 8, about 4 to about 9, about 4 to about 10, about 5 to about 6, about 5 to about 7, about 5 to about 8, about 5 to about 9, about 5 to about 10, about 6 to about 7, about 6 to about 8, about 6 to about 9, about 6 to about 10, about 7 to about 8, about 7 to about 9, about 7 to about 10, about 8 to about 9, about 8 to about 10 or about 9 to about 10 active agents.

A composition disclosed herein comprises one or more active agents disclosed herein in an amount sufficient to promote or facilitate the function or activity of that active agent. The amount of active agent disclosed herein can range from 0.00% to 99.9% by total weight of the composition, or any integer or range in therebetween. In aspects of this embodiment, a composition disclosed herein comprises an active agent in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises an active agent in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises an active agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

A composition comprising silicon dioxide-based particles, like diatomaceous earth-based particles, comprising one or more active agents may further include one or more polymers. A polymer acts as a core stabilizer, providing a stabilizing function that includes retarding or preventing the leakage or release of one or more active agents from silicon dioxide-based particles, like diatomaceous earth-based particles. A polymer can be natural, synthetic or semi-synthetic organic solids that are moldable. A polymer iincludes, without limitation, polymers composed of polyethylene, polyamide, polyethylene terephthalate, polyester, acrylonitrile butadiene styrene, polycarbonate, polyurethane, polypropylene, melamine formadehyde, phenolics, polyetheretherketone, polyetherimide, polylactic acid, polymethyl methacrylate, polytetrafluoroethylene, silicone, urea-formaldehyde, polystyrene, polyvinyl chloride and polytetrafluoroethylene. In an embodiment, a polymer can be biodegradable or not.

A composition comprising one or more active agents may further include one or more other additional components. Generally, an additional component disclosed herein provides a benefit different than or complimentary to the one or more agents, and/or provides a minimally similar benefit. Non-limiting examples of an additional component includes a cationic polymer, a film former, an anti-caking agent, a surfactant metal complex, a chelating agent, a preservative, and a thickening agent. Although they can be contained in and by silicon dioxide particles, additional components are typically not encapsulated.

A cationic polymer to enhance the overall positive charge of the one or more diatomaceous earth-based particles, one or more sol-gel capsules and/or one or more flexible cellulose-derived capsules. The overall net positive charge of particles/encapsulates promote and facilitate an electrostatic binding or attachment of particles/encapsulates to a negatively charged molecule or surface, such as, e.g., charged components of skin and/or hair. Thus, the compositions may also be formulated with cationic polymer in a manner that causes the silicon dioxide-based particles to adhere to or trapped in a polymer complex to a skin surface, hair shaft, or any substrate which can accept an opposing charge forming a protective layer on the skin or other substrate. The positively charged nature of the silicon dioxide-based particle enables the composition to remain on the skin's surface or other surface for longer periods of time relative to conventional compositions without the diatomaceous earth-based particles and its packing capability, even after exposure to water or other liquids. In addition, because the active agent remained with the silicon dioxide-based particle, protection is not lost due to absorption of the active agent into the skin. In an embodiment, a cationic polymer disclosed herein is used to coat the surface of silicone dioxide-based particles, like diatomaceous earth-based particle and/or sol-gel and/or flexible cellulose-derived capsules disclosed herein. In an embodiment, a cationic polymer disclosed herein is not contained in silicone dioxide-based particles, like diatomaceous earth-based particles and/or sol-gel and/or flexible cellulose-derived capsules e disclosed herein.

A cationic polymer useful in a composition disclosed herein include, without limitation, POLYMER JR (Union Carbide Corp.), a cationic diatomaceous earth ether derivative, JAGUAR® (Celanese-Stein Hall), cationic guar gums, GAFQUA™ (GAF Corporation), quaternary vinylpyrrolidone copolymer, CAE (Anjinomoto Co., Inc.), a DL-pyrrolidone carboxylic acid salt of L-cocoyl arginine ethyl ester, and MERQUAT™ (Merck & Co.), including MERQUAT™ 100, a highly charged cationic polymer prepared with dimethyldiallylammonium chloride homopolymer, and MERQUAT™ 550, a highly charged cationic copolymer prepared with dimethyldiallylammonium chloride and acrylamide.

In an embodiment, a cationic polymer includes, without limitation, a quaternium or a polyquaternium. Non-limiting examples of a polyquaternium-1, polyquaternium-2, polyquaternium-4 (CELQUAT L-200), polyquaternium-5, polyquaternium-6, polyquaternium-7, polyquaternium-10, polyquaternium-11, polyquaternium-15, polyquaternium-16, polyquaternium-22, polyquaternium-28, polyquaternium-32, polyquaternium-37, polyquaternium-39, polyquaternium-40, polyquaternium-41, polyquaternium-42, polyquaternium-44, polyquaternium-45, polyquaternium-46, polyquaternium-47 and polyquaternium-64.

A cationic polymer useful in a composition disclosed herein are also described in, e.g., U.S. Pat. Nos. 6,224,852; 3,816,616; 4,272,515; 4,298,494; 4,080,310; 4,048,301; 4,009,256; and 3,186,911, each of which is hereby incorporated by reference in its entirety.

A composition disclosed herein comprises a cationic polymer in an amount sufficient to confer an overall positive charge of the one or more diatomaceous earth-based particles that promotes and facilitates an electrostatic binding or attachment of the particles to a negatively charged molecule or surface, such as, e.g., charged components of skin and/or hair. In aspects of this embodiment, a composition disclosed herein comprises a cationic polymer in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises a cationic polymer in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises a cationic polymer in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

A composition disclosed herein comprises a film former. As used herein, a film former creates a hydrophobic layer on a skin surface and/or hair that acts as a barrier which promotes and enhances the retention of the one or more agents and/or additional components, even after exposure to water or other liquids, such as, e.g., by washing, rinsing, or swimming. A film former disclosed herein is not contained in a diatomaceous earth-based particle. Non-limiting examples of a film former include an acrylic copolymer, butylated hydroxytoluene (BHT), dimethicone, a lanolin derivative, petrolatum, a polyethylene, a polymer, a silicon derivative, a superfatted oil, a water-insoluble emollient, and a keratin or other protein derivative in an amino acid complex such as cysteine. In an embodiment, a film former disclosed herein is used to coat the surface of silicone dioxide-based particles, like diatomaceous earth-based particle and/or sol-gel and/or flexible cellulose-derived capsules disclosed herein. In an embodiment, a film former disclosed herein is not contained in silicone dioxide-based particles, like diatomaceous earth-based particles and/or sol-gel and/or flexible cellulose-derived capsules e disclosed herein.

Non-limiting examples of a lanolin derivative include, without limitation, an acetylated lanolin.

Non-limiting examples of a water-insoluble emollient include, without limitation, fatty acids such as, e.g., oleic and stearic; fatty alcohols such a as, e.g., s cetyl, and hexadecyl (ENJAY); cocoa butter; shea oil; emollient esters such as, e.g., diisopropyl adipate, benzoic acid esters of $C_9$-$C_{15}$ alcohols, and isononyl iso-nonanoate; alkanes such as, e.g., mineral oil; silicones; such as, e.g., dimethyl polysiloxane and emollient ethers such as, e.g., polyoxypropylene butyl ethers and polyoxypropylene cetyl ethers.

Non-limiting examples of a polyethylene include, without limitation, PERFORMALENE® 400 (New Phase Technologies), a polyethylene having a molecular weight of 400 and PERFORMALENE® 2000 (New Phase Technologies) a polyethylene having a molecular weight of 2000.

Additional non-limiting examples of a film former include acacia gum, diatomaceous earth derivatives, guar derivatives, acrylamides copolymer, acrylamide/sodium aciylate copolymer, acrylate/acrylamide copolymer, acrylate/ammonium methacrylate copolymer, acrylates copolymer, acrylates/diacetoneacrylamide copolymer, acrylic/acrylate copolymer, adipic acid/dimethylaminohydroxypropyl diethlenetnamine copolymer, adipic acid/epoxypropyl/diethlenetriamine copolymer, albumen, allyl stearate/VA copolymer, aminoethylacrylate phosphate/acrylate copolymer, ammonium acrylates copolymer, ammonium alginate, ammonium vinyl acetate/acrylates copolymer, AMP acrylates/diacetoneacrylamide copolymer, balsam canada, balsam oregon, balsam peru, balsam tolu, benzoi acid/phthalic an hydride/pentaerythritol/neopentyl glycol/palmitic acid copolymer, benzoin extract, butadiene/acrylonitrile copolymer, butylated urea-formaldehyde resin, butyl benzoic acid/phthalic anhydride trimethylolethane copolymer, butyl ester of ethylene maleic anhydride copolymer, butyl ester of PVM/MA copolymer, calcium carrageenean, calcium/sodium PVM/MA copolymer, carboxymethyl hydroxyethyl diatomaceous earth, diatomaceous earth gum, collodion, copal, corn starch/aciylainide/sodium acrylate copolymer, damar, diethylene glycolamine/epichlorohydrin/piperazine copolymer, DMJ-IF, dodecanedoic acid/cetearyl alcoholglycol copolymer, ethyldiatomaceous earth, ethylene/acrylate copolymer, ethylene/maleic anhydride copolymer, ethylene/vinyl acetate copolymer, ethyl ester of PVM/fvlA copolymer, flexible collodian, gum benzoin, gutta percha, hydroxybutyl methylceflulose, hydroxyethyldiatomaceous earth, hydroxyethyl ethyl diatomaceous earth, hydroxypropylceilulose, hydroxypropyl guar, hydroxypropyl methyldiatomaceous earth, isopropyl ester of PVM/MA copolymer, maltodextrin, melamine/formaldehyde resin, methacryloyl ethyl betainelmethacrylates copolymer, nitrodiatomaceous earth, octylacrylamide/acrylates/butylaminoethylmethaciylate copolymer, octylacrylamide/acrylates copolymer, phthalic anhydride/glycerin/gycidyl decanoate copolymer, phthalic/trimellitic/glycols copolymer, polyacrylamide, polyaciylamidomethylpropane sulfone acid, polyacrylic acid, polybutylene terephthalate, polychlorotrifluoroethylene, polyethylacrylate, polyethylene, polyethylene terephthalate, polyisobutene, polystyrene, polyvinyl acetate, polyvinyl alcohol, polyvinyl butyral, polyvinyl imidazolinium acetate, polyvinyl laurate, polyvinyl methyl ether, potassium carrageenan, PVM/MA copolymer, PVP, PVP/dimethylaminoethymethacrylate copolymer, PVP/eicosene copolymer, PVP/ethyl methacrylate/methacrylic acid copolyerm, PVP/hexadecene copolymer, PVP/VA copolymer, PVP/vinyl acetate/itaconic acid copolymer, rosin, serum albumin, shellac, sodium acrylate/vinyl alcohol, copolymer, sodium carrageen, sodium polymethacrylate, sodium polystyrene sulfonate, starch/acrylates/acrylamide copolymer, starch diethylaminoethyl ether, steaxyvinyl ether/maleic anhydride copolymer, styrene/acrylate/acrylonitrile copolymer, styrene/acrylate/ammonium methacrylate copolymer, styrene/maleic anhydride copolymer, styrene/PVP copolymer, sucrose benzoate/sucrose acetate isobutyrate/butyl benzyl phthalate copolymer, sucrose benzoate/sucrose acetate isobutyrate/butyl benzyl phthalate/methyl methaciylate copolymer, sucrose benzoate/sucrose acetate isobutyrate copolymer, toluenesulfonamide/formaldehyde resin, tragacath gum, vinyl acetate/crotonates copolymer, vinyl acetate/crotonic acid copolymer, vinyl acetate/crotonic acid/methacryloxybenzophenon-1 copolymer, vinyl acetate/crotonic aid/vinyl neodecanoate copolymer, and zein (a class of prolamine protein).

A film former useful in a composition disclosed herein include, without limitation, petroleum, an acrylate copolymer (DERMACRYL® 2.0, DERMACRYL® 79, DERMACRYL® AQF, DERMACRYL® C, DERMACRYL® E), a synthetic wax of branched polyalpha olefin polymers (PERFORMA® V 103, 260, 343, 825, 6038), a $C_{28}$-$C_{52}$ olefin/undecylenic acid copolymer (PERFORMA® V 6112) or MOISTUREGUARD™ (Engelhard), a film former comprising petrolatum, dimethicone, stearamidopropyl dimethylamine, stearate and tocopheryl acetate. A film former useful in a composition disclosed herein are also described in, e.g., U.S. Pat. Nos. 6,838,419, 6,838,088, 6,780,422, 6,531,118, and 5,916,541, each of which is incorporated herein by reference in its entirety.

A composition disclosed herein comprises a film former in an amount sufficient to create a hydrophobic layer on a skin surface and/or hair that acts as a barrier which promotes and enhances the retention of the one or more agents and/or additional components, even after exposure to water or other liquid. In aspects of this embodiment, a composition disclosed herein comprises a film former in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25%, at least 30%, at least 35% or at least 40% of the total weight of the composition. In other aspects of this embodiment, a composition disclosed herein comprises a film former in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25%, at most 30%, at most 35% or at most 40% of the total weight of the composition.

In other aspects of this embodiment, a composition disclosed herein comprises a film former in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19%, about 5.0% to about 20%, about 5.0% to about 25%, about 5.0% to about 30%, about 10% to about 15%, about 10% to about 20%, about 10% to about 25%, about 10% to about 30%, about 10% to about 35%, about 10% to about 40%, about 15% to about 20%, about 15% to about 25%, about 15% to about 30%, about 15% to about 35%, about 15% to about 40%, about 20% to about 25%, about 20% to about 30%, about 20% to about 35% or about 20% to about 40% of the total weight of the composition.

In an embodiment, a composition disclosed herein comprises can further comprise an anti-caking agent to retard or prevent the agglomeration of silicon dioxide-derived particles, such as diatomaceous earth-based particles disclosed herein. An anti-caking agent disclosed herein is not contained by a silicon dioxide-derived particle, such as a diatomaceous earth-based particle, as disclosed herein. Non-limiting examples of anti-caking agents include fumed silica and calcium silicate. Typically, an anti-caking agent is added in an amount of about 0.2% to about 5%. In aspects of this embodiment, a composition disclosed herein comprises an anti-caking agent in an amount of, e.g., about 0.2%, at least about 0.5%, about 1%, about 2%, about 3%, about 4% or about 5%. In other aspects of this embodiment, a composition disclosed herein comprises an anti-caking agent in an amount of, e.g., at least 0.2%, at least 0.5%, at least 1%, at least 2%, at least 3%, at least 4% or at least 5%. In yet other aspects of this embodiment, a composition disclosed herein comprises an anti-caking agent in an amount of, e.g., at most 0.2%, at most 0.5%, at most 1%, at most 2%, at most 3%, at most 4% or at most 5%. In still other aspects of this embodiment, a composition disclosed herein comprises an anti-caking agent in an amount of, e.g., about 0.2% to about 0.5%, about 0.2% to about 1%, about 0.2% to about 2%, about 0.2% to about 3%, about 0.2% to about 4%, about 0.2% to about 5%, about 0.5% to about 1%, about 0.5% to about 2%, about 0.5% to about 3%, about 0.5% to about 4%, about 0.5% to about 5%, about 1% to about 2%, about 1% to about 3%, about 1% to about 4%, about 1% to about 5%, about 2% to about 3%, about 2% to about 4%, about 2% to about 5%, about 3% to about 4%, about 3% to about 5%, or about 4% to about 5%.

In an embodiment, a composition disclosed herein comprises can further comprise a surfactant metal complex to enhance the reflective property or create a reflective property of a composition disclosed herein. A surfactant metal complex disclosed herein is not contained by a silicon dioxide-derived particle, such as a diatomaceous earth-based particle, as disclosed herein.

A composition disclosed herein comprises a surfactant metal complex in an amount sufficient to promote or facilitate the reflection of UV light. In aspects of this embodiment, a composition disclosed herein comprises a surfactant metal complex in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises a surfactant metal complex in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises a surfactant metal complex in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

A chelating agent is a compound that chelates or binds metallic ions, such as with a heterocyclic ring structure so that the ion is held by chemical bonds from each of the participating rings. Chelating agent includes, without limitation, ethylene diaminetetraacetic acid (EDTA), EDTA disodium, calcium disodium edetate, EDTA trisodium, EDTA tetrasodium and EDTA dipotassium.

A preservative, includes, without limitation, citric acid, tartaric acid, phosphoric acid, iminodiacetic acid, nitrilotriacetic acid, hydroxyethyleneaminodiacetic acid and ethylenediaminetetraacetic acid and salts thereof; para-hydroxybenzoates such as butyl paraben, methyl paraben and propyl paraben; imidazolines (e.g., imidiazolinylurea), triclosan, hydantoins (e.g., dimethyloldimethylhydantoin), isothiazolidinone compounds and mixtures thereof, KATHON® CG and KATHON® CGII, which contain methylchloroisothiazolinone and methylisothiazolinone (Rohm and Haas).

A thickening agent (or gallant) is used to adjust the texture and viscosity of a composition disclosed herein. A thickening agent includes, without limitation, CARBOPOL™ resins [e.g., 934, 971, 974, 980, 981] and PEMULEN™ [TR-1 and TR-2] [both CARBOPOL™ and PEMULEN™ are registered trademarks of BF Goodrich], Noveon® AA-1, ETD resins, and ULTREZ™ resins or carbomers.

In an embodiment of the present composition, additional ingredients can be present include, without limitation, a fragrance, a dye, an oil, a wax (such as a non-polar wax), a liquid hydrocarbon and/or an antimicrobial material. A non-polar wax, includes, without limitation, ester waxes, diester waxes, hydrocarbon waxes, silicone waxes and triglyceride waxes and mixtures thereof.

A composition disclosed herein can include any number of additional components. In aspects of this embodiment, a composition disclosed herein may comprise, e.g., at least one, at least two, at least three, at least four, at least five, at least six, at least seven, at least eight, at least nine or at least ten additional components. In other aspects of this embodiment, a composition disclosed herein may comprise, e.g., at most one, at most two, at most three, at most four, at most five, at most six, at most seven, at most eight, at most nine or at most ten additional components. In yet other aspects of this embodiment, a composition disclosed herein may comprise, e.g., about 1 to about 2, about 1 to about 3, about 1 to about 4, about 1 to about 5, about 1 to about 6, about 1 to about 7, about 1 to about 8, about 1 to about 9, about 1 to about 10, about 2 to about 3, about 2 to about 4, about 2 to about 5, about 2 to about 6, about 2 to about 7, about 2 to about 8, about 2 to about 9, about 2 to about 10, about 3 to about 4, about 3 to about 5, about 3 to about 6, about 3 to about 7, about 3 to about 8, about 3 to about 9, about 3 to about 10, about 4 to about 5, about 4 to about 6, about 4 to about 7, about 4 to about 8, about 4 to about 9, about 4 to about 10, about 5 to about 6, about 5 to about 7, about 5 to about 8, about 5 to about 9, about 5 to about 10, about 6 to about 7, about 6 to about 8, about 6 to about 9, about 6 to about 10, about 7 to about 8, about 7 to about 9, about 7 to about 10, about 8 to about 9, about 8 to about 10 or about 9 to about 10 additional components.

A composition disclosed herein comprises an additional component in an amount sufficient to promote or facilitate the function or activity of that additional component. The amount of additional component can range from 0.00% to 99.9% by total weight of the composition, or any integer or range in therebetween. In aspects of this embodiment, a composition disclosed herein comprises an additional component in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises an additional component in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises an additional component in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

A composition disclosed herein comprises silicon dioxide-based particles disclosed herein in an amount sufficient to provide an effective amount of the one or more agents disclosed herein and/or one or more additional components. In aspects of this embodiment, a composition disclosed herein comprises a silicon dioxide particles disclosed herein in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 40%, at least 45%, at least 50%, at least 55%, at least 60%, at least 65%, at least 70% or at least 75% of the total weight of the composition.

In other aspects of this embodiment, a composition disclosed herein comprises silicon dioxide-based particles disclosed herein in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 16%, at most 17%, at most 18%, at most 19%, at most 20%, at most 21%, at most 22%, at most 23%, at most 24%, at most 25%, at most 26%, at most 27%, at most 28%, at most 29%, at most 30%, at most 31%, at most 32%, at most 33%, at most 34%, at most 35%, at most 40%, at most 45%, at most 50%, at most 55%, at most 60%, at most 65%, at most 70% or at most 75% of the total weight of the composition.

In other aspects of this embodiment, a composition disclosed herein comprises silicon dioxide-based particles disclosed herein in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.1% to about 15%, about 0.1% to about 20%, about 0.1% to about 25%, about 0.1% to about 30%, about 0.1% to about 35%, about 0.1% to about 40%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 0.5% to about 15%, about 0.5% to about 20%, about 0.5% to about 25%, about 0.5% to about 30%, about 0.5% to about 35%, about 0.5% to about 40%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 1.0% to about 25%, about 1.0% to about 30%, about 1.0% to about 35%, about 1.0% to about 40%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 2.0% to about 25%, about 2.0% to about 30%, about 2.0% to about 35%, about 2.0% to about 40%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 3.0% to about 25%, about 3.0% to about 30%, about 3.0% to about 35%, about 3.0% to about 40%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 4.0% to about 25%, about 4.0% to about 30%, about 4.0% to about 35% or about 4.0% to about 40% of the total weight of the composition.

In other aspects of this embodiment, a composition disclosed herein comprises silicon dioxide-based particles disclosed herein in an amount of, e.g., about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 5.0% to about 13%, about 5.0% to about 14%, about 5.0% to about 15%, about 5.0% to about 16%, about 5.0% to about 17%, about 5.0% to about 18%, about 5.0% to about 19%, about 5.0% to about 20%, about 5.0% to about 25%, about 5.0% to about 30%, about 5.0% to about 35%, about 5.0% to about 40%, about 8.0% to about 9.0%, about 8.0% to about 10%, about 8.0% to about 11%, about 8.0% to about 12%, about 8.0% to about 13%, about 8.0% to about 14%, about 8.0% to about 15%, about 8.0% to about 16%, about 8.0% to about 17%, about 8.0% to about 18%, about 8.0% to about 19%, about 8.0% to about 20%, about 8.0% to about 25%, about 8.0% to about 30%, about 8.0% to about 35%, or about 8.0% to about 40% of the total weight of the composition.

In other aspects of this embodiment, a composition disclosed herein comprises silicon dioxide-based particles disclosed herein in an amount of, e.g., about 10% to about 15%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 65%, about 10% to about 70%, about 10% to about 75%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 15% to about 75%, about 20% to about 25%, about 20% to about 30%, about 20% to about 35%, about 20% to about 40%, about 20% to about 45%, about 20% to about 50%, about 20% to about 55%, about 20% to about 60%, about 20% to about 65%, about 20% to about 70%, about 20% to about 75%, about 25% to about 30%, about 25% to about 35%, about 25% to about 40%, about 25% to about 45%, about 25% to about 50%, about 25% to about 55%, about 25% to about 60%, about 25% to about 65%, about 25% to about 70%, about 25% to about 75%, about 30% to about 35%, about 30% to about 40%, about 30% to about 45%, about 30% to about 50%, about 30% to about 55%, about 30% to about 60%, about 30% to about 65%, about 30% to about 70%, about 30% to about 75%, about 35% to about 40%, about 35% to about 45%, about 35% to about 50%, about 35% to about 55%, about 35% to about 60%, about 35% to about 65%, about 35% to about 70%, about 35% to about 75%, about 40% to about 45%, about 40% to about 50%, about 40% to about 55%, about 40% to about 60%, about 40% to about 65%, about 40% to about 70%, about 40% to about 75%, about 45% to about 50%, about 45% to about 55%, about 45% to about 60%, about 45% to about 65%, about 45% to about 70%, about 45% to about 75%, about 50% to about 55%, about 50% to about 60%, about 50% to about 65%, about 50% to about 70%, about 50% to about 75%, about 55% to about 60%, about 55% to about 65%, about 55% to about 70%, about 55% to about 75%, about 60% to about 65%, about 60% to about 70%, about 60% to about 75%, about 65% to about 70%, about 65% to about 75%, or about 70% to about 75%, of the total weight of the composition.

A composition disclosed herein comprises diatomaceous earth-based particles in an amount sufficient to provide an effective amount of the one or more active agents and/or the one or more additional components disclosed herein. In aspects of this embodiment, a composition disclosed herein comprises diatomaceous earth-based particles in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34% or at least 35% of the total weight of the composition.

In other aspects of this embodiment, a composition disclosed herein comprises diatomaceous earth-based particles in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 16%, at most 17%, at most 18%, at most 19%, at most 20%, at most 21%, at most 22%, at most 23%, at most 24%, at most 25%, at most 26%, at most 27%, at most 28%, at most 29%, at most 30%, at most 31%, at most 32%, at most 33%, at most 34% or at most 35% of the total weight of the composition.

In other aspects of this embodiment, a composition disclosed herein comprises diatomaceous earth-based particles in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.1% to about 15%, about 0.1% to about 20%, about 0.1% to about 25%, about 0.1% to about 30%, about 0.1% to about 35%, about 0.1% to about 40%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 0.5% to about 15%, about 0.5% to about 20%, about 0.5% to about 25%, about 0.5% to about 30%, about 0.5% to about 35%, about 0.5% to about 40%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 1.0% to about 25%, about 1.0% to about 30%, about 1.0% to about 35%, about 1.0% to about 40%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 2.0% to about 25%, about 2.0% to about 30%, about 2.0% to about 35%, about 2.0% to about 40%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 3.0% to about 25%, about 3.0% to about 30%, about 3.0% to about 35%, about 3.0% to about 40%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 4.0% to about 25%, about 4.0% to about 30%, about 4.0% to about 35% or about 4.0% to about 40% of the total weight of the composition.

In other aspects of this embodiment, a composition disclosed herein comprises diatomaceous earth-based in an amount of, e.g., about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 5.0% to about 13%, about 5.0% to about 14%, about 5.0% to about 15%, about 5.0% to about 16%, about 5.0% to about 17%, about 5.0% to about 18%, about 5.0% to about 19%, about 5.0% to about 20%, about 5.0% to about 25%, about 5.0% to about 30%, about 5.0% to about 35%, about 5.0% to about 40%, about 8.0% to about 9.0%, about 8.0% to about 10%, about 8.0% to about 11%, about 8.0% to about 12%, about 8.0% to about 13%, about 8.0% to about 14%, about 8.0% to about 15%, about 8.0% to about 16%, about 8.0% to about 17%, about 8.0% to about 18%, about 8.0% to about 19%, about 8.0% to about 20%, about 8.0% to about 25%, about 8.0% to about 30%, about 8.0% to about 35%, about 8.0% to about 40%, about 10.0% to about 15%, about 10.0% to about 20%, about 10.0% to about 25%, about 10.0% to about 30%, about 10.0% to about 35%, about 10.0% to about 40%, about 15.0% to about 20%, about 15.0% to about 25%, about 15.0% to about 30%, about 15.0% to about 35%, about 15.0% to about 40%, about 20.0% to about 25%, about 20.0% to about 30%, about 20.0% to about 35%, about 20.0% to about 40%, about 25.0% to about 30%, about 25.0% to about 35%, about 25.0% to about 40%, about 30.0% to about 35%, about 30.0% to about 40% or about 35.0% to about 40% of the total weight of the composition.

A composition disclosed herein comprises sol gel capsules and/or flexible cellulose-derived capsules in an amount sufficient to provide an effective amount of the one or more active agents and/or one or more additional component disclosed herein. In aspects of this embodiment, a composition disclosed herein comprises sol gel capsules and/or flexible cellulose-derived capsules in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34% or at least 35% of the total weight of the composition.

In other aspects of this embodiment, a composition disclosed herein comprises sol gel capsules and/or flexible cellulose-derived capsules in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 16%, at most 17%, at most 18%, at most 19%, at most 20%, at most 21%, at most 22%, at most 23%, at most 24%, at most 25%, at most 26%, at most 27%, at most 28%, at most 29%, at most 30%, at most 31%, at most 32%, at most 33%, at most 34% or at most 35% of the total weight of the composition.

In other aspects of this embodiment, a composition disclosed herein comprises sol gel capsules and/or flexible cellulose-derived capsules in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.1% to about 15%, about 0.1% to about 20%, about 0.1% to about 25%, about 0.1% to about 30%, about 0.1% to about 35%, about 0.1% to about 40%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 0.5% to about 15%, about 0.5% to about 20%, about 0.5% to about 25%, about 0.5% to about 30%, about 0.5% to about 35%, about 0.5% to about 40%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 1.0% to about 25%, about 1.0% to about 30%, about 1.0% to about 35%, about 1.0% to about 40%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 2.0% to about 25%, about 2.0% to about 30%, about 2.0% to about 35%, about 2.0% to about 40%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 3.0% to about 25%, about 3.0% to about 30%, about 3.0% to about 35%, about 3.0% to about 40%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 4.0% to about 25%, about 4.0% to about 30%, about 4.0% to about 35% or about 4.0% to about 40% of the total weight of the composition.

In other aspects of this embodiment, a composition disclosed herein comprises sol gel capsules and/or flexible cellulose-derived capsules in an amount of, e.g., about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 5.0% to about 13%, about 5.0% to about 14%, about 5.0% to about 15%, about 5.0% to about 16%, about 5.0% to about 17%, about 5.0% to about 18%, about 5.0% to about 19%, about 5.0% to about 20%, about 5.0% to about 25%, about 5.0% to about 30%, about 5.0% to about 35%, about 5.0% to about 40%, about 8.0% to about 9.0%, about 8.0% to about 10%, about 8.0% to about 11%, about 8.0% to about 12%, about 8.0% to about 13%, about 8.0% to about 14%, about 8.0% to about 15%, about 8.0% to about 16%, about 8.0% to about 17%, about 8.0% to about 18%, about 8.0% to about 19%, about 8.0% to about 20%, about 8.0% to about 25%, about 8.0% to about 30%, about 8.0% to about 35%, about 8.0% to about 40%, about 10.0% to about 15%, about 10.0% to about 20%, about 10.0% to about 25%, about 10.0% to about 30%, about 10.0% to about 35%, about 10.0% to about 40%, about 15.0% to about 20%, about 15.0% to about 25%, about 15.0% to about 30%, about 15.0% to about 35%, about 15.0% to about 40%, about 20.0% to about 25%, about 20.0% to about 30%, about 20.0% to about 35%, about 20.0% to about 40%, about 25.0% to about 30%, about 25.0% to about 35%, about 25.0% to about 40%, about 30.0% to about 35%, about 30.0% to about 40% or about 35.0% to about 40% of the total weight of the composition.

A composition disclosed herein generally has a pH of about 4 to about 8. In aspects of this embodiment, a composition has a pH of, e.g., about 4 to about 5, about 4 to about 6, about 4 to about 7, about 4 to about 8, about 5 to about 6, about 5 to about 7, about 5 to about 8, about 6 to about 7, about 6 to about 8 or about 7 to about 8. In aspects of this embodiment, a composition has a pH of, e.g., about 6.4 to about 7.4, about 6.5 to about 7.5, about 6.6 to about 7.6, about 6.7 to about 7.7, about 6.6 to about 7.2, about 6.7 to about 7.3, about 6.8 to about 7.4, about 6.9 to about 7.5, about 7.0 to about 7.6, about 6.7 to about 7.1, about 6.8 to about 7.2, about 6.9 to about 7.3, about 7.0 to about 7.4, about 6.8 to about 7.0, about 6.9 to about 7.1 or about 7.0 to about 7.2.

A composition disclosed herein may comprise both loaded and unloaded silicon dioxide-based particles, like diatomaceous earth-based particles disclosed herein. The loaded silicon dioxide-based particles are ones that comprise one or more active agents as disclosed herein. Loaded silicon dioxide-based particles can be prepared using an oil in water emulsion technique using a high HLB emulsifier or using a water in oil emulsion technique using a low HLB emulsifier. The unloaded silicon dioxide-based particles are ones that do not contain any active agents or additional components as disclosed herein and can be considered "empty" or "unloaded." Unloaded silicon dioxide-based particles can be prepared by mixing the particles in a water-based formulation with minimal or no oil. Unloaded silicon dioxide-based particles are useful for their structural properties and/or absorbative properties.

In aspects of this embodiment, the ratio of loaded silicon dioxide-based particles to unloaded silicon dioxide-based particles used as an admixture in a composition disclosed herein can be from, e.g., about 1.0 part unloaded silicon dioxide-based particles to 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.5, 3.7, 4.0, 4.2, 4.5, 4.7, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 loaded silicon dioxide-based particles. Likewise, the ratio of unloaded silicon dioxide-based particles to loaded silicon dioxide-based particles to be utilized as an admixture in a composition disclosed herein can be from, e.g., about 1.0 part loaded silicon dioxide-based particles to 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.5, 3.7, 4.0, 4.2, 4.5, 4.7, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 unloaded silicon dioxide-based particles.

The ratio of the combined loaded and unloaded silicon dioxide-based particle admixture to a composition disclosed herein can be about 1.0 part admixture to 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.5, 3.7, 4.0, 4.2, 4.5, 4.7, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 parts composition.

A composition disclosed herein may comprise silicon dioxide-based particles, like diatomaceous earth-based particles disclosed herein, with or without a sol-gel capsule, with or without a flexible cellulose-derived capsule each comprising one or more active agents disclosed herein or any combination thereof.

In an embodiment, a composition disclosed herein comprises both one or more active agents and/or additional components disclosed herein encapsulated in silicon dioxide-based particles like diatomaceous earth-based particles. In another embodiment, a composition disclosed herein comprises one or more one or more active agents disclosed herein encapsulated in silicon dioxide-based particles like diatomaceous earth-based particles, and one or more additional components disclosed herein that are not encapsulated. In another embodiment, a composition disclosed herein comprises one or more active agents and/or additional components disclosed herein encapsulated in silicon dioxide-based particles like diatomaceous earth-based particles and one or more active agents and/or one or more additional components disclosed herein that are not encapsulated.

In another embodiment, a composition disclosed herein comprises one or more active agents and/or additional components disclosed herein encapsulated in silicon dioxide-based particles like diatomaceous earth-based particles and one or more active agents and/or additional components and disclosed herein encapsulated in sol-gel capsules. In another embodiment, a composition disclosed herein comprises one or more active agents disclosed herein encapsulated in silicon dioxide-based particles like diatomaceous earth-based particles and one or more active agents disclosed herein encapsulated in sol-gel capsules and one or more active agents and/or one or more additional components disclosed herein that are not encapsulated.

In another embodiment, a composition disclosed herein comprises one or more active agents and/or additional components disclosed herein encapsulated in silicon dioxide-based particles like diatomaceous earth-based particles and one or more active agents and/or additional components and disclosed herein encapsulated in flexible cellulose-derived capsules. In another embodiment, a composition disclosed herein comprises one or more active agents disclosed herein encapsulated in silicon dioxide-based particles like diatomaceous earth-based particles and one or more active agents disclosed herein encapsulated in flexible cellulose-derived capsules and one or more active agents and/or one or more additional components disclosed herein that are not encapsulated.

In another embodiment, a composition disclosed herein comprises one or more active agents and/or additional components disclosed herein encapsulated in silicon dioxide-based particles like diatomaceous earth-based particles and/or sol-gel capsules and/or flexible cellulose-derived capsules. In another embodiment, a composition disclosed herein comprises one or more active agents and/or additional components disclosed herein encapsulated in silicon dioxide-based particles like diatomaceous earth-based particles and/or sol-gel capsules and/or flexible cellulose-derived capsules and one or more active agents and one or more additional components disclosed herein that are not encapsulated.

A composition disclosed herein can be manufactured as a solid, a liquid, a colloidal, or an aerosol. In addition, a composition disclosed herein can be manufactured into, without limitation, a body wash, an after-shower body lotion, a shampoo, a conditioner, a soap, a gel, a hand sanitizer, a cream, a spray, a mousse, a lotion, an ointment, a powder, a stick, an injectable, an ingestable, a make-up product, a lip balm, a hair spray product, an arachnid/insect repellent, a cosmetic product, or a medicinal product. As such, the disclosed compositions may be easily and conveniently applied during normal hygienic activities, such as, e.g., washing, showering, bathing, after bathing or showering while the skin is still wet, or during routine moisturizing or other hygiene activities, resulting in the application of an effective level of one or more active agents to a skin surface, even after activities that would remove non-encapsulated active agents, such as, e.g., washing, rinsing, or swimming.

A composition disclosed herein may be applied topically to a skin surface or mucous membrane of an individual. A skin surface includes the skin of the arms, legs and torso and head, including the scalp and hair of an individual. A composition disclosed herein may be topically applied to an individual by hand or with an applicator. An applicator includes without limitation, with a sponge, a loofah, a toy, a cotton pad, a wash cloth, a specialized wash cloth, a towel, clothing, a spray bottle, an applicator bottle, a patch including a transdermal patch, a tape, including a bandaid, an inhaler, or any device or article, including a clothing article or applicator. A toy, includes, without limitation, a rubber squeeze toy, including, without limitation, a rubber duck, or a plastic squeeze toy. An applicator disclosed herein is preloaded or can be loaded with a composition disclosed herein. An applicator includes an applicator bottle with a roller ball, a push button, a nozzle, a turn knob or other means to apply the composition to an individual. Typically, an applicator disclosed herein provides a composition disclosed herein to an individual in metered, defined amounts. For example, metering may be accomplished by pushing down on a nozzle that is part of the applicator. An applicator may also be a squeezable bottle wherein a composition disclosed herein can be dispensed from the bottle as an individual squeezes the bottle. A composition disclosed herein may also be applied using a spray-on applicator, including, without limitation, a spray bottle.

A composition disclosed herein may be applied enterally or parenterally to an individual. Enteral administration includes, without limitation, oral administration and rectal administration. Parenteral administration includes, without limitation, by injection, by infusion, and by catheter. Enteral and parenteral routes of administration and the dosage forms appropriate for such routes are known to a person of ordinary skill, see, e.g., FDA Center for Drug Evaluation and Research Data Standards Manual: Route of Administration.

A composition disclosed herein can be, or combined with, a skin care product. Non-limiting examples of a skin care product include any conventional body wash, after-shower body lotion, shampoo, conditioner, soap, gel, hand sanitizer, cream, spray, mousse, lotion, ointment, powder, stick, injectable, ingestable, make-up product, lip balm, hair spray product, arachnid/insect repellent, a cosmetic product, or medicinal product. A body wash, shampoo, after-shower body lotion, conditioner, soap, gel, hand sanitizer, cream, spray, mousse, lotion, ointment, powder, stick, injectable, ingestable, make-up product, lip balm, hair spray product, arachnid/insect repellent, a cosmetic product, or medicinal product disclosed herein can be, without limitation, any body wash, after-shower body lotion, shampoo, conditioner, soap, gel, hand sanitizer, cream, spray, mousse, lotion, ointment, powder, stick, injectable, ingestable, make-up product, lip balm, hair spray product, arachnid/insect repellent, a cosmetic product, or medicinal product known or apparent to one of skill in the art. A skin care product may be applied by hand, washcloth, or any cleansing article such as a brush, loofah, pouf, sponge, or other to an individual.

A bodywash includes, without limitation, a lathering bodywash or a non-lathering bodywash. A bodywash includes, without limitation, an emulsion of water and detergent base with added fragrance and is a skin cleaning agent commonly used in a shower or bath. A bodywash may also contain one or more surfactants. Popular brands include, for example Fa, Palmolive, Axe, Lynx, Radox, Nivea, Johnson, Senses, Adidas, Umbro, Old Spice, Imperial Leather and Right Guard. A bodywash also includes, without limitation an all-in-one multifunctional, moisturizing cleanser that both provides SPF and imparts color to the skin after application, wherein the bodywash includes, without limitation, iron oxide pigments as well as red petrolatum, at least one, preferably two, anionic lathering surfactants, a non-ionic lathering surfactant, surface-treated zinc oxide pigments, an alkyl silicone and a volatile cyclic silicone.

A spray includes, without limitation, an aerosol spray that includes a propellant. A propellant includes, without limitation is a mixture of isobutane, butane and propane, including, without limitation A46, AP30 (11% propane, 29% isobutane, 60% n-butane); AP40 (22% propane, 24% isobutane, 54% n-butane); and AP70 (31% propane, 23% isobutane, 46% n-butane). A spray includes, without limitation, hair spray, body spray, for example, without limitation, those sold by AXE®, spray on insect protection and spray on deodorant.

A shampoo includes, without limitation, sodium lauryl sulfate and/or sodium laureth sulfate with a co-surfactant, including, without limitation, cocamidopropyl betaine in water to form a thick, viscous liquid. A shampoo may include salt, including, without limitation, sodium chloride, a preservative and a fragrance. In an embodiment, a shampoo is formulated to maximize the following qualities, without limitation, pleasing foam, easy rinsing, minimal skin or eye irritation, feels thick and/or creamy, pleasant fragrance, low toxicity, good biodegradability, slightly acidic and no or minimal damage to hair.

A lotion includes, without limitation, a low to low medium viscosity topical preparation intended for application to unbroken skin. A lotion, as one example, is an oil-in-water emulsion that includes, without limitation, cetearyl alcohol and an emulgent to prevent separation of these two phases. A lotion contains, without limitation, fragrances, glycerol, petroleum jelly, dyes, preservatives, proteins and stabilizing agents. A lotion includes, without limitation a skin medication such as an antibiotic, antiseptic, antifungal, corticosteroid, anti-acne agents or soothing, smoothing, moisturizing or protective agents, including, without limitation, calamine. A gel includes, without limitation, a solid, jelly-like material that can have properties ranging from soft and weak to hard and tough and include, without limitation, substantially dilute cross-linked system, which exhibit no flow when in a steady-state. In an embodiment a gel includes, without limitation, a hydrogel, an organogel or a xerogel.

A conditioner includes, without limitation, hair conditioner, which can include, without limitation, the following ingredients: moisturizers, reconstructors, acidifiers, detanglers, thermal protectors, glossers, oils, surfactants, lubricants, sequestrants, antistatic agents, and preservatives. A conditioner includes, without limitation, a pack conditioner, a leave-in conditioner, an ordinary conditioner that includes both pack and leave-in ones and hold conditioners.

A hand sanitizer includes, without limitation, isopropanol, ethanol, n-propanol or povidone-iodine. In a further embodiment, hand sanitizers can contain the following inactive ingredients, without limitation, a thickening agent, including without limitation, polyacrylic acid for alcohol gels, humectants, including without limitation, glycerin for liquid rubs, propylene glycol and essential oils derived from plants. A hand sanitizer is a non-alcohol hand sanitizer, which includes without limitation, a nitrogenous cationic surface-acting agent that includes, without limitation, benzalkonium chloride, triclosan or povidone-iodine.

A soap is a salt of a fatty acid. Soaps for cleansing are generally obtained by treating vegetable or animal oils and fats with a strongly alkaline solution. Soaps can be in a solid form, such as a bar or in a decorative shape. Soap can also be a liquid. Other components can be added to soap, without limitation, including oils, fragrances and conditioners. In a further embodiment, a soap contains a surfactant. In another embodiment, a soap does not contain a surfactant.

In an embodiment, a soap is a melt and pour soap. The process for a melt and pour soap differs from the cold process, hot process or rebatching process of making soap in that no soap is made (i.e. no actual saponification occurs) in the process; a melt and pour soap base acquired in commerce is melted in a direct heat melter or water jacket melting pot (large double boiler) and additional items such as fragrance, essential oils, moisturizing agents, colorants, or exfoliating agents are added. While still hot, the concoction can be poured into individual molds, tray molds, or blocks which upon cooling can be sliced. A melt and pour soap includes, without limitation, a clear glycerin soap or a white soap made from white coconut oil.

In an embodiment, a soap is Castile soap. Castile soap is a name used in English-speaking countries for olive oil-based soap made in a style similar to that originating in the Castile region of Spain. In an embodiment, Castile soap includes, without limitation, sodium hydroxide, potassium hydroxide and/or ash.

In one embodiment, a composition disclosed herein is used in combination as an admixture with a skin care product disclosed herein. A composition disclosed herein when combined as an admixture with a skin care product in an amount sufficient to allow the one or more active agents, cationic polymers, film formers, photostabilizing agents, surfactant metal complexes, and additional components to function properly. In aspects of this embodiment, a composition disclosed herein is combined with a skin care product in a ratio of, e.g., about 1.0 part composition to 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.5, 3.7, 4.0, 4.2, 4.5, 4.7, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 parts skin care product.

In other aspects of this embodiment, a composition disclosed herein is combined with a skin care product in a ratio range of, e.g., about 1.0 part composition to about 0.1 to about 1.0 part skin care product, about 1.0 part composition to about 0.1 to about 5.0 parts skin care product, about 1.0 part composition to about 0.1 to about 10 parts skin care product, about 1.0 part composition to about 0.1 to about 15 parts skin care product, about 1.0 part composition to about 0.1 to about 20 parts skin care product, about 1.0 part composition to about 0.5 to about 1.0 part skin care product, about 1.0 part composition to about 0.5 to about 5.0 parts skin care product, about 1.0 part composition to about 0.5 to about 10 parts skin care product, about 1.0 part composition to about 0.5 to about 15 parts skin care product, about 1.0 part composition to about 0.5 to about 20 parts skin care product, about 1.0 part composition to about 1.0 to about 5.0 parts skin care product, about 1.0 part composition to about 1.0 to about 10 parts skin care product, about 1.0 part composition to about 1.0 to about 15 parts skin care product, about 1.0 part composition to about 1.0 to about 20 parts skin care product, about 1.0 part composition to about 5.0 to about 25 parts skin care product, about 1.0 part composition to about 1.0 to about 30 parts skin care product, about 1.0 part composition to about 1.0 to about 35 parts skin care product, about 1.0 part composition to about 1.0 to about 40 parts skin care product, about 1.0 part composition to about 1.0 to about 45 parts skin care product, about 1.0 part composition to about 1.0 to about 50 parts skin care product, about 1.0 part composition to about 1.0 part composition to about 5.0 to about 10 parts skin care product, about 1.0 part composition to about 5.0 to about 15 parts skin care product, about 1.0 part composition to about 5.0 to about 20 parts skin care product, about 1.0 part composition to about 5.0 to about 25 parts skin care product, about 1.0 part composition to about 5.0 to about 30 parts skin care product, about 1.0 part composition to about 5.0 to about 35 parts skin care product, about 1.0 part composition to about 5.0 to about 40 parts skin care product, about 1.0 part composition to about 5.0 to about 45 parts skin care product or about 1.0 part composition to about 5.0 to about 50 parts skin care product.

In an embodiment, a composition disclosed herein is formulated as a skin care product. In aspects of this embodiment, a composition disclosed herein is formulated as a body wash, after-shower body lotion, shampoo, conditioner, soap, gel, hand sanitizer, cream, spray, mousse, lotion, ointment, powder, stick, injectable, ingestable, make-up product, lip balm, hair spray product, arachnid/insect repellent, a cosmetic product, or medicinal product as disclosed herein.

In one embodiment, a composition disclosed herein can be used to protect an individual from sun exposure or other sources of UV light. A composition is accordingly provided herein, that comprises silicon dioxide-based particles, such as diatomaceous earth-based particles comprising one or more active agent, including, without limitation, a sunscreen agent, a photostabilizing agent, a moisturizing agent, a silicone containing compound, a liquid hydrocarbon, a soothing agent, a fragrance, a skin nourishing agent, a sunless tanning agent, or other molecule useful in protecting, moisturizing or otherwise shielding an individual from harmful exposure to UV light. In further accordance with the teachings of the present disclosure and as disclosed below, silicon dioxide-based particles, such as diatomaceous earth-based particles can be loaded with sunscreen or multiple sunscreens containing photostabilzers or photoboosters; in combination or addition, diatomaceous earth can be loaded with oils of high refractive properties to thereby provide a sunscreen carrier for topical delivery. Silicon dioxide-based particles, such as diatomaceous earth-based particles can be combined with inorganic particles recognized to be UV filter types including zinc, titanium dioxide, aluminium, silicon dioxide, other forms of silica and the like.

In an aspect of this embodiment, a sunscreen composition comprises a combination of silicon dioxide-based particles, such as diatomaceous earth-based particles, that are loaded and unloaded. The loaded silicon dioxide-based particles include one or more active agents useful in protecting, moisturizing or otherwise shielding an individual from harmful exposure to UV light as disclosed herein. The unloaded silicon dioxide-based particles are used to shield an individual from harmful exposure to UV light as unloaded silicon dioxide-based particles, such as diatomaceous earth-based particles, have an SPF of about 4 to about 6, about 4 to about 7, about 4 to about 8, about 4 to about 9, about 4 to about 10, about 4 to about 11, about 4 to about 12, about 4 to about 13, about 4 to about 14, or about 4 to about 15.

The ratio of loaded to unloaded silicon dioxide-based particles comprising a composition disclosed herein can be about 1.0 part loaded to 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.5, 3.7, 4.0, 4.2, 4.5, 4.7, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or about 55, about 60, about 65, about 70, about 75 about 80, about 85, about 90, about 95 unloaded. The unloaded portion of silicon dioxide-based particles, such as diatomaceous earth-based particles, provide a final composition (having as a component the admixture of loaded and unloaded silicon dioxide-based particles, such as diatomaceous earth-based particles) that not only provides a method for carrying and deposition of one or more active agents useful to treat acne as disclosed herein, but also provides for a component, that is, the unloaded silicon dioxide-based particles, such as diatomaceous earth-based particles, that absorbs surface oils present onto surfaces upon which the composition is disposed such as on skin, scalp, hair, for example. The ratio of the combined loaded and unloaded silicon dioxide-based particle composition admixture, to treat acne, a to a skin care product can be about 1.0 part admixture to 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.5, 3.7, 4.0, 4.2, 4.5, 4.7, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 parts skin care product.

In one embodiment, a composition disclosed herein can be used to protect an individual from a pest, including an insect or an arachnid. A composition is accordingly provided herein, that comprises silicon dioxide-based particles, such as diatomaceous earth-based particles comprising one or more active agent, including, without limitation, an arachnid/insect repellent, a pest repellent, an anti-lice agent, a moisturizing agent, an analgesic agent, an aesthetic agent, an anti-allergenic agent, an anti-microbial agent, a medicinal agent, a soothing agent, a fragrance, a skin nourishing agent, or other molecule useful in protecting, moisturizing or otherwise shielding an individual from a pest.

In an aspect of this embodiment, a pest control composition comprises a combination of silicon dioxide-based particles, such as diatomaceous earth-based particles, that are loaded and unloaded. The loaded silicon dioxide-based particles include one or more active agents useful in protecting, moisturizing or otherwise shielding an individual from a pest. The unloaded silicon dioxide-based particles are used as an abrasive that scratches or other punctures the cuticle causing death of the pest due to desiccation.

In one embodiment, a composition disclosed herein can be used as a dermal filler. A dermal filler helps to diminish facial lines and restore volume and fullness to any body feature of any animal (human and otherwise). Dermal fillers are typically utilized on a person's face. As we age, our faces naturally lose subcutaneous fat, the result being that the underlying muscles are then working closer to the skin surface. Accordingly, smile lines and crow's feet become more apparent as well as other lines and depressions become more apparent. The facial skin also stretches a bit, adding to this loss of facial volume. Other factors that affect the facial skin include sun exposure, heredity and lifestyle. A dermal filer is accordingly provided herein, that comprises a silicon dioxide-based particle, such as a diatomaceous earth-based particle, and may contain an additional active agent or component. Exemplary active agents/additional components that may be used in a dermal filler composition disclosed herein include, without limitation, collagen, hyaluronic acid, an anti-cellulite agent, an anti-inflammatory agent, an antioxidant, an anti-pruritic agent, an anti-skin aging agent, an anti-skin wrinkling agent, a skin nourishing agent, a vitamin, Poly-L-lactic acid (PLLA), polymethylmethacrylate beads (PMMA microspheres; PMMA is a non-biodegradable, biocompatible, man-made polymer), calcium hydroxyl apatite or other molecule useful in protecting, or otherwise enhancing the health and appearance of a body feature. A demal filler comprising a silicon dioxide-based particle can provide structural support upon implantation/disposition into the body of a patient. Such administration can include injection or placement (by any means) to a facial area, a buttock area, a hand area, a foot area, an elbow area, for example. Depth placement of dermal fillers of the present disclosure are typically determined by the professional performing the procedure, since every person/area of placement and desired result is different, experience and technique of the injector is the most critical part to achieving the desired result. Exemplary depths to which dermal fillers of the instant disclosure can be utilized include, but are not limited to, mid to deep dermis, as known in the dermal filler art. Other areas of deposition can be nasolabial folds, marionette lines, a mentalis fold, and down-turned corners of the lips. Dermal fillers having silicon dioxide-based particles, such as diatomaceous earth-based particles, can be used for high lip line cases, asymmetrical lips around the mouth, lip augmentation, and completing cosmetic dentistry cases by creating a beautiful, young-looking frame around the teeth.

Accordingly, a dermal filler comprising a silicon dioxide-based particle, such as a diatomaceous earth-based particle, can be utilized to achieve various desired outcome, including, but not limited to, plump thin lips, enhance shallow contours, soften facial creases and wrinkles, improve the appearance of recessed scars, reconstruct contour deformities in the face and decrease or remove the shadow of the lower lids, among other effects.

A dermal filler composition comprising a silicon dioxide-based particle, such as a diatomaceous earth-based particle disclosed herein can comprise diatomaceous earth-based particles alone or can also be further comprised of one or more active agents disclosed herein in an amount sufficient to promote or facilitate the function or activity of that active agent. The amount of active agent disclosed herein can range from 0.00% to 99.9% by total weight of the dermal filler composition, or any integer or range in therebetween. In aspects of this embodiment, a composition disclosed herein comprises an active agent in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises an active agent in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

A dermal filler composition comprising a silicon dioxide-based particle, such as a diatomaceous earth-based particle disclosed herein can comprise diatomaceous earth-based particles alone or can also be further comprised of one or more active agents disclosed herein in an amount sufficient to promote or facilitate the function or activity of that active agent. In particular embodiments, the silicon dioxide-based particles, such as a diatomaceous earth-based particles, can be present in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the dermal filler composition. In particular embodiments, the silicon dioxide-based particles, such as a diatomaceous earth-based particle disclosed herein for use as/as a component of a dermal filler composition, can range from 0.00% to 99.9% by total weight of the composition, or any integer or range in therebetween.

In one embodiment, a composition disclosed herein can be used as a medical product to treat acne. In an aspect of this embodiment, a composition disclosed herein comprises a combination of silicon dioxide-based particles, such as diatomaceous earth-based particles, that are loaded and unloaded. The loaded silicon dioxide-based particles include one or more active agents useful to treat acne, such as, e.g., an anti-acne agent, including Tretinoin, benzol peroxide, and azaleic acid, an anti-microbial agent, an anti-inflammatory agent, a medicinal agent, or other molecule useful in preventing or treating an acne. The unloaded silicon dioxide-based particles are used to absorb oils and other fluids that are causal or symptomatic of an acne and as useful in drying a skin surface.

The ratio of loaded to unloaded silicon dioxide-based particles comprising a composition disclosed herein can be about 1.0 part loaded to 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.5, 3.7, 4.0, 4.2, 4.5, 4.7, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or about 55, about 60, about 65, about 70, about 75 about 80, about 85, about 90, about 95 unloaded. The unloaded portion of silicon dioxide-based particles, such as diatomaceous earth-based particles, provide a final composition (having as a component the admixture of loaded and unloaded silicon dioxide-based particles, such as diatomaceous earth-based particles) that not only provides a method for carrying and deposition of one or more active agents useful to treat acne as disclosed herein, but also provides for a component, that is, the unloaded silicon dioxide-based particles, such as diatomaceous earth-based particles, that absorbs surface oils present onto surfaces upon which the composition is disposed such as on skin, scalp, hair, for example. The ratio of the combined loaded and unloaded silicon dioxide-based particle composition admixture, to treat acne, a to a skin care product can be about 1.0 part admixture to 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.5, 3.7, 4.0, 4.2, 4.5, 4.7, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 parts skin care product.

In one embodiment, a composition disclosed herein can be used as a medical product to facilitate wound healing and scar repair. Accordingly, and in non-limiting examples, compositions are provide herein that comprise the silicon dioxide-based particles, such as a diatomaceous earth-based particles, that are loaded with one or more active agents that are advantageous for supplementing/facilitating the various phases involved in would healing and scar repair, including, without limitation, an analgesic agent, an aesthetic agent, an anti-inflammatory agent, an antioxidant, an anti-microbial agent, a medicinal agent, or other molecule useful in facilitating wound healing and scar repair.

These phases of wound healing and scar repair include inflammatory, proliferative and remodelling/maturation phases. The inflamatory phase has hemostatic and cellular components, the proliferative has reepithelialization, neo-vascularization and collagen deposition components. Active agents that affect/stimulate vasoconstriction/vasodilation, platelet degranulation (such as TGF-β and other factors), platelet plug formation (e.g. activate platelets and fibrin and exposed collagen) can be loaded into the silicon dioxide-based particles for deposition at wound sites. In a further example the silicon dioxide-based particles can leaded with TNF-α, TNF-β, IGF-1, and IL-1 to mimic macrophages' role in wound healing by secreting these factors at the would site from the silicon dioxide-based particles. Furthermore, utilization of silicon dioxide-based particles, such as diatomaceous earth-based particles, at a would site, can additionally provide an in-situ scaffolding site for cellular migration that takes place at a wound site during the proliferative phase of healing, supplementing granulation tissue formation. In particular embodiments, a composition comprising silicon dioxide-based particles, such as diatomaceous earth-based particles, for would healing may also comprise angiogenic agents that spur neovascularization of the wound site.

As one non-limiting example VEGF can be loaded onto the silicon dioxide-based particles, such as diatomaceous earth-based particles, of the instant disclosure, in an amount of about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition. Other active agents that would aid and promote wound healing may be loaded onto the silicon dioxide-based particles, such as diatomaceous earth-based particles, of the instant disclosure to provide for improved would healing.

In one embodiment, a composition disclosed herein can be used as a medical product to treat cancer. As an example, the silicon dioxide-based particles are loaded with one or more active agents, including, without limitation, an anti-angiogenic agent, a blood flow blocking agent, an anti-inflammatory agent, an antioxidant, an anti-microbial agent, a medicinal agent including a chemotherapeutic agent, or other molecule useful in treating cancer. A composition comprising silicon dioxide-based particles can be processed into an implant, such as a pellet, for example, for direct implantation into cancerous tissue, thereby providing a timed chemodrug release particle that will retard or eliminate angiogenesis that is required by the cancerous tissue. The compositions comprising silicon dioxide-based particles loaded with active agents, including antiangiogenic agent(s), can be incorporated in molding processes, for example, utilizing porous titaniumsilica (Ti/SiO$_2$) composite material to provide an implant containing an internal reservoir that can be loaded with and comprise the silicon dioxide-based particles loaded with active agents as herein disclosed. Various methods for providing an implantable drug delivery system can be utilized to incorporate the silicon-dioxide based particles, including diatomaceous earth-based particles, loaded with the active agents disclosed herein to provide a timed-release particle that can be implanted into any desired area on a body. Exemplary methods include compression, hot moulding, micro injection moulding and use of a plethora of polymers.

Compositions herein disclosed may be utilized for digestive support, bone and joint support, weigh loss, internal detoxification and other known uses of plain diatomaceous earth, the instant compositions having the advantage of being modified to carry active agents loaded into and/or onto the silicon dioxide-based particles like diatomaceous earth-based particles.

Besides the one or more active agents and one or more additional components disclosed herein, such skin care products may include additional ingredients necessary to formulate the skin care product. For example, a composition disclosed herein formulated as a skin care product disclosed herein may include one or more surfactants.

A surfactant may be cationic, anionic, non-ionic, zwitterionic, amphoteric, or any combination thereof. In a further embodiment, surfactants include, without limitation, alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, ethoxylated alkyl phosphates, acyl glutamates, acyl sarcosinates, alkyl sulfoacetates, acylated peptides, alkyl ether carboxylates, acyl lactylates, anionic fluorosurfactants, and combinations thereof. Combinations of anionic surfactants can be used effectively in the present invention. In a further embodiment, alkyl sulfates include, without limitation, sodium, ammonium, potassium, magnesium, or TEA salts of lauryl or myristyl sulfate or ammonium, sodium, magnesium, or TEA laureth-3 sulfate.

A composition disclosed herein comprises a surfactant in an amount sufficient to promote or facilitate the function or activity of that surfactant. In aspects of this embodiment, a composition disclosed herein comprises a surfactant in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises a surfactant in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises a surfactant in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

In an embodiment, a surfactant is an environmentally favourable surfactant including, without limitation, dodecyl glucosides.

In an embodiment, a surfactant is a lathering surfactant. A lathering surfactant has a log P of less than about 2.5 that produces foam when mixed with and agitated in water. An anionic lathering surfactant is a sulfate, wherein the sulfate is, without limitation, an alkyl sulfate or an alkyl ether sulfate. A sulfate includes, without limitation, sodium laureth sulfate and ammonium laureth sulfate. Sodium laureth sulfate has a molecular formula $CH_3(CH_2)_{10}CH_2(OCH_2CH_2)_{20}SO_3Na$ and conforms to the following structure:

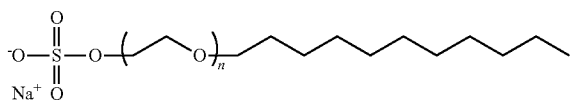

In an embodiment, a composition or a skin care product combined with a composition, includes, without limitation, sodium laureth sulfate at a concentration of from about 10% to about 15% or from about 7.5% to about 8.5%. In a further embodiment, ammonium laureth sulfate is used in combination with an alkyl glucoside, wherein the alkyl glucoside includes, without limitation, decyl glucoside. The combination of ammonium laureth sulfate and decyl glucoside is sold under the tradename Plantaren PS-100 by Cognis. In an embodiment, ammonium laureth sulfate in combination with decyl glucoside is present in a composition or body wash, after-shower body lotion, shampoo, conditioner, soap, gel, hand sanitizer, cream, spray, mousse, lotion, ointment, powder, stick, injectable, ingestable, make-up product, lip balm, hair spray product, arachnid/insect repellent, a cosmetic product, or medicinal product combined with a composition at a concentration of from about 5% to about 10%, or from about 7.5% to about 8.5%.

In a further embodiment, a lathering surfactant includes one, two, three or more anionic lathering surfactants, including, without limitation, sulfates, including, without limitation, sodium laureth sulfate and ammonium laureth sulfate. In an embodiment, sodium laureth sulfate and ammonium laureth sulfate are combined with decyl glucoside. In an additional embodiment, the two sulfates are present at a combined concentration of from about 15% to about 25%.

In an embodiment, a composition disclosed herein includes, without limitation, at least one cationic surfactant. In an embodiment, cationic surfactants include, without limitation, fatty amines, di-fatty quaternary amines, tri-fatty quaternary amines, imidazolinium quaternary amines, and combinations thereof. In a further embodiment, fatty amines include, without limitation, monoalkyl quaternary amines such as cetyltrimethylammonium bromide. In an embodiment, quaternary amine include, without limitation, dialklamidoethyl hydroxyethylmonium methosulfate, In an embodiment, a composition disclosed herein includes, without limitation, stearyldimethylbenzyl ammonium chloride; dodecyltrimethylammonium chloride; nonylbenzylethyldimethyl ammonium nitrate; tetradecylpyridinium bromide; laurylpyridinium chloride; cetylpyridinium chloride; laurylpyridinium chloride; laurylisoquinolium bromide; ditallow(Hydrogenated)dimethyl ammonium chloride; dilauryldimethyl ammonium chloride; and stearalkonium chloride. Additional cationic surfactants are disclosed in U.S. Pat. No. 4,303,543 see e.g. column 4, lines 58 and column 5, lines 1-42, incorporated herein by references. Also see CTFA Cosmetic Ingredient Dictionary, 4th Edition 1991, pages 509 514 for various long chain alkyl cationic surfactants; incorporated herein by reference.

In a further embodiment, anionic surfactants, include, without limitation, sulfated monoglycerides of the form $R^1CO—O—CH_2—C(OH)H—CH_2—O—SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine, monoethanolamine and sodium cocomonoglyceride sulfate. In a further embodiment, anionic surfactants include, without limitation, olefin sulfonates of the form $R^1SO_3M$, wherein $R^1$ is a mono-olefin having from about 12 to about 24 carbon atoms, and M is a water-soluble cation such as ammonium, sodium, potassium, magnesium, triethanolamine, diethanolamine and monoethanolamine. In an embodiment, a sulfonated olefin is sodium C14/C16 α-olefin sulfonate. In a further embodiment, anionic surfactants, include, without limitation, linear alkylbenzene sulfonates of the form $R^1—C_6H_4—SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine monoethanolamine and sodium dodecylbenzene sulfonate. In an additional embodiment, anionic surfactants include, without limitation, primary or secondary alkane sulfonates of the form $R^1SO_3M$, wherein $R^1$ is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. In a further embodiment, alkane sulfonates include, without limitation, alkali metal or ammonium $C_{13-17}$ paraffin sulfonates. In an additional embodiment, anionic surfactants include, without limitation, alkyl sulfosuccinates, which include disodium N-octadecylsulfosuccinamate, diammonium lauryl sulfosuccinate, disodium laureth sulfosuccinate, tetrasodium N-(1,2-dicarboxyethyl)-N-octadecylsulfosuccinate, diamyl ester of sodium sulfosuccinic acid, dihexyl ester of sodium sulfosuccinic acid and dioctyl esters of sodium sulfosuccinic acid; sodium dodecyl sulfate (or sodium lauryl sulfate), sodium laureth sulfate and ammonium lauryl sulfate.

Acyl taurate surfactants include, without limitation, taurine, N-alkyltaurines such as the one prepared by reacting dodecylamine with sodium isethionate as detailed in U.S. Pat. No. 2,658,072, and coconut fatty acid salts, such as, e.g., sodium methyl cocoyl taurate and sodium methyl oleoyl taurate.

In a further embodiment, anionic surfactants include, without limitation, acyl isethionates, including, without limitation, acyl isethionates include ammonium cocoyl isethionate, sodium cocoyl isethionate, sodium lauroyl isethionate, alkylglyceryl ether sulfonates of the form $R^1—OCH_2—C(OH)H—CH_2—SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine, sodium cocoglyceryl ether sulfonate, sulfonated fatty acids of the form $R^1$—$CH(SO_4)$—COOH and sulfonated methyl esters of the from $R^1$—$CH(SO_4)$—CO—O—$CH_3$, where $R^1$ is a saturated or unsaturated, branched or unbranched alkyl group from about 8 to about 24 carbon atoms (e.g., α-sulphonated coconut fatty acid and lauryl methyl ester); phosphates such as monoalkyl, dialkyl, and trialkylphosphate salts formed by the reaction of phosphorous pentoxide with monohydric branched or unbranched alcohols having from about 8 to about 24 carbon atoms (e.g., sodium mono or dilaurylphosphate, ethoxylated monoalkyl phosphates, etc.); acyl glutamates corresponding to the formula $R^1CO$—$N(COOH)$—$CH_2CH_2$—$CO_2M$ wherein $R^1$ is a saturated or unsaturated, branched or unbranched alkyl or alkenyl group of about 8 to about 24 carbon atoms, and M is a water-soluble cation (e.g., sodium lauroyl glutamate and sodium cocoyl glutamate); alkanoyl sarcosinates corresponding to the formula $R^1CON(CH_3)$—$CH_2CH_2$—$CO_2M$ wherein $R^1$ is a saturated or unsaturated, branched or unbranched alkyl or alkenyl group of about 10 to about 20 carbon atoms, and M is a water-soluble cation (e.g., sodium lauroyl sarcosinate, lauroyl sarcosine, sodium cocoyl sarcosinate, and ammonium lauroyl sarcosinate); alkyl ether carboxylates corresponding to the formula $R^1$—$(OCH_2CH_2)x$-$OCH_2$—$CO_2M$ wherein $R^1$ is a saturated or unsaturated, branched or unbranched alkyl or alkenyl group of about 8 to about 24 carbon atoms, x is 1 to 10, and M is a water-soluble cation (e.g., sodium laureth carboxylate); acyl lactylates corresponding to the formula $R^1CO$—[O—$CH(CH_3)$—CO]x-$CO_2M$ wherein $R^1$ is a saturated or unsaturated, branched or unbranched alkyl or alkenyl group of about 8 to about 24 carbon atoms, x is 3, and M is a water-soluble cation (e.g., sodium cocoyl lactylate); carboxylates, nonlimiting examples of which include sodium lauroyl carboxylate, sodium cocoyl carboxylate, and ammonium lauroyl carboxylate; anionic flourosurfactants; and natural soaps derived from the saponification of vegetable and/or animal fats & oils examples of which include sodium laurate, sodium myristate, palmitate, stearate and tallowate, cocoate. In a further embodiment, a soap is a semi-solid. In another embodiment, a soap includes a wax to form a solid soap bar.

In an embodiment a counter cation, M, is used on the anionic surfactant. In a further embodiment, a counter cation includes, without limitation, sodium, potassium, ammonium, monoethanolamine, diethanolamine, and triethanolamine.

In an embodiment, non-ionic surfactants include, without limitation, alkyl glucosides, alkyl polyglucosides, polyhydroxy fatty acid amides, alkoxylated fatty acid esters, sucrose esters, amine oxides, and mixtures thereof. Alkyl glucosides and alkyl polyglucosides are condensation products of long chain alcohols, including, without limitation, $C_{8-30}$ alcohols, with sugars or starches or sugar or starch polymers, including, without limitation, glycosides or polyglycosides and are represented by the formula $(S)_n$—O—R wherein S is a sugar moiety such as glucose, fructose, mannose, and galactose; n is an integer of from about 1 to about 1000, and R is a $C_{8-30}$ alkyl group. In an embodiment, long chain alcohols from which the alkyl group can be derived include, without limitation, decyl alcohol, cetyl alcohol, stearyl alcohol, lauryl alcohol, myristyl alcohol, oleyl alcohol, and more. In a further embodiment, these surfactants include, without limitation, those wherein S is a glucose moiety, R is a $C_{8-20}$ alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). In an additional embodiment, sucrose ester surfactants include, without limitation, sucrose cocoate and sucrose laurate.

In another embodiment, non-ionic surfactants include, without limitation, polyhydroxy fatty acid amide surfactants, more specific examples of which include glucosamides. In an embodiment a process for making compositions containing polyhydroxy fatty acid amides are disclosed, for example, in G.B. Pat. Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934. In an embodiment, non-ionic surfactants include, without limitation, amine oxides, including, without limitation, those corresponding to the general formula $R_2$, $R_3NO$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. In an embodiment, amine oxides include, without limitation, dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

The term "amphoteric surfactant," as used herein, is also intended to encompass zwitterionic surfactants, which are well known to formulators skilled in the art as a subset of amphoteric surfactants. Amphoteric lathering surfactants include, without limitation, derivatives of aliphatic secondary and tertiary amines, including, without limitation, those wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate. In an embodiment, amphoteric or zwitterionic surfactants include, without limitation, betaines, sultaines, hydroxysultaines, alkyliminoacetates, iminodialkanoates, aminoalkanoates, and mixtures thereof. In an embodiment, betaines include, without limitation, the higher alkyl betaines, such as coco dimethyl carboxymethyl betaine, lauryl dimethyl carboxymethyl betaine, lauryl dimethyl α-carboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)α-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)_3$ radical is attached to the nitrogen atom of the betaine), oleyl betaine (available as amphoteric Velvetex® OLB-50 from Henkel), and cocamidopropyl betaine (available as Velvetex® BK-35 and BA-35 from Henkel). In a further embodiment, sultaines and hydroxysultaines include, without limitation, materials such as cocamidopropyl hydroxysultaine (available as Miratame® CBS from Rhone-Poulenc).

In an embodiment, amphoteric surfactants include, without limitation, the following compounds: Cetyl dimethyl betaine (this material also has the CTFA designation cetyl betaine); Cocamidopropylbetaine; Cocamidopropyl hydroxy sultaine. Examples of other useful amphoteric surfactants are alkyliminoacetates, and iminodialkanoates and aminoalkanoates of the formulas $RN[(CH_2)-CO_2-M]_2$ and $RNH(CH_2)_mCO_2$ M wherein m is from 1 to 4, R is a $C_8$-$C_{22}$ alkyl or alkenyl, and M is H, alkali metal, alkaline earth metal ammonium, alkanolammonium or imidazolinium and ammonium derivatives. In a further embodiment, amphoteric surfactants include, without limitation, sodium 3-dodecyl-aminopropionate, sodium 3-dodecylaminopropane sulfonate. In a further embodiment, N-higher alkyl aspartic acids include, without limitation, those produced according to the teaching of U.S. Pat. No. 2,438,091; and the products sold under the trade name "Miranol" and described in U.S. Pat. No. 2,528,378. In a further embodiment, amphoterics include, without limitation, amphoteric phosphates, such as coamidopropyl PG-dimonium chloride phosphate (commercially available as Monaquat PTC, from Mona Corp.). In another embodiment, amphoacetates include, without limitation, disodium lauroamphodiacetate, sodium lauroamphoacetate, and mixtures thereof.

In an embodiment, a bodywash is, without limitation, SUAVE® Body Wash, which has the following ingredients: Water, Ammonium Lauryl Sulfate, Ammonium Laureth Sulfate, Cocamidopropyl Betaine, Fragrance, Glycerin, Hydrolyzed Milk Protein & Honey Extract, PEG-10 Sunflower Glycerides, Cocamide MEA, Guar Hydroxypropylrimonium Chloride, Acrylates Copolymer, PEG-5 Cocamide, *Helianthus Annuus* (Sunflower) Seed Oil or *Glycine Soja* (Soybean) Oil, Tetrasoidum EDTA, Propylene Glycol, Ammonium Chloride, Sodium Hydroxide, Methylchloroisothiazolinone, Methylisothiazolinone, Titanium Dioxide (CI 77891).

In an embodiment, soapless cleansers are used in addition to, or instead of, soaps/surfactants, including, without limitation OILATUM™ AD (registered trademark, Stiefel Laboratories) AQUANIL™ (registered trademark, Person & Covey, Inc.), CETAPHIL™ (trademark, Galderma Laboratories, Inc.) or SPECTRODERM™ (registered trademark, Draxis Pharmaceutical Inc.), or their equivalents, may be utilized as a soapless component in the present invention.

In an embodiment, the composition containing an active agent is a powder or other dry form. In a further embodiment, the composition containing an active agent is applied to an individual by applying the powder or other dry form to the individual. In a further embodiment, following application of the powder or other dry form, the composition containing an active agent is rubbed, massaged, caressed onto the individual. In an embodiment, the composition containing an active agent that is in the form of a powder or other dry form is stored in an applicator. In an embodiment, the applicator is the same as the applicator used for powder or other dry form products, including, without limitation, a baby powder bottle or other applicator that is conformed to the application of a powder or other dry form of a composition.

In an embodiment, the components comprising a composition are mixed in, without limitation, water or oil. In an embodiment, a composition or composition combined with a body wash, after-shower body lotion, shampoo, conditioner, soap, gel, hand sanitizer, cream, spray, mousse, lotion, ointment, powder, stick, injectable, ingestable, make-up product, lip balm, hair spray product, arachnid/insect repellent, a cosmetic product, or medicinal product includes, without limitation, one or more surfactants. The use of surfactants in bodywashes is well-known in the art. Any surfactant known in the art and appropriate for a body wash, after-shower body lotion, shampoo, conditioner, soap, gel, hand sanitizer, cream, spray, mousse, lotion, ointment, powder, stick, injectable, ingestable, make-up product, lip balm, hair spray product, arachnid/insect repellent, a cosmetic product, or medicinal product may be used. See, McCutcheon's Detergents & Emulsifiers, M.C. Publishing Co. (North American edition 1989); Schwartz, et al., Surface Active Agents, Their Chemistry and Technology, New York, Interscience Publishers, 1949, and U.S. Pat. Nos. 6,096,697; 4,741,855; 4,788,066; 5,104,646; 5,106,609; 2,658,072; 2,438,091; 2,528,378; 2,486,921; 2,486,922; 2,396,278; 2,979,465; 3,179,599; 5,322,643; 5,084,212; 3,332,880; 4,122,029; 4,265,878; 4,421,769; 3,929,678; 3,959,461; 4,387,090; 4,303,543; and 6,224,852; and in British Patent Nos. 848,224 and 791,415. Also see CTFA Cosmetic Ingredient Dictionary, 4th Edition 1991, pages 509 514 for various long chain alkyl cationic surfactants; and Richmond, James M., Cationic Surfactants, Marcel Dekker, Inc., New York and Basel, 1990.

In an embodiment, a composition disclosed herein comprises silicon dioxide-based particles like diatomaceous earth-based particles comprising one or more active agents disclosed herein. In aspects of this embodiment, a composition disclosed herein comprises silicon dioxide-based particles like diatomaceous earth-based particles disclosed herein comprising one or more active agents, one or more polyquaterniums, and one or more surfactants. In aspects of this embodiment, a composition disclosed herein comprises silicon dioxide-based particles like diatomaceous earth-based particles comprising one or more active agents, one or more polyquaterniums, one or more anionic surfactants, and one or more amphoteric surfactants. In aspects of this embodiment, a composition disclosed herein comprises silicon dioxide-based particles like diatomaceous earth-based particles comprising one or more active agents, one or more polyquaterniums, one or more sulfate surfactants, and one or more betaine surfactants. In aspects of this embodiment, a composition disclosed herein comprises silicon dioxide-based particles like diatomaceous earth-based particles comprising one or more active agents, one or more emollients and one or more thickening agents. In aspects of this embodiment, a composition disclosed herein comprises silicon dioxide-based particles like diatomaceous earth-based particles comprising one or more active agents, one or more film formers, and one or more emollients. In aspects of this embodiment, a composition disclosed herein comprises silicon dioxide-based particles like diatomaceous earth-based particles comprising one or more active agents, one or more polyquaterniums, one or more film formers, one or more emollients and one or more thickening agents. In aspects of this embodiment, a composition disclosed herein comprises silicon dioxide-based particles like diatomaceous earth-based particles comprising one or more active agents, one or more polyquaterniums, and one or more soap bases. In aspects of this embodiment, a composition disclosed herein comprises silicon dioxide-based particles like diatomaceous earth-based particles comprising one or more active agents, one or more polymers, one or more film formers and one or more fragrances. In other aspects of this embodiment, a composition is a body wash, a shampoo, an after-shower body lotion, a conditioner, a soap, a gel, a hand sanitizer, a cream, a spray, a mousse, a lotion, an ointment, a powder, a stick, an injectable, an ingestable, a make-up product, a lip balm, a hair spray product, an arachnid/insect repellent, a cosmetic product, or a medicinal product.

In aspects of this embodiment, a composition disclosed herein comprises about 2% to about 14%, about 4% to about 12%, about 5% to about 11%, about 7% to about 9%, or about 8%, by weight of the total composition of silicon dioxide-based particles like diatomaceous earth-based particles comprising one or more active agents. In other aspects of this embodiment, a composition disclosed herein comprises about 5% to about 17%, about 7% to about 15%, about 8% to about 14%, about 10% to about 12%, or about 11%, by weight of the total composition of silicon dioxide-based particles like diatomaceous earth-based particles comprising one or more active agents. In yet other aspects of this embodiment, a composition disclosed herein comprises 8% to about 20%, about 10% to about 18%, about 11% to about 17%, about 13% to about 15% or about 14% by weight of the total composition of silicon dioxide-based particles like diatomaceous earth-based particles comprising one or more active agents disclosed herein. In still other aspects of this embodiment, a composition disclosed herein comprises about 14% to about 26%, about 16% to about 24%, about 17% to about 23%, about 19% to about 21% or about 20% by weight of the total composition of silicon dioxide-based particles like diatomaceous earth-based particles comprising one or more active agents. In other aspects of this embodiment, a composition disclosed herein comprises about 1% to about 50%, about 2% to about 40%, about 3% to about 38%, about 4% to about 36%, about 5% to about 36%, about 6% to about 34%, about 8% to about 32%, about 10% to about 30%, about 12% to about 28%, about 14% to about 26%, about 16% to about 24%, or about 18% to about 22%, by weight of the total composition of silicon dioxide-based particles like diatomaceous earth-based particles comprising one or more active agents.

In other aspects of this embodiment, a composition disclosed herein comprises silicon dioxide-based particles like diatomaceous earth-based particles disclosed herein comprising about 1% to about 5% of a first active agent, about 95% to about 99% of a second active agent, about 6% to about 10% of a first active agent, about 90% to about 94% of a second active agent, about 11% to about 15% of a first active agent, about 85% to about 89% of a second active agent, about 16% to about 20% of a first active agent, about 80% to about 84% of a second active agent, about 21% to about 25% of a first active agent about 75% to about 79% of a second active agent, about 26% to about 30% of a first active agent, about 70% to about 74% of a second active agent, about 31% to about 35% of a first active agent, about 65% to about 69% of a second active agent, about 36% to about 40% of a first active agent, about 60% to about 64% of a second active agent, about 41% to about 45% of a first active agent, about 55% to about 59% of a second active agent, or about 46% to about 50% of a first active agent, about 50% to about 54% of a second active agent. In yet other aspects of this embodiment, a composition disclosed herein comprises silicon dioxide-based particles like diatomaceous earth-based particles disclosed herein comprising about 17% to about 30% of a first active agent, about 17% to about 30% of a second active agent, about 19% to about 28% of a first active agent, about 19% to about 28% of a second active agent, about 21% to about 26% of a first active agent, about 21% to about 26% of a second active agent, about 23% to about 24% of a first active agent, about 23% to about 24% of a second active agent, about 23.5% of a first active agent, about 23.5 of a second active agent. In still other aspects of this embodiment, a composition disclosed herein comprises silicon dioxide-based particles like diatomaceous earth-based particles disclosed herein comprising about 50% to about 80% of a first active agent, about 55% to about 75% of a first active agent and about 20% to about 50% of a second active agent, about 55% to about 75% of a first active agent and about 25% to about 45% of a second active agent, about 60% to about 70% of a first active agent and about 30% to about 40% of a second active agent, about 63% to about 68% of a first active agent and about 33% to about 37% of a second active agent, or about 65% of a first active agent and about 35% of a second active agent.

In another embodiment, a composition disclosed herein further comprises a polyquaternium. In aspects of this embodiment, a composition disclosed herein comprises about 0.1% to about 10%, about 0.2% to about 8%, about 0.3% to about 7%, about 0.4% to about 6%, about 0.5% to about 5%, about 0.7% to about 4% or about 2.5% of a polyquaternium. In aspects of this embodiment, a polyquaternium includes a polyquaternium-1, polyquaternium-2, polyquaternium-4 (CELQUAT L-200), polyquaternium-5, polyquaternium-6, polyquaternium-7, polyquaternium-10, polyquaternium-11, polyquaternium-15, polyquaternium-16, polyquaternium-22, polyquaternium-28, polyquaternium-32, polyquaternium-37, polyquaternium-39, polyquaternium-40, polyquaternium-41, polyquaternium-42, polyquaternium-44, polyquaternium-45, polyquaternium-46, polyquaternium-47 and polyquaternium-64.

In another embodiment, a composition disclosed herein further comprises a film former. In aspects of this embodiment, a composition disclosed herein comprises about 1% to about 6%, about 1.5% to about 4.5%, about 2% to about 4%, about 2.5% to about 3.5% or about 3% of a film former. In other aspects of this embodiment, a composition disclosed herein comprises an acrylate copolymer as a film former. In yet other aspects of this embodiment, a composition disclosed herein comprises DERMACRYL® AQF as a film former.

In another embodiment, a composition disclosed herein further comprise one or more surfactants. In aspects of this embodiment, a composition disclosed herein comprises about 0.1% to about 20%, about 0.25% to about 18%, about 0.5% to about 15%, about 0.5% to about 12%, about 0.75% to about 10%, about 1% to about 8%, of one or more surfactants. In aspects of this embodiment, additional surfactants include additional cationic surfactants, anionic surfactants, non-ionic surfactants, zwitterionic surfactants, amphoteric surfactants, or any combination thereof.

In an embodiment, application of a composition disclosed herein can occur during washing in a suitable or effective amount, with application over part or the whole body. A shampoo or conditioner, gel, soap, hand sanitizer, cream, may be applied to hair, though in an embodiment, the shampoo combination product may be rinsed over part or the whole body, with a composition adhering to the skin and hair. A selected amount of a combination product may be applied directly to the skin, for instance, without limitation, a lotion, spray or bodywash or may be used through intermediate application to a washcloth, pad, sponge, or other applicator. After lathering, dirt and sloughed-off skin may be washed away by rinsing with water leaving behind one or more of the active agents, and in an embodiment, without limitation, an active agent encapsulated in a diatomaceous earth derived capsule.

A composition disclosed herein is also useful in the treatment of a skin condition. A skin condition includes, without limitation, Seborrheic dermatitis, eczema, xerosis, infestation, dyschromia, keratosis pilaris, acne, anti-aging, sensitive skin, ephilidies, solar lentigines, photo sensitive disease, skin cancer, melisma, autoimmune disorder, alopecia, fungal, bacterial, and viral infections, protect colored or treated hair, bromhidrosis, malodor, dandruff, wound healing, arachnid/insect repellent, pet shampoo/skin care, lindane or similar conditions.

In an embodiment, a composition comprising silicon dioxide-based particles like diatomaceous earth-based particles are used in products used by the military, police or other governmental or non-governmental force. In an embodiment, a product used by the by the military, police or other governmental or non-governmental force includes, without limitation, sunscreen, paint, clothes, weapons, including, without limitation, weapons containing composite or other synthetic parts, and other by the military, police or other governmental or non-governmental force products. In an embodiment, a composition comprising silicon dioxide-based particles like diatomaceous earth-based particles used for by the military, police or other governmental or non-governmental force includes a reflective agent and/or an agent capable of preventing the detection of infrared radiation by an individual or equipment.

A composition disclosed herein can be applied once per day, applied two, three, four or more times per day, applied every other day or applied about 10, 8, 7, 6, 5, 4, 3, 2 or 1 time per week. In aspects of this embodiment, the present invention discloses that a composition can be applied to wet skin and/or hair or applied to dry skin and/or hair.

Aspects of the present specification can also be described as follows:

1. A composition comprising, consisting essentially of or consisting of one or more silicon dioxide-based particles comprising one or more active agents.
2. The composition of embodiment 1, wherein the one or more silicon dioxide-based particles are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 40%, at least 45%, at least 50%, at least 55%, at least 60%, at least 65%, at least 70% or at least 75% of the total weight of the composition; or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 16%, at most 17%, at most 18%, at most 19%, at most 20%, at most 21%, at most 22%, at most 23%, at most 24%, at most 25%, at most 26%, at most 27%, at most 28%, at most 29%, at most 30%, at most 31%, at most 32%, at most 33%, at most 34%, at most 35%, at most 40%, at most 45%, at most 50%, at most 55%, at most 60%, at most 65%, at most 70% or at most 75%; or about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 1.0% to about 25%, about 1.0% to about 30%, about 1.0% to about 35%, about 1.0% to about 40%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 2.0% to about 25%, about 2.0% to about 30%, about 2.0% to about 35%, about 2.0% to about 40%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 3.0% to about 25%, about 3.0% to about 30%, about 3.0% to about 35%, about 3.0% to about 40%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 4.0% to about 25%, about 4.0% to about 30%, about 4.0% to about 35%, about 4.0% to about 40%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 5.0% to about 13%, about 5.0% to about 14%, about 5.0% to about 15%, about 5.0% to about 16%, about 5.0% to about 17%, about 5.0% to about 18%, about 5.0% to about 19%, about 5.0% to about 20%, about 5.0% to about 25%, about 5.0% to about 30%, about 5.0% to about 35%, about 5.0% to about 40%, about 8.0% to about 9.0%, about 8.0% to about 10%, about 8.0% to about 11%, about 8.0% to about 12%, about 8.0% to about 13%, about 8.0% to about 14%, about 8.0% to about 15%, about 8.0% to about 16%, about 8.0% to about 17%, about 8.0% to about 18%, about 8.0% to about 19%, about 8.0% to about 20%, about 8.0% to about 25%, about 8.0% to about 30%, about 8.0% to about 35%, about 8.0% to about 40%, about 10% to about 15%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 65%, about 10% to about 70%, about 10% to about 75%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 15% to about 75%, about 20% to about 25%, about 20% to about 30%, about 20% to about 35%, about 20% to about 40%, about 20% to about 45%, about 20% to about 50%, about 20% to about 55%, about 20% to about 60%, about 20% to about 65%, about 20% to about 70%, about 20% to about 75%, about 25% to about 30%, about 25% to about 35%, about 25% to about 40%, about 25% to about 45%, about 25% to about 50%, about 25% to about 55%, about 25% to about 60%, about 25% to about 65%, about 25% to about 70%, about 25% to about 75%, about 30% to about 35%, about 30% to about 40%, about 30% to about 45%, about 30% to about 50%, about 30% to about 55%, about 30% to about 60%, about 30% to about 65%, about 30% to about 70%, about 30% to about 75%, about 35% to about 40%, about 35% to about 45%, about 35% to about 50%, about 35% to about 55%, about 35% to about 60%, about 35% to about 65%, about 35% to about 70%, about 35% to about 75%, about 40% to about 45%, about 40% to about 50%, about 40% to about 55%, about 40% to about 60%, about 40% to about 65%, about 40% to about 70%, about 40% to about 75%, about 45% to about 50%, about 45% to about 55%, about 45% to about 60%, about 45% to about 65%, about 45% to about 70%, about 45% to about 75%, about 50% to about 55%, about 50% to about 60%, about 50% to about 65%, about 50% to about 70%, about 50% to about 75%, about 55% to about 60%, about 55% to about 65%, about 55% to about 70%, about 55% to about 75%, about 60% to about 65%, about 60% to about 70%, about 60% to about 75%, about 65% to about 70%, about 65% to about 75%, or about 70% to about 75%, of the total weight of the composition
3. The composition of embodiment 1 or 2, wherein the one or more silicon dioxide-based particles are in an amount of about 1% to about 50%, about 2% to about 40%, about 3% to about 38%, about 4% to about 36%, about 5% to about 36%, about 6% to about 34%, about 8% to about 32%, about 10% to about 30%, about 12% to about 28%, about 14% to about 26%, about 16% to about 24%, or about 18% to about 22%, by weight of the total composition.
4. The composition of embodiment 1 or 2, wherein the one or more silicon dioxide-based particles are in an amount of about 2% to about 14%, about 4% to about 12%, about 5% to about 11%, about 7% to about 9%, or about 8%, by weight of the total composition; or about 5% to about 17%, about 7% to about 15%, about 8% to about 14%, about 10% to about 12%, or about 11%, by weight of the total composition; or about 8% to about 20%, about 10% to about 18%, about 11% to about 17%, about 13% to about 15% or about 14% by weight of the total composition; or about 14% to about 26%, about 16% to about 24%, about 17% to about 23%, about 19% to about 21% or about 20% by weight of the total composition.
5. The composition of embodiment 1 or 2, wherein the one or more silicon dioxide-based particles are in an amount of about 0.1% to about 20%, about 0.1% to about 15%, about 0.5% to about 15%, about 0.75% to about 12%, about 0.75% to about 10%, about 1% to about 10%, about 1% to about 8%, about 2% to about 7%, about 5% to about 7%, about 3% to about 5%, about 6% or about 4% by weight of the total composition
6. The composition of any one of embodiments 1-5, wherein the one or more silicon dioxide-based particles comprising, consisting essentially of or consisting of one or more diatomaceous earth-based particles.
7. The composition of any one of embodiments 1-6 further comprises, consists essentially of or consists of one or more sol-gel capsules comprising one or more active agents, one or more flexible cellulose derived capsules comprising one or more active agents, or any combination of thereof.
8. The composition of any one of embodiments 1-7, wherein the composition is a body wash, a shampoo, an after-shower body lotion, a conditioner, a soap, a gel, a hand sanitizer, a cream, a spray, a mousse, a lotion, an ointment, a powder, a stick, an injectable, an ingestable, a make-up product, a lip balm, a hair spray product, an arachnid/insect repellent, a cosmetic product, or a medicinal product.
9. The composition of any one of embodiments 1-8, wherein the one or more silicon dioxide-based particles comprising, consisting essentially of or consisting of first silicon dioxide-based particles comprising one or more active agent and second silicon dioxide-based particles comprising one or more active agents.
10. The composition of any one of embodiments 1-9, wherein the one or more silicon dioxide-based particles comprising, consisting essentially of or consisting of first silicon dioxide-based particles comprising one or more active agents, second silicon dioxide-based particles comprising one or more active agents, and third silicon dioxide-based particles comprising one or more active agents.
11 The composition of any one of embodiments 1-10, wherein the one or more active agents includes a sunscreen agent, a photostabilizing agent, an analgesic agent, an aesthetic agent, an anti-acne agent, an anti-allergenic agent, an anti-angiogenic agent, a blood flow blocking agent, an anti-cellulite agent, an anti-inflammatory agent, an antioxidant, an anti-pruritic agent, an anti-skin aging agent, an anti-skin wrinkling agent, an anti-microbial agent, an anti-viral agent, a jellyfish repellent agent, a chelating agent, a deodorant, a dye, an essential oil, a hair growth promoter, a hair growth inhibitor, a hair bleaching agent, an anti-lice agent, an arachnid/insect repellent, a lipid, a medicinal agent, a moisturizing agent, a preservative, a silicone containing compound, a liquid hydrocarbon, a fragrance, a camouflage agent, a colorant, soothing agent, skin whitening agent, a skin nourishing agent, a structuring agent, a sunscreen agent, a sunless tanning agent, a thickening agent, or a vitamin.
12. The composition of any one of embodiments 1-11, wherein the one or more silicon dioxide-based particles comprise, consist essentially of or consist of a first silicon dioxide-based particle comprising one or more sunscreen agents.
13. The composition of any one of embodiments 1-11, wherein the one or more silicon dioxide-based particle comprises, consists essentially of or consists o first silicon dioxide-based particles comprising a first sunscreen agent and second silicon dioxide-based particles comprising a second sunscreen agent.
14. The composition of any one of embodiments 11-13, wherein the sunscreen agent includes a para-amino benzoate or derivative or salt thereof, a salicylate or derivative or salt thereof, a cinnamate or derivative or salt thereof, a benzophenone or derivative or salt thereof, an anthralinate or derivative or salt thereof, dibenzoylmethane or derivative or salt thereof, a camphor or derivative or salt thereof, a naphtholsulfonate or derivative or salt thereof, a coumarin or derivative or salt thereof, a diazole or derivative or salt thereof, a biphenyldisulfonate or derivative or salt thereof, a hydrocarbon or derivative or salt thereof, a quinolone or derivative or salt thereof, a quinine salt, a miscellaneous organic sunscreen active agent or any combination thereof.

15. The composition of any one of embodiments 11-14, wherein the sunscreen agent comprises, consists essentially of or consists of one or more broad-spectrum UVA/UVB sunscreen active agents, one or more UVA sunscreen active agents, one or more UVB sunscreen active agents, or any combination thereof.

16. The composition of any one of embodiments 11-15, wherein the sunscreen agent comprises, consists essentially of or consists of a broad-spectrum UVA/UVB sunscreen active agent and a UVA sunscreen active agent or comprise a broad-spectrum UVA/UVB sunscreen active agent, a UVA sunscreen active agent and a UVB sunscreen active agent or comprise a UVA sunscreen active agent and two different UVB sunscreen active agents.

17. The composition of any one of embodiments 11-16, comprising, consisting essentially of or consisting of a first silicon dioxide-based particle comprising, consisting essentially of or consisting of one or more sunscreen active agents and one or more photostabilizing agents and a second silicon dioxide-based particle comprising, consisting essentially of or consisting of one or more sunscreen active agents and one or more photostabilizing agents.

18. The composition of any one of embodiments 11-17, comprising, consisting essentially of or consisting of a first silicon dioxide-based particle comprising, consisting essentially of or consisting of one or more broad-spectrum UVA/UVB sunscreen active agents, one or more UVA sunscreen active agents, one or more UVB sunscreen active agents, or any combination thereof.

19. The composition of embodiment 18, wherein the first silicon dioxide-based particles comprise, consist essentially of or consist of a broad-spectrum UVA/UVB sunscreen active agent and a UVA sunscreen active agent or comprises a broad-spectrum UVA/UVB sunscreen active agent, a UVA sunscreen active agent and a UVB sunscreen active agent or comprises a UVA sunscreen active agent and two different UVB sunscreen active agents.

20. The composition of any one of embodiments 11-19, comprising, consisting essentially of or consisting of a second silicon dioxide-based particle comprising, consisting essentially of or consisting of one or more broad-spectrum UVA/UVB sunscreen active agents, one or more UVA sunscreen active agents, one or more UVB sunscreen active agents, or any combination thereof.

21. The composition of embodiment 20, wherein the second silicon dioxide-based particles comprise, consist essentially of or consist of a broad-spectrum UVA/UVB sunscreen active agent and a UVA sunscreen active agent or comprises a broad-spectrum UVA/UVB sunscreen active agent, a UVA sunscreen active agent and a UVB sunscreen active agent or comprises a UVA sunscreen active agent and two different UVB sunscreen active agents.

22. The composition of any one of embodiments 1-21, wherein the one or more silicon dioxide-based particle includes about 1% to about 14% by weight of the total composition of a silicon dioxide-based particles comprising, consisting essentially of or consisting of a UVB sunscreen active agent, about 2% to about 14% by weight of the total composition of a silicon dioxide-based particle comprising, consisting essentially of or consisting of a UVB sunscreen active agent, about 4% to about 12% by weight of the total composition of a silicon dioxide-based particle comprising, consisting essentially of or consisting of a UVB sunscreen active agent, about 5% to about 11% by weight of the total composition of a silicon dioxide-based particle comprising, consisting essentially of or consisting of a UVB sunscreen active agent, about 7% to about 9% by weight of the total composition of a silicon dioxide-based particle comprising, consisting essentially of or consisting of a UVB sunscreen active agent, or about 8% by weight of the total composition of a silicon dioxide-based particle comprising, consisting essentially of or consisting of a UVB sunscreen active agent.

23. The composition of any one of embodiments 1-21, wherein the one or more silicon dioxide-based particles includes about 1% to about 12% by weight of the total composition of a silicon dioxide-based particle comprising, consisting essentially of or consisting of a UVB sunscreen active agent, about 2% to about 10% by weight of the total composition of a silicon dioxide-based particle comprising, consisting essentially of or consisting of a UVB sunscreen active agent, about 3% to about 9% by weight of the total composition of a silicon dioxide-based particle comprising, consisting essentially of or consisting of a UVB sunscreen active agent, about 5% to about 7% by weight of the total composition of a silicon dioxide-based particle comprising, consisting essentially of or consisting of a UVB sunscreen active agent or about 6% by weight of the total composition of a silicon dioxide-based particle comprising, consisting essentially of or consisting of a UVB sunscreen active agent.

24. The composition of any one of embodiments 1-21, wherein the one or more silicon dioxide-based particles includes about 9% to about 21% by weight of the total composition of a silicon dioxide-based particle comprising, consisting essentially of or consisting of a first UVB sunscreen active agent, a UVA sunscreen active agent and a second UVB sunscreen active agent, about 11% to about 19% by weight of the total composition of a silicon dioxide-based particle comprising, consisting essentially of or consisting of a first UVB sunscreen active agent, a UVA sunscreen active agent and a second UVB sunscreen active agent, about 12% to about 18% by weight of the total composition of a silicon dioxide-based particle comprising, consisting essentially of or consisting of a first UVB sunscreen active agent, a UVA sunscreen active agent and a second UVB sunscreen active agent, about 14% to about 16% by weight of the total composition of a silicon dioxide-based particle comprising, consisting essentially of or consisting of a first UVB sunscreen active agent, a UVA sunscreen active agent and a second UVB sunscreen active agent or about 15% by weight of the total composition of a silicon dioxide-based particle comprising, consisting essentially of or consisting of a first UVB sunscreen active agent, a UVA sunscreen active agent and a second UVB sunscreen active agent.

25. The composition of any one of embodiments 1-21, wherein the one or more silicon dioxide-based particles includes about 9% to about 21% by weight of the total composition of a silicon dioxide-based particle comprising, consisting essentially of or consisting of a broad-spectrum UVA/UVB sunscreen active agent, a UVA sunscreen active agent and a UVB sunscreen active agent, about 11% to about 19% by weight of the total composition of a silicon dioxide-based particle comprising, consisting essentially of or consisting of a broad-spectrum UVA/UVB sunscreen active agent, a UVA sunscreen active agent and a UVB sunscreen active agent, about 12% to about 18% by weight of the total composition of a silicon dioxide-based particle comprising, consisting essentially of or consisting of a broad-spectrum UVA/UVB sunscreen active agent, a UVA sunscreen active agent and a UVB sunscreen active agent, about 14% to about 16% by weight of the total composition of a silicon dioxide-based particle comprising, consisting essentially of or consisting of a broad-spectrum UVA/UVB sunscreen active agent, a UVA sunscreen active agent and a UVB sunscreen active agent, about 15% by weight of the total composition of a silicon dioxide-based particle comprising, consisting essentially of or consisting of a broad-spectrum UVA/UVB sunscreen active agent or a UVA sunscreen active agent and a UVB sunscreen active agent.

26. The composition of any one of embodiments 1-21, wherein the one or more silicon dioxide-based particles includes about 5% to about 17% by weight of the total composition of a silicon dioxide-based particle comprising, consisting essentially of or consisting of a broad-spectrum UVA/UVB sunscreen active agent and a UVA sunscreen active agent, about 7% to about 15% by weight of the total composition of a silicon dioxide-based particle comprising, consisting essentially of or consisting of a broad-spectrum UVA/UVB sunscreen active agent and a UVA sunscreen active agent, about 8% to about 14% by weight of the total composition of a silicon dioxide-based particle comprising, consisting essentially of or consisting of a broad-spectrum UVA/UVB sunscreen active agent and a UVA sunscreen active agent, about 10% to about 12% by weight of the total composition of a silicon dioxide-based particle comprising, consisting essentially of or consisting of a broad-spectrum UVA/UVB sunscreen active agent and a UVA sunscreen active agent or about 11% by weight of the total composition of a silicon dioxide-based particle comprising, consisting essentially of or consisting of a broad-spectrum UVA/UVB sunscreen active agent and a UVA sunscreen active agent, 27. The composition of any one of embodiments 1-21, wherein the one or more silicon dioxide-based particles includes about 2% to about 14% by weight of the total composition of a silicon dioxide-based particle comprising, consisting essentially of or consisting of a broad-spectrum UVA/UVB sunscreen active agent and a UVA sunscreen active agent, about 4% to about 12% by weight of the total composition of a silicon dioxide-based particle comprising, consisting essentially of or consisting of a broad-spectrum UVA/UVB sunscreen active agent and a UVA sunscreen active agent, about 5% to about 11% by weight of the total composition of a silicon dioxide-based particle comprising, consisting essentially of or consisting of a broad-spectrum UVA/UVB sunscreen active agent and a UVA sunscreen active agent, about 7% to about 9% by weight of the total composition of a silicon dioxide-based particle comprising, consisting essentially of or consisting of a broad-spectrum UVA/UVB sunscreen active agent and a UVA sunscreen active agent or about 8% by weight of the total composition of a silicon dioxide-based particle comprising, consisting essentially of or consisting of a broad-spectrum UVA/UVB sunscreen active agent and a UVA sunscreen active agent.

28. The composition of any one of embodiments 1-21, wherein the one or more silicon dioxide-based particles includes about 1% to about 12% by weight of the total composition of a silicon dioxide-based particle comprising, consisting essentially of or consisting of a broad-spectrum UVA/UVB sunscreen active agent and a UVA sunscreen active agent, about 2% to about 10% by weight of the total composition of a silicon dioxide-based particle comprising, consisting essentially of or consisting of a broad-spectrum UVA/UVB sunscreen active agent and a UVA sunscreen active agent, about 3% to about 9% by weight of the total composition of a silicon dioxide-based particle comprising, consisting essentially of or consisting of a broad-spectrum UVA/UVB sunscreen active agent and a UVA sunscreen active agent, about 5% to about 7% by weight of the total composition of a silicon dioxide-based particle comprising, consisting essentially of or consisting of a broad-spectrum UVA/UVB sunscreen active agent and a UVA sunscreen active agent or about 6% by weight of the total composition of a silicon dioxide-based particle comprising, consisting essentially of or consisting of a broad spectrum UVA/UVB sunscreen active agent and a UVA sunscreen active agent 29. The composition of any one of embodiments 25-28, wherein the broad-spectrum UVA/UVB sunscreen active agent is present in an amount of about 45% to about 57%, about 47% to about 55%, about 48% to about 54%, about 50% to about 52% or about 51%.

30. The composition of any one of embodiments 25-28, wherein the broad-spectrum UVA/UVB sunscreen active agent is present in an amount of about 50% to about 80%, about 55% to about 75%, about 60% to about 70%, about 63% to about 68% or about 65%.

31. The composition of any one of embodiments 24-30, wherein the UVA sunscreen active agent is present in an amount of about 7% to about 19%, about 9% to about 17%, about 10% to about 16%, about 12% to about 14% or about 13%.

32. The composition of any one of embodiments 24-30, wherein the UVA sunscreen active agent is present in an amount of about 20% to about 50%, about 25% to about 45%, about 30% to about 40%, about 33% to about 37% or about 35%.

33. The composition of any one of embodiments 22-32, wherein the UVB sunscreen active agent is present in an amount of about 18% to about 30%, about 20% to about 28%, about 21% to about 27%, about 23% to about 25% or about 24%.

34. The composition of any one of embodiments 15, 16, 18-21 or 25-30, wherein the broad-spectrum UVA/UVB sunscreen active agent includes bemotrizinol (Tinosorb S), benzophenones 1-12, dioxybenzone, drometrizole trisiloxane (Mexoryl XL), Iscotrizinol (Uvasorb HEB), octocrylene, oxybenzone (Eusolex 4360), sulisobenzone, bisoctrizole (Tinosorb M), titanium dioxide, or zinc oxide.

35. The composition of any one of embodiments 15, 16, 18-21, 24-28, 31 or 32, wherein the UVA sunscreen active agent includes avobenzone (butyl methoxydibenzoylmethane or Parsol 1789), bisdisulizole disodium (Neo Heliopan AP), diethylamino hydroxybenzoyl hexyl benzoate (Uvinul A Plus), ecamsule (Mexoryl SX) or menthyl anthranilate, 36. The composition of any one of embodiments 15, 16, 18-25 or 33, wherein the UVB sunscreen active agent includes amiloxate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), Padimate 0 (Escalol 507), phenylbenzimidazole sulfonic acid (Ensulizole), polysilicone-15 (Parsol SLX) or trolamine salicylate.

37. The composition of any one of embodiments 11-36, wherein the one or more photostabilizing agents are present in an amount of about 0.25% to about 5%, about 0.5% to about 3.5%, about 1% to about 3%, about 1.5% to about 2.5% or about 2%.

38. The composition of any one of embodiments 11-36, wherein the one or more photostabilizing agents are present in an amount of about 1% to about 12%, about 2% to about 10%, about 3% to about 9%, about 5% to about 7% or about 6%.

39. The composition of any one of embodiments 11-36, wherein the one or more photostabilizing agents are present in an amount of about 0.1% to about 8%, about 0.25% to about 6%, about 0.5% to about 4%, about 1% to about 3% or about 2%.

40. The composition of any one of embodiments 11-36, wherein the one or more photostabilizing agents are present in an amount of about 0.1% to about 8%, about 0.25% to about 6%, about 0.5% to about 4%, about 1% to about 3% or about 2%.

41. The composition of any one of embodiments 11-36, wherein a first photostabilizing agent of the one or more photostabilizing agents is present in an amount of about 0.25% to about 5%, about 0.5% to about 3.5%, about 1% to about 3%, about 1.5% to about 2.5% or about 2%.

42. The composition of any one of embodiments 11-36 or 41, wherein a second photostabilizing agent of the one or more photostabilizing agents is present in an amount of about 0.25% to about 5%, about 0.5% to about 3.5%, about 1% to about 3%, about 1.5% to about 2.5% or about 2%.

43. The composition of any one of embodiments 11-36, 41 or 42, wherein a third photostabilizing agent of the one or more photostabilizing agents is present in an amount of about 0.25% to about 5%, about 0.5% to about 3.5%, about 1% to about 3%, about 1.5% to about 2.5% or about 2%.

44. The composition of any one of embodiments 1-43, further comprising, consisting essentially of or consisting of one or more sunscreen agents not encapsulated and/or one or more photostabilizing agents not encapsulated.

45. The composition of any one of embodiments 1-11, wherein the one or more silicon dioxide-based particles comprise, consist essentially of or consist of first silicon dioxide-based particles comprising one or more arachnid/insect repellents.

46. The composition of any one of embodiments 1-11, wherein the one or more silicon dioxide-based particles comprise, consist essentially of or consist of first silicon dioxide-based particles comprising one or more arachnid/insect repellents and second silicon dioxide-based particles comprising one or more arachnid/insect repellents.

47. The composition of any one of embodiments 1-11, wherein the one or more silicon dioxide-based particles comprise, consist essentially of or consist of first silicon dioxide-based particles comprising a first arachnid/insect repellent and second silicon dioxide-based particles comprising a second arachnid/insect repellent.

48. The composition of any one of embodiments 46 or 47, wherein the first arachnid/insect repellent is in an amount of about 1% to about 5% and the second arachnid/insect repellent is in an amount of about 95% to about 99%, or wherein the first arachnid/insect repellent is in an amount of about 6% to about 10% and the second arachnid/insect repellent is in an amount of about 90% to about 94%, or wherein the first arachnid/insect repellent is in an amount of about 11% to about 15% and the second arachnid/insect repellent is in an amount of about 85% to about 89%, or wherein the first arachnid/insect repellent is in an amount of about 16% to about 20% and the second arachnid/insect repellent is in an amount of about 80% to about 84%, or wherein the first arachnid/insect repellent is in an amount of about 21% to about 25% and the second arachnid/insect repellent is in an amount of about 75% to about 79%, or wherein the first arachnid/insect repellent is in an amount of about 26% to about 30% and the second arachnid/insect repellent is in an amount of about 70% to about 74%, or wherein the first arachnid/insect repellent is in an amount of about 31% to about 35% and the second arachnid/insect repellent is in an amount of about 65% to about 69%, or wherein the first arachnid/insect repellent is in an amount of about 36% to about 40% and the second arachnid/insect repellent is in an amount of about 60% to about 64%, or wherein the first arachnid/insect repellent is in an amount of about 41% to about 45% and the second arachnid/insect repellent is in an amount of about 55% to about 59%, or wherein the first arachnid/insect repellent is in an amount of about 46% to about 50% and the second arachnid/insect repellent is in an amount of about 50% to about 54%.

49. The composition of any one of embodiments 11 or 45-48, wherein the arachnid/insect repellent include one or more synthetic chemical compounds or one or more naturally-occurring compounds.

50. The composition of embodiment 49, wherein the one or more synthetic chemical compounds include N,N-Diethyl-m-toluamide (DEET), dimethyl phthalate, ethyl hexanediol, indalone, di-n-propylisocinchoronate, bicycloheptene, dicarboximide, dimethyl carbate, dimethyl phthalate, metofluthrin, indalone, permethrin, icaridin, nepetalactone, tetrahydrofuraldehyde ethyl butylacetylaminopropionate (IR-3535), p-menthane-3,8-diol (PMD), tricyclodecenyl allyl ether, ethylhexanediol, SS220 ((1S,2'5)-Methylpiperidinyl-3-cyclohexen-1-carboxamide), hydroxyethyl isobutyl piperidine carboxylate, an anthranilate-based arachnid/insect repellent, a plant oil, or any combination thereof.

51. The composition of embodiment 49, wherein the anthranilate-based arachnid/insect repellent includes methyl anthranilate, N,N-dimethylanthranilic acid (DMA), ethyl anthranilate (EA), butyl anthranilate (BA), or.
52. The composition of embodiment 49, wherein the one or more naturally-occurring compounds include compounds purified from a plant-derived material or sealife.
53. The composition of embodiment 49, wherein the plant-derived material is a plant oil.
54. The composition of embodiment 50 or 53, wherein the plant oil includes an acyclic monoterpene alcohol or aldehyde, a benzenoid aromatic compound containing at least one oxygenated substituent or side chain, a monocarbocyclic terpene generally having a six-membered ring bearing one or more oxygenated substituents, or any combination thereof.
55. The composition of embodiment 50, 53 or 54, wherein the plant oil includes an α- or β-pinene; α-campholenic aldehyde; α-citronellol; α-iso-amyl-cinnamic; α-pinene oxide; α-cinnamic terpinene; α-terpineol (e.g., 1-methyl-4-isopropyl-1-cyclohexen-8-ol); α-terpinene; λ-terpinene; aldehyde C16 (pure); α-phellandrene; amyl cinnamic aldehyde; amyl salicylate; anethole; anisic aldehyde; benzyl acetate; benzyl alcohol; borneol; callicarpenal; carvacrol; carveol; cineole; cinnamaldehyde; cinnamic alcohol; cis-pinane; citral (e.g., 3,7-dimethyl-2,6-octadienal); citronella; citronellal; citronellol, citronellol dextro (e.g., 3-7-dimethyl-6-octen-1-ol); citronellol; citronellyl acetate; citronellyl nitrile; d-dihydrocarvone; decyl aldehyde; diethyl phthalate; dihydroanethole; dihydrocarveol; dihydrolinalool; dihydromyrcene; dihydromyrcenol; dihydromyrcenyl acetate; dihydroterpineol; dimethyl salicylate; dimethyloctanal; dimethyloctanol; dimethyloctanyl acetate; diphenyl oxide; dipropylene glycol; d-limonene; d-pulegone; estragole; ethyl vanillin, 3-ethoxy-4-hydrobenzaldehyde; p-menthane-3,8-diol; eucalyptol (e.g., cineole); *Eucalyptus citriodora*; *Eucalyptus globulus*; eugenol (e.g., 2-methoxy-4-allyl phenol); fenchol; ferniol; florazon (e.g., 4-ethyl-α,α-dimethyl-benzenepropanal); galaxolide; geraniol (e.g., 2-trans-3,7-dimethyl-2,6-octadien-8-ol); geranyl acetate; geranyl nitrile; guaiacol; heliotropin; herbanate (e.g., 3-(1-methyl-ethyl) bicyclo(2,2,1) hept-5-ene-2-carboxylic acid ethyl ester); hydroxycitronellal; i-carvone; methyl acetate; ionone; isobutyl quinoleine (e.g., 6-secondary butyl quinoline); isobornyl acetate; isobornyl methylether; isoeugenol; isolongifolene; lavandin; limonene; linallol oxide; linallol; linalool; linalyl acetate; I-methyl acetate; longifolene; mandarin; mentha; menthane hydroperoxide; menthol crystals; menthol laevo (e.g., 5-methyl-2-isopropyl cyclohexanol); menthol; menthone laevo (e.g., 4-isopropyl-1-methyl cyclohexan-3-one); methyl anthranilate; methyl cedryl ketone; methyl chavicol; methyl hexyl ether; methyl ionone; methyl salicylate, mineral; musk ambrette; musk ketone; musk xylol; allylisothio-cyanate); myrcene; nerol; neryl acetate; nonyl aldehyde; *Myristica fragrans*; para-cymene; para-hydroxy phenyl butanone crystals (e.g., 4-(4-hydroxyphenyl)-2-butanone); passion palmarosa oil; p-cymene; pennyroyal oil; perillaldehyde; petitgrain; phenyl ethyl alcohol (e.g., 1-phenyl ethyl alcohol and 2-phenyl ethyl alcohol); phenyl ethyl propionate (e.g., 1-phenyl ethyl propionate and 2-phenyl ethyl propionate); phenyl ethyl-2-methylbutyrate; pinane hydroperoxide; pinanol; pine ester; pinene; piperonal; piperonyl acetate; piperonyl alcohol; plinol; plinyl acetate; pseudo ionone; pyrethrum; rhodinol; rhodinyl acetate; rosalinsandenol; spirantol; terpinen-4-ol, terpenoid; terpineol; terpinolene; terpinyl acetate; tert-butylcyclohexyl acetate; tetrahydrolinalool; tetrahydrolinalyl acetate; tetrahydromyrcenol; thymol; trans-2-hexenol; trans-anethole and metabolites thereof; turpentine; vanillin (e.g., 4-hydroxy-3-methoxy benzaldehyde); vetiver; vitalizair; and the like.
56. The composition of any one of embodiments 1-55, further comprising, consisting essentially of or consisting of one or more arachnid/insect repellents not encapsulated.
57. The composition of any one of embodiments 1-11, wherein the one or more silicon dioxide-based particles comprise, consist essentially of or consist of a first silicon dioxide-based particle comprising one or more fragrances.
58. The composition of any one of embodiments 1-11, wherein the one or more silicon dioxide-based particles comprise, consist essentially of or consist of first silicon dioxide-based particles comprising one or more fragrances and second silicon dioxide-based particles comprising one or more fragrances.
59. The composition of any one of embodiments 1-11, wherein the one or more silicon dioxide-based particles comprise, consist essentially of or consist of first silicon dioxide-based particles comprising a first fragrance and second silicon dioxide-based particles comprising a second fragrance.
60. The composition of any one of embodiments 1-59, further comprising, consisting essentially of or consisting of one or more fragrance not encapsulated.
61. The composition of any one of embodiments 57-60, wherein the one or more fragrances are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, or at least 10 of the total weight of the composition, or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, or at most 10% of the total weight of the composition, or about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 4.0% to about 5.0%, about 4.0% to about 6.0%, about 4.0% to about 7.0%, about 4.0% to about 8.0%, about 4.0% to about 9.0%, about 4.0% to about 10%, about 5.0% to about 6.0%, about 5.0% to about 7.0%, about 5.0% to about 8.0%, about 5.0% to about 9.0%, about 5.0% to about 10%, about 6.0% to about 7.0%, about 6.0% to about 8.0%, about 6.0% to about 9.0%, about 6.0% to about 10%, %, about 7.0% to about 8.0%, about 7.0% to about 9.0%, about 7.0% to about 10%, about 8.0% to about 9.0%, about 8.0% to about 10%, about 9.0% to about 10%, of the total weight of the composition.

62. The composition of any one of embodiments 57-60, wherein the one or more fragrances are present in an amount of about 0.25% to about 8%, about 0.5% to about 6%, about 1% to about 5%, about 2% to about 4% or about 3% by weight of the total composition.

63. The composition of any one of embodiments 57-60, wherein the one or more fragrances are present in an amount of about 0.1% to about 6%, about 0.2% to about 5%, about 0.3% to about 4%, about 0.5% to about 2% or about 1% by weight of the total composition.

64. The composition of any one of embodiments 1-63, wherein the one or more silicon dioxide-based particles comprise, consist essentially of or consist of first silicon dioxide-based particles comprising one or more moisturizing agents.

65. The composition of any one of embodiments 1-63, wherein the one or more silicon dioxide-based particles comprise, consist essentially of or consist of first silicon dioxide-based particles comprising one or more moisturizing agents and second silicon dioxide-based particles comprising one or more moisturizing agents.

66. The composition of any one of embodiments 1-63, wherein the one or more silicon dioxide-based particles comprise, consist essentially of or consist of a first silicon dioxide-based particle comprising a first moisturizing agent and a second silicon dioxide-based particle comprising a second moisturizing agent.

67. The composition of any one of embodiments 1-66, further comprising, consisting essentially of or consisting of one or more moisturizing agents not encapsulated.

68. The composition of any one of embodiments 64-67, wherein the first moisturizing agent is in an amount of about 1% to about 5% and the second moisturizing agent is in an amount of about 95% to about 99%, or wherein the first moisturizing agent is in an amount of about 6% to about 10% and the second moisturizing agent is in an amount of about 90% to about 94%, or wherein the first moisturizing agent is in an amount of about 11% to about 15% and the second moisturizing agent is in an amount of about 85% to about 89%, or wherein the first moisturizing agent is in an amount of about 16% to about 20% and the second moisturizing agent is in an amount of about 80% to about 84%, or wherein the first moisturizing agent is in an amount of about 21% to about 25% and the second moisturizing agent is in an amount of about 75% to about 79%, or wherein the first moisturizing agent is in an amount of about 26% to about 30% and the second moisturizing agent is in an amount of about 70% to about 74%, or wherein the first moisturizing agent is in an amount of about 31% to about 35% and the second moisturizing agent is in an amount of about 65% to about 69%, or wherein the first moisturizing agent is in an amount of about 36% to about 40% and the second moisturizing agent is in an amount of about 60% to about 64%, or wherein the first moisturizing agent is in an amount of about 41% to about 45% and the second moisturizing agent is in an amount of about 55% to about 59%, or wherein the first moisturizing agent is in an amount of about 46% to about 50% and the second moisturizing agent is in an amount of about 50% to about 54%.

69. The composition of any one of embodiments 64-68, wherein the one or more moisturizing agents include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, saccharide isomerate, salts of pyrrolidone carboxylic acid, potassium PCA, propylene glycol, sodium glucuronate, sodium PCA, sorbitol, sucrose, trehalose, urea, and xylitol.

70. The composition of any one of embodiments 1-69, further comprising, consisting essentially of or consisting of one or more polyquaterniums, one or more surfactants, one or more film formers, one or more emollients, one or more thickening agents, one or more soap bases, one or more polymers, or any combination thereof.

71. The composition of embodiment 70, wherein the one or more polyquaterniums are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition, or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition, or about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

72. The composition of embodiment 70 or 71, wherein the one or more polyquaterniums are in an amount of about 0.1% to about 10%, about 0.2% to about 8%, about 0.4% to about 6%, about 0.6% to about 5%, about 2.5% by weight of the total composition.

73. The composition of embodiment 70 or 71, wherein the one or more polyquaterniums are in an amount of about 0.1% to about 10%, about 0.25% to about 8%, about 0.5% to about 5%, about 1% to about 3% or about 2% by weight of the total composition.

74. The composition of embodiment 70 or 71, wherein the one or more polyquaterniums are in an amount of about 0.1% to about 7%, about 0.1% to about 5%, about 0.1% to about 3%, about 0.25% to about 2.5% or about 0.5% by weight of the total composition.

75. The composition of any one of embodiments 70-74, wherein the one or more polyquaterniums include polyquaternium-1, polyquaternium-2, polyquaternium-4 (CELQUAT L-200), polyquaternium-5, polyquaternium-6, polyquaternium-7, polyquaternium-10, polyquaternium-11, polyquaternium-15, polyquaternium-16, polyquaternium-22, polyquaternium-28, polyquaternium-32, polyquaternium-37, polyquaternium-39, polyquaternium-40, polyquaternium-41, polyquaternium-42, polyquaternium-44, polyquaternium-45, polyquaternium-46, polyquaternium-47, polyquaternium-64 or any combination thereof.

76. The composition of any one of embodiments 70-76, wherein the one or more surfactants are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition, or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition, or about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

77. The composition of any one of embodiments 70-76, wherein the one or more surfactants are present in an amount of about 0.1% to about 10%, about 0.25% to about 8%, about 0.5% to about 5%, about 1% to about 3%, about 1.6% by weight of the total composition.
78. The composition of any one of embodiments 70-76, wherein the one or more surfactants are present in an amount of about 3% to about 17%, about 5% to about 15%, about 7% to about 13%, about 9% to about 11% or about 10% by weight of the total composition.
79. The composition of any one of embodiments 70-76, wherein the one or more surfactants are present in an amount of about 2% to about 18%, about 3% to about 15%, about 4% to about 13%, about 5% to about 12% or about 6% to about 11% by weight of the total composition.
80. The composition of any one of embodiments 70-76, wherein the one or more surfactants are present in an amount of about 1% to about 20%, about 4% to about 14%, about 7% to about 11%, about 8% to about 10% or about 8.8% by weight of the total composition.
81. The composition of any one of embodiments 70-80, wherein the one or more surfactants include one or more cationic surfactants, one or more anionic surfactants, one or more non-ionic surfactants, one or more zwitterionic surfactants, one or more amphoteric surfactants, or any combination thereof
82. The composition of any one of embodiments 70-80, wherein the one or more surfactants include one or more anionic surfactants present in an amount of about 0.5% to about 15%, about 2% to about 12%, about 4% to about 10%, about 6% to about 8% or about 7% by weight of the total composition.
83. The composition of any one of embodiments 70-80, wherein the one or more surfactants include one or more anionic surfactants present in an amount of about 1% to about 16%, about 1% to about 12%, about 3% to about 9%, about 5% to about 7% or about 5.6% by weight of the total composition.
84. The composition of any one of embodiments 81-83, wherein the one or more anionic surfactants include one or more sulfated monoglyceride surfactants, one or more olefin sulfonate surfactants, one or more alkylbenzene sulfonate surfactants, one or more alkane sulfonate surfactants, one or more alkyl sulfosuccinate surfactants, one or more acyl isethionate surfactants or any combination thereof.
85. The composition of embodiment 84, wherein the one or more alkyl sulfosuccinate surfactants include disodium N-octadecylsulfosuccinamate, diammonium lauryl sulfosuccinate, disodium laureth sulfosuccinate, tetrasodium N-(1,2-dicarboxyethyl)-N-octadecylsulfosuccinate, diamyl ester of sodium sulfosuccinic acid, dihexyl ester of sodium sulfosuccinic acid and dioctyl esters of sodium sulfosuccinic acid; sodium dodecyl sulfate (or sodium lauryl sulfate), sodium laureth sulfate, ammonium lauryl sulfate, or any combination thereof.
86. The composition of embodiment 85, wherein the one or more acyl isethionate surfactants include an alkylglyceryl ether sulfonate, a sodium cocoglyceryl ether sulfonate, a sulfonated fatty acid, a sulfonated methyl ester, an acyl glutamate, an alkanoyl sarcosinate, an alkyl ether carboxylate, an acyl lactylate, a carboxylate, a saponified soap, or any combination thereof.
87. The composition of embodiment 86, wherein the one or more acyl isethionate surfactants ammonium cocoyl isethionate, sodium cocoyl isethionate, sodium lauroyl isethionate, sodium lauroyl sarcosinate, lauroyl sarcosine, sodium cocoyl sarcosinate, ammonium lauroyl sarcosinate, sodium laureth carboxylate, sodium cocoyl lactylate, sodium lauroyl carboxylate, sodium cocoyl carboxylate, ammonium lauroyl carboxylate, sodium laurate, sodium myristate, sodium palmitate, sodium stearate, sodium tallowate, cocoate or any combination thereof.
88. The composition of any one of embodiments 70-87, wherein the one or more surfactants include one or more amphoteric surfactants present in an amount of about 0.1% to about 9%, about 0.25% to about 7%, about 0.5% to about 5%, about 2% to about 4%, about 3% by weight of the total composition.
89. The composition of any one of embodiments 70-87, wherein the one or more surfactants include one or more amphoteric surfactants present in an amount of about 0.1% to about 5%, about 0.25% to about 4%, about 0.5% to about 3%, about 0.75% to about 2.5% or about 1% to about 2% by weight of the total composition.
90. The composition of any one of embodiments 70-87, wherein the one or more surfactants include one or more amphoteric surfactants present in an amount of about 0.1% to about 10%, about 0.25% to about 8%, about 0.5% to about 5%, about 1% to about 3% or about 1.6% by weight of the total composition.
91. The composition of any one of embodiments 88-90, wherein the one or more amphoteric surfactants include one or more betaines, one or more sultaines, one or more hydroxysultaines, one or more alkyliminoacetates, one or more iminodialkanoates, one or more aminoalkanoates or any combination thereof.
92. The composition of any one of embodiments 88-90, wherein the one or more betaines include coco dimethyl carboxymethyl betaine, lauryl dimethyl carboxymethyl betaine, lauryl dimethyl α-carboxyethyl betaine, cetyl dimethyl carboxymethyl betaine, cetyl dimethyl betaine, lauryl bis-(2-hydroxyethyl) carboxymethyl betaine, oleyl dimethyl gamma-carboxypropyl betaine, lauryl bis-(2-hydroxypropyl)α-carboxyethyl betaine, coco dimethyl sulfopropyl betaine, lauryl dimethyl sulfoethyl betaine, lauryl bis-(2-hydroxyethyl) sulfopropyl betaine, oleyl betaine, cocamidopropyl betaine, an amidobetaine, an amidosulfobetaine or any combination thereof.
93. The composition of any one of embodiments 70-92, wherein the one or more surfactants include one or more acyl taurate surfactants present in an amount of about 0.1% to about 5%, about 0.25% to about 4%, about 0.5% to about 3%, about 0.75% to about 2.5% or about 1% to about 2% by weight of the total composition.
94. The composition of embodiment 93, wherein the one or more acyl taurate surfactants include sodium methyl cocoyl taurate and sodium methyl oleoyl taurate, taurine, a N-alkyltaurine or any combination thereof.
95. The composition of any one of embodiments 70-94, wherein the one or more film formers are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25%, at least 30%, at least 35% or at least 40% of the total weight of the composition, or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25%, at most 30%, at most 35% or at most 40% of the total weight of the composition, or about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19%, about 5.0% to about 20%, about 5.0% to about 25%, about 5.0% to about 30%, about 10% to about 15%, about 10% to about 20%, about 10% to about 25%, about 10% to about 30%, about 10% to about 35%, about 10% to about 40%, about 15% to about 20%, about 15% to about 25%, about 15% to about 30%, about 15% to about 35%, about 15% to about 40%, about 20% to about 25%, about 20% to about 30%, about 20% to about 35% or about 20% to about 40% of the total weight of the composition.

96. The composition of any one of embodiments 70-94, wherein the one or more film formers are present in an amount of about 1% to about 6%, about 1.5% to about 4.5%, about 2% to about 4%, about 2.5% to about 3.5%, about 3% or about 2.5% by weight of the total composition.

97. The composition of any one of embodiments 70-94, wherein the one or more film formers are present in an amount of about 0.25% to about 8%, about 0.5% to about 6%, about 1% to about 5%, about 2% to about 4% or about 3% by weight of the total composition.

98. The composition of any one of embodiments 70-94, wherein the one or more film formers are present in an amount of about 19% to about 31%, about 21% to about 29%, about 22% to about 28%, about 24% to about 26% or about 25% by weight of the total composition.

99. The composition of any one of embodiments 70-98, wherein the one or more film formers include petroleum, an acrylate copolymer, a synthetic wax of branched polyalpha olefin polymers, a $C_{28}$-$C_{52}$ olefin/undecylenic acid copolymer 100. The composition of any one of embodiments 70-98, wherein the one or more film formers comprising, consisting essentially of or consisting of petrolatum, dimethicone, stearamidopropyl dimethylamine, stearate and tocopheryl acetate.

101. The composition of any one of embodiments 70-100, wherein the one or more emollients are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition, or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition, or about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

102. The composition of any one of embodiments 70-101, wherein the one or more emollients are in an amount of about 0.25% to about 10%, about 0.5% to about 8%, about 1% to about 6%, about 2% to about 5%, or about 3.5% of the total weight of the composition.

103. The composition of any one of embodiments 70-101, wherein the one or more emollients are in an amount of about 6% to about 18%, about 8% to about 16%, about 9% to about 15%, about 11% to about 13%, or about 12% of the total weight of the composition.

104. The composition of any one of embodiments 70-103, wherein the one or more emollients comprise capryllic capric triglyceride.

105. The composition of any one of embodiments 70-104, wherein the one or more thickening agents are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition, or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition, or about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

106. The composition of any one of embodiments 70-105, wherein the one or more thickening agents are in an amount of about 0.5% to about 12%, about 1% to about 10%, about 1.5% to about 8.5%, about 2.5% to about 6.5%, or about 4.5% of the total weight of the composition.

107. The composition of any one of embodiments 70-106, wherein the one or more thickening agents include one or more silicone elastomer thickening agents and one or more sodium acrylate-sodium acryloyldimethyl taurate copolymer-based thickening agents.

108. The composition of embodiment 107, wherein one or more silicone elastomer thickening agents are in an amount of about 0.1% to about 9%, about 0.2% to about 7%, about 0.25% to about 5%, about 0.5% to about 3.5%, or about 2% of the total weight of the composition.
109. The composition of embodiment 107 or 108, wherein the one or more silicone elastomer thickening agents include a dimethicone-vinyldimethyl trimethylsiloxysilicate-dimethicone crosspolymer.
110. The composition of any one of embodiments 107-109, wherein one or more sodium acrylate-sodium acryloyldimethyl taurate copolymer-based thickening agents are in an amount of about 0.1% to about 9%, about 0.2% to about 7%, about 0.5% to about 5%, about 1% to about 4%, or about 2.5% of the total weight of the composition.
111. The composition of any one of embodiments 107-110, wherein the one or more sodium acrylate-sodium acryloyldimethyl taurate copolymer-based thickening agents include an acrylate-sodium acryloyldimethyl taurate copolymer-based thickening agent comprising isohexadecane and polysorbate 80.
112. The composition of any one of embodiments 70-111, wherein the one or more polymers are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition, or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition, or about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.
113. The composition of any one of embodiments 70-111, wherein the one or more polymers are present in an amount of about 1% to about 10%, about 3% to about 9%, about 4% to about 8%, about 5% to about 7% or about 6% by weight of the total composition.
114. The composition of any one of embodiments 1-113 further comprising, consisting essentially of or consisting of one or more unloaded silicon dioxide-based particles.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compositions disclosed herein, and the methods or uses pertaining to the disclosed compositions.

Example 1

Preparation of Antioxidant Blend

This example illustrates how to make a slurry comprising silicon dioxide-based particles, like diatomaceous earth-based particles loaded with antioxidant blend.

A mixture is made comprising an antioxidant agent mixture comprising 10% soybean Oil, 10% tocopheryl acetate, 10% rosemary oil and 10% pomegranate oil, and 3% mulberry wax and this mixture is heated to about 55° C. to about 70° C. Silicon dioxide-based particles, like diatomaceous earth-based particles, such as, e.g., IMERCARE® 03D is added to the antioxidant agent mixture to an amount of 57% by weight of the antioxidant agent mixture and incubated for about 1 hour to about 24 hours. The resulting process results in slurry comprising silicon dioxide-based particles comprising 25% soybean oil, 25% tocopheryl acetate, 25% rosemary oil and 25% pomegranate oil.

Example 2

Preparation of Antioxidant Lotion

This example illustrates how to make an antioxidant lotion composition using silicon dioxide-based particles loaded with an antioxidant blend.

About 30% of loaded silicon dioxide-based particle slurry prepared according to Example 1 is added to 70% of an antioxidant lotion composition shown in Table 1. The antioxidant lotion composition is prepared by adding all the components in order, except for the preservative, and heated to about 50° C. to about 80° C. until the emulsifier is melted. The mixture is then cooled to room temperature and the preservative is added. In alternative formulations, up to 50% loaded silicon dioxide-based particles can be mixed with the antioxidant lotion composition adjusted to achieve a combined 100% by weight formulation.

TABLE 1

Antioxidant Lotion Composition

| Component | Amount |
| --- | --- |
| Water | 86% |
| Glycerin (Mosturizing Agent) | 1% |
| Antioxidant Blend (Example 1) | 10% |
| Jaguar ® C-17 (Cationic Polymer) | 0.3% |
| Caprylyl Glycol (Emollient) | 2% |
| Cetearyl Alcohol/Cetereth 20 (Emulsifier) | 0.2% |
| Phenoxyethanol (Preservative) | 0.5% |

Example 3

Preparation of Antioxidant Bodywash

This example illustrates how to make an antioxidant bodywash composition using silicon dioxide-based particles loaded with an antioxidant blend.

About 30% of loaded silicon dioxide-based particle slurry prepared according to Example 1 is added to 70% of an antioxidant bodywash composition shown in Table 2. The antioxidant bodywash composition is prepared by adding all the components and heated to about 50° C. to about 80° C. until the emulsifier is melted. The mixture is then cooled to room temperature and the pH of the composition is adjusted using citric acid, 20% sodium hydroxide or sodium chloride as needed. In alternative formulations, up to 50% loaded silicon dioxide-based particles can be mixed with the antioxidant bodywash composition adjusted to achieve a combined 100% by weight formulation.

TABLE 2

Antioxidant Bodywash Composition

| Component | Amount |
| --- | --- |
| Water | 60% |
| Antioxidant Blend (Example 1) | 10% |
| Polyquaternium-10 (Cationic Polymer) | 0.15% |
| Sodium Lauryl Sulfate (Surfactant) | 15% |
| Sodium Methyl Cocoyl Taurate (Surfactant) | 2.5% |
| Cocamidopropyl Betaine (Surfactant) | 12% |

Example 4

Preparation of Sunscreen Blend

This example illustrates how to make a slurry comprising silicon dioxide-based particles, like diatomaceous earth-based particles loaded with sunscreen agent blend.

A sunscreen agent mixture comprising 22.5% Octinoxate, 20% Homosalate, 7.5% Avobenzone, 6% polyamine 3 and 10% polyester 25 is mixed and heated to about 55° C. to about 70° C. Silicon dioxide-based particles, like diatomaceous earth-based particles, such as, e.g., IMERCARE® 03D is added to the sunscreen agent mixture to an amount of 34% by weight of the sunscreen agent mixture for about 1 hour to about 24 hours. The resulting process results in slurry comprising silicon dioxide-based particles comprising 42% Octinoxate, 37% Homosalate and 13% Avobenzone, 3% polyamine 3 and 5% polyester 25.

Example 5

Preparation of Sunscreen Lotion

This example illustrates how to make a sunscreen lotion composition using silicon dioxide-based particles loaded with a sunscreen agent blend.

About 30% of loaded silicon dioxide-based particle slurry prepared according to Example 1 is added to 70% of a sunscreen lotion composition shown in Table 3. The sunscreen lotion composition is prepared by adding all the components in order, except for the preservative, and heated to about 50° C. to about 80° C. until the emulsifier is melted. The mixture is then cooled to room temperature and the preservative is added. In alternative formulations, up to 50% loaded silicon dioxide-based particles can be mixed with the sunscreen lotion composition adjusted to achieve a combined 100% by weight formulation.

TABLE 3

Sunscreen Lotion Composition

| Component | Amount |
| --- | --- |
| Water | 63% |
| Glycerin (Mosturizing Agent) | 1% |
| Sunscreen Blend (Example 4) | 30% |
| Jaguar ® C-17 (Cationic Polymer) | 0.3% |
| Acrylate Copolymer (Film Former) | 3% |
| Caprylyl Glycol (Emollient) | 2% |
| Phenoxyethanol (Preservative) | 0.5% |

Example 6

Preparation of Sunscreen Soap

This example illustrates how to make a soap comprising silicon dioxide-based particles, like diatomaceous earth-based particles loaded with sunscreen agent blend.

A sunscreen agent mixture comprising 57% Homosalate, 28.5% octylsalate, 14.25% Avobenzone, 20% Solastay 51 is mixed and heated to about 55° C. to about 70° C. Silicon dioxide-based particles, like diatomaceous earth-based particles, such as, e.g., IMERCARE® 03D is added to the sunscreen agent mixture to an amount of 26% by weight of the sunscreen agent mixture for about 1 hour to about 24 hours. The resulting process results in slurry comprising silicon dioxide-based particles comprising 37% Homosalate. 18% octylsalate, 9.2% Avobenzone, and 13% Solastay 51. About 11% of this loaded silicon dioxide-based particle slurry is added to a soap base (Table 4), heated to 70° C. for about 1 hour, cooled to about 60° C. and poured into molds to form soap bars.

To make the soap base, glycerol, 70% sorbitol solution, and sodium laureth sulfate were heated to 65° C. Once this temperature was reached stearic acid and myristic acid were added and the heat increased to 70° C. Lye is then slowly added and mix for about 20 minutes until mixture becomes transparent and then heated for at least 1 hour above 70° C. Base 723 and Triethanolamine and then added. The mixture is then cooled to 60° C. and then the methyl paraben is added.

TABLE 4

Soap Base

| Component | Amount |
|---|---|
| Glycerol (Vegetable Glycerin) | 30% |
| 70% Sorbitol Solution | 15% |
| Sodium Laureth Sulfate | 22% |
| Base 723 | 10.5% |
| Stearic Acid | 10% |
| Myristic Acid | 5% |
| Lye (50% NaOH) | 5% |
| Triethanolamine | 2% |
| Methyl Paraben | 0.5% |

Example 7

Preparation of Insect/Arachnid Repellant Blend

This example illustrates how to make a slurry comprising silicon dioxide-based particles, like diatomaceous earth-based particles loaded with insect/arachnid repellant blend.

An insect/arachnid repellant mixture is made by mixing the components listed in Table 5 with 17% beeswax, 4% castoralatum, 3% Stearic acid and 5% polyethylene and heated to about 55° C. to about 70° C. Silicon dioxide-based particles, like diatomaceous earth-based particles, such as, e.g., IMERCARE® 03D is added to the sunscreen agent mixture to an amount of 28% by weight of the insect/arachnid repellant mixture for about 1 hour to about 24 hours. The resulting process results in slurry comprising silicon dioxide-based particles comprising the components in the amounts listed in Table 5 (Particle Amounts).

TABLE 5

Insect/Arachnid Repellant Blend

| Component | Mixture Amount | Particle Amount |
|---|---|---|
| SoyBean Oil | 14.5% | 10.3% |
| Clove Oil | 2.1% | 1.5% |
| Geraniol | 16.3% | 11.6% |
| Peppermint Oil | 1.7% | 1.2% |
| Lemon Grass Oil | 2.1% | 1.5% |
| Rosemary Oil | 2.1% | 1.5% |
| Citronella Oil | 1.4% | 1% |
| Thyme (Red) Oil | 1.7% | 1.2% |
| Cinnamon Leaf Oil | 2.2% | 1.6% |
| *Geranium* Oil | 18.1% | 12.8% |
| Wintergreen Oil | 10.1% | 7.2% |

Example 8

Preparation of Insect/Arachnid Repellant Blend

This example illustrates how to make a powder comprising silicon dioxide-based particles, like diatomaceous earth-based particles loaded with insect/arachnid repellant blend.

An insect/arachnid repellant mixture is made by mixing the components listed in Table 6 and heated to about 55° C. to about 70° C. Silicon dioxide-based particles, like diatomaceous earth-based particles, such as, e.g., IMERCARE® 03D is added to the sunscreen agent mixture to an amount of 33% by weight of the insect/arachnid repellant mixture for about 1 hour to about 24 hours. About 1% fumed silica and an additional 34.5% silicon dioxide-based particles, like diatomaceous earth-based particles in then added to resulting slurry. The resulting process results in powder comprising silicon dioxide-based particles comprising the components in the amounts listed in Table 6 (Particle Amounts).

TABLE 6

Insect/Arachnid Repellant Blend

| Component | Mixture Amount | Particle Amount |
|---|---|---|
| SoyBean Oil | 13.2% | 9.8% |
| Clove Oil | 1.9% | 1.4% |
| Geraniol | 14.9% | 11.1% |
| Peppermint Oil | 1.6% | 1.2% |
| Lemon Grass Oil | 1.9% | 1.4% |
| Rosemary Oil | 1.9% | 1.4% |
| Citronella Oil | 1.3% | 0.9% |
| Thyme (Red) Oil | 1.6% | 1.2% |
| Cinnamon Leaf Oil | 2.0% | 1.5% |
| *Geranium* Oil | 16.5% | 12.3% |
| Wintergreen Oil | 9.3% | 6.9% |

Example 9

Preparation of Insect/Arachnid Repellant Lotion

This example illustrates how to make an insect/arachnid repellant lotion composition using silicon dioxide-based particles loaded with an insect/arachnid repellant blend.

About 10% of loaded silicon dioxide-based particle slurry prepared according to Example 6 is added to 90% of a salt solution shown in Table 7 and 0.03% xanthan gum. In alternative formulations, up to 30% loaded silicon dioxide-based particles can be mixed with the salt solution adjusted to achieve a combined 100% by weight formulation.

TABLE 7

Salt Solution

| Component | Amount |
|---|---|
| Water | 92.45% |
| Sodium lauryl sulfate | 5% |
| Calcium chloride | 1% |
| Citric Acid | 0.7$ |
| Urea | 0.7% |
| Sodium benzoate | 0.1% |
| Patasium sorbate | 0.05% |

Example 10

Arachnid and Insect Repellency Assay

Experiments were conducted to assess the insect/arachnid repellency of compositions disclosed herein using two different assays.

To conduct a tick repellent assay, a 4 cm×8 cm basket with a 4 cm×4 cm opening in the bottom is suspended over a petri dish containing 10 *Rhipicephalus sanguineus* (Brown Dog Tick). A 4 cm×4 cm filer paper is attached to a 4 cm×8 cm paper and placed at the bottom of the basket so that the 4 cm×4 cm filer paper cover the 4 cm×4 cm opening located in the basket's bottom. A sample of blood is placed within the 4 cm×4 cm area of the filter paper. For the control composition, the filter paper is moistened with water and the number and of ticks attached to the bottom of the basket and the location distance from the 4 cm×4 cm filter paper was assessed during a 10 minute time period at 3 minutes, 5 minutes and 10 minutes. For the test compositions, the filter paper is treated by added 1 g/600 cm$^2$ of a test composition and the number and of ticks attached to the bottom of the basket and the location distance from the 4 cm×4 cm filter paper was assessed during a 10 minute time period at 3 minutes, 5 minutes and 10 minutes. Test composition 1 is a liquid composition comprising about 20% DEET. Test Composition 2 is a composition comprising silicon dioxide-based particles, like diatomaceous earth-based particles, loaded with an insect.arachnid repellent blend according to Example 7. Test composition 3 is a commercial product (Bug Away) which comprises castor oil, geranium oil, soybean oil, cedarwood oil, citronella oil, peppermint oil, lemongrass oil and wintergreen oil. The data is shown in Table 8. Test Composition 2 showed a significant repellent activity compared to the control and was effective in repelling ticks to a similar degree as a 20% DEET composition (Test Composition 1).

TABLE 8

Tick Repellent Assay

| Composition | Post-Treatment Time (2 hr) | Post-Treatment Time (4 hr) | Post-Treatment Time (6 hr) |
| --- | --- | --- | --- |
| Untreated Control | 23% | 8% | 18% |
| Test Composition 1 | — | 100% | 100% |
| Test Composition 2 | 95% | 85% | 78% |
| Test Composition 3 | — | 43% | — |

Assay for each test composition was repeated four times.

To conduct an AEDSAE 16 assay, a mosquito cage is set up with 25 female *Aedes aegypti* mosquitoes. The top lid of the cage has a 2.5" by 6" opening in the center. A collagen membrane is place over the opening and is used as the test surface because it mimics human skin. A test subject's forearm is then positioned over the opening. Mesh is placed on the top side of the test surface to prevent direct contact of the test surface with the test subject's arm and disposable wood spacers are placed on top of the top cover to elevate the test subject's arm from the test substance and to prevent the mosquitoes from being able to feed on the test subject. Pre-treatment landing and probing numbers were obtained by counting the number of mosquitoes that landed and probed the collagen membrane during a 5 minute time period. Treatment landing and probing numbers were obtained as follows: for the control composition, the collagen membrane is moistened with water and landing and probing numbers were obtained by counting the number of mosquitoes that landed and probed the treated collagen membrane during a 5 minute time period; for the test compositions, the collagen membrane is treated by added 1 g/600 cm$^2$ of a test composition and landing and probing numbers were obtained by counting the number of mosquitoes that landed and probed the treated collagen membrane during a 5 minute time period. Test composition 1 is a liquid composition comprising about 20% DEET. Test Composition 2 is a composition comprising silicon dioxide-based particles, like diatomaceous earth-based particles, loaded with an insect.arachnid repellent blend according to Example 7. Test composition 3 is a commercial product (Bug Away) which comprises castor oil, geranium oil, soybean oil, cedarwood oil, citronella oil, peppermint oil, lemongrass oil and wintergreen oil. Landing and probing numbers were collected at 1 hour, 2 hours and 4 hours after treatment of the collagen membrane. The percent landing and probing numbers were calculated by comparing the number of landing and probes during the pre-treatment evaluation to the number of landing and probes during the treatment evaluation at all three time intervals. The data is shown in Table 9. The Test Composition 2 showed a significant repellent activity compared to the control and was just as effective in repelling mosquitoes as a 20% DEET composition (Test Composition 1).

TABLE 9

Mosquito Repellent Assay

| Composition | Post-Treatment Time (2 hr) | | Post-Treatment Time (4 hr) | | Post-Treatment Time (6 hr) | |
| --- | --- | --- | --- | --- | --- | --- |
| | Landings | Probes | Landings | Probes | Landings | Probes |
| Untreated Control | −18% | −22% | −7% | −7% | 20% | 17% |
| Test Composition 1 | — | — | 90% | 100% | 96% | 100% |
| Test Composition 2 | 100% | 100% | 67% | 93% | 100% | 100% |
| Test Composition 3 | — | — | 71% | 91% | 87% | 96% |

Assay for each test composition was repeated four times.

Example 11

Evaporation Rate Assay

Experiments were conducted to assess the evaporation rates of compositions disclosed herein.

The evaporation rate of an insect/arachnid repellent blend as described in Example 7 was examined as a liquid composition (Test Composition 1) and as a composition comprising silicon dioxide-based particles, like diatomaceous earth-based particles, loaded with an insect/arachnid repellent blend as described in Example 7 (Test Composition 2). An equal amount of each composition was added to a solid substrate and immediately weighted. The weight of the substrate was measured over the course of three days as indicated in Table 10. The results indicate that an insect/arachnid repellent blend loaded in silicon dioxide-based particles, like diatomaceous earth-based particles, resulted in an evaporation rate that was less than and more consistent than the evaporation rate of the insect/arachnid repellent blend in Test Composition 1.

TABLE 10

Evaporate Rate of Compositions

| Time (Min) | Weight Test Composition 1 (g) | Weight Test Composition 2 (g) |
|---|---|---|
| 0 | 2.8 | 2.8 |
| 15 | 2.65 | 2.78 |
| 30 | 2.48 | 2.74 |
| 45 | 2.4 | 2.72 |
| 60 | 2.37 | 2.71 |
| 75 | 2.34 | 2.7 |
| 90 | 2.31 | 2.69 |
| 105 | 2.3 | 2.69 |
| 120 | 2.3 | 2.68 |
| 135 | 2.29 | 2.68 |
| 150 | 2.28 | 2.67 |
| 165 | 2.28 | 2.67 |
| 180 | 2.28 | 2.67 |
| 240 | 2.28 | 2.66 |
| 300 | 2.28 | 2.65 |
| 360 | 2.28 | 2.64 |
| 420 | 2.28 | 2.64 |
| 480 | 2.28 | 2.63 |
| 540 | 2.28 | 2.63 |
| 600 | 2.28 | 2.62 |
| 660 | 2.28 | 2.62 |
| 720 | 2.28 | 2.61 |
| 780 | 2.28 | 2.61 |
| 840 | 2.28 | 2.61 |
| 900 | 2.28 | 2.6 |
| 960 | 2.28 | 2.6 |
| 1020 | 2.28 | 2.6 |
| 1080 | 2.28 | 2.6 |
| 1140 | 2.28 | 2.6 |
| 1200 | 2.28 | 2.59 |

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only and is not intended to limit the scope of the present invention, which is defined solely by the claims. Accordingly, the present invention is not limited to that precisely as shown and described.

The invention claimed is:

1. A composition comprising:
   about 5.0% to about 30% by weight of the total composition of one or more diatomaceous earth particles, the one or more diatomaceous earth particles: loaded with at least 25% by weight of the total composition of a first active agent, wherein the first active agent is one or more insect or arachnid repellents consisting of plant oil, said plant oil comprising geraniol and geranium oil; and
   one or more core modifiers, the one or more core modifiers comprising polyethylene, stearic acid, and beeswax, wherein the one or more core modifiers coat the surface of the one or more diatomaceous earth particles, wherein the composition is manufactured as a solid.

2. The composition of claim 1, wherein the one or more diatomaceous earth particles are in an amount of about 5.0% to about 25% by weight of the total composition.

3. The composition of claim 1, wherein the one or more diatomaceous earth particles are in an amount of about 15.0% to about 25% by weight of the total composition.

4. The composition of claim 1, wherein the plant oil is selected from the group consisting of geraniol, geranium oil, cinnamon oil, lemon grass oil, clove oil, rosemary oil, peppermint oil, soybean oil, thyme oil, citronella oil, wintergreen oil, and combinations thereof.

5. The composition of claim 1, wherein the one or more core modifiers further comprise a natural wax or a synthetic wax.

6. A composition consisting of:
   about 5.0% to about 30% by weight of the total composition of one or more diatomaceous earth particles, the one or more diatomaceous earth particles loaded with at least 25% by weight of the total composition of a first active agent, wherein the first active agent is one or more insect or arachnid repellents consisting of plant oil, the plant oil selected from the group consisting of geraniol, geranium oil, cinnamon oil, lemon grass oil, clove oil, rosemary oil, peppermint oil, soybean oil, thyme oil, citronella oil, wintergreen oil, and combinations thereof;

one or more core modifiers, the one or more core modifiers comprising polyethylene, stearic acid, and beeswax, wherein the one or more core modifiers coat the surface of the one or more diatomaceous earth particles; and castor oil and hydrogenated castor oil.

7. The composition of claim 6, wherein the one or more diatomaceous earth particles are in an amount of about 5.0% to about 25% by weight of the total composition.

8. The composition of claim 6, wherein the one or more diatomaceous earth particles are in an amount of about 15.0% to about 25% by weight of the total composition.

9. A composition comprising:
about 5.0% to about 30% by weight of the total composition of one or more diatomaceous earth particles, the one or more diatomaceous earth particles loaded with
about 12.3% to about 12.8% geranium oil;
about 11.1% to about 11.6% geraniol;
about 9.8% to about 10.3% soybean oil;
about 1.5% to about 1.6% cinnamon oil;
about 1.4% to about 1.5% lemon grass oil;
about 1.4% to about 1.5% clove oil;
about 1.4% to about 1.5% rosemary oil;
about 1.2% peppermint oil;
about 1.2% thyme oil; and
about 0.9% to about 1% citronella oil;
one or more core modifiers, the one or more core modifiers comprising polyethylene, stearic acid, and beeswax, wherein the one or more core modifiers coat the surface of the one or more diatomaceous earth particles; and
castor oil and hydrogenated castor oil.

10. The composition of claim 9, further comprising about 6.9% to about 7.2% wintergreen oil.

* * * * *